(12) United States Patent
Liao et al.

(10) Patent No.: US 12,090,189 B2
(45) Date of Patent: Sep. 17, 2024

(54) POLYPEPTIDE INHIBITOR OF DE NOVO LIPOGENESIS IN CANCER CELLS

(71) Applicant: University of Florida Research Foundation, Inc., Gainesville, FL (US)

(72) Inventors: Daiqing Liao, Gainsville, FL (US); Iqbal Mahmud, Gainesville, FL (US); Guimei Tian, Hawthorne, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 18/474,456

(22) Filed: Sep. 26, 2023

(65) Prior Publication Data

US 2024/0066094 A1    Feb. 29, 2024

Related U.S. Application Data

(62) Division of application No. 17/044,547, filed as application No. PCT/US2019/026011 on Apr. 5, 2019, now abandoned.

(60) Provisional application No. 62/653,183, filed on Apr. 5, 2018.

(51) Int. Cl.
| | |
|---|---|
| *A61K 38/04* | (2006.01) |
| *A61K 47/10* | (2017.01) |
| *A61K 47/36* | (2006.01) |
| *A61P 35/00* | (2006.01) |
| *A61K 45/06* | (2006.01) |

(52) U.S. Cl.
CPC .............. *A61K 38/04* (2013.01); *A61K 47/10* (2013.01); *A61K 47/36* (2013.01); *A61P 35/00* (2018.01); *A61K 45/06* (2013.01)

(58) Field of Classification Search
CPC ........ A61K 38/04; A61K 47/10; A61K 47/36; A61K 45/06; A61K 38/00; A61K 38/08; A61K 38/10; A61K 38/13; A61K 38/17; A61K 45/00; A61P 35/00
See application file for complete search history.

(56) References Cited

PUBLICATIONS

Santiago et al, Cell Cycle, 8:1, 76-87; Jan. 2009 (Year: 2009).*
Lin et al, Molecular Cell, 24, 341-345, Nov. 3, 2006 (Year: 2006).*
Muromoto et al., Physical and functional interactions between Daxx and STAT3.Oncogene 25, 2131-2136, 2006.
Nelson et al., 27-Hydroxycholesterol links hypercholesterolemia and breast cancer pathophysiology. Science 2013;342(6162):1094-8.
Network, Comprehensive molecular portraits of human breast tumours. Nature 490, 61-70, 2012.
Ouzounova et al., Monocytic and granulocytic myeloid derived suppressor cells differentially regulate spatiotemporal tumour plasticity during metastatic cascade. Nature communications 8, 14979, 2017.
Pan et al., Death domain-associated protein DAXX promotes ovarian cancer development and chemoresistance. J Biol Chem 288, 13620-13630, 2013.
Pandyra et al., Genome-wide RNAi analysis reveals that simultaneous inhibition of specific mevalonate pathway genes potentiates tumor cell death. Oncotarget 2015;6(29):26909-21.
Pavlova et al., The Emerging Hallmarks of Cancer Metabolism. Cell metabolism 23, 27-47, 2016.
Porstmann et al., SREBP activity is regulated by mTORC1 and contributes to Aktdependent cell growth. Cell metabolism 8, 224-236, 2008.
Puto et al., Daxx represses RelB target promoters via DNA methyltransferase recruitment and DNA hypermethylation. Genes Dev 22, 998-1010, 2008.
Puto et al., Transcriptional Repressor DAXX Promotes Prostate Cancer Tumorigenicity via Suppression of Autophagy. J Biol Chem 290, 15406-15420, 2015.
Puto et al., The DAXX co-repressor is directly recruited to active regulatory elements genome-wide to regulate autophagy programs in a model of human prostate cancer. Oncoscience 2, 362-372, 2015.
Ravnskov et al., Statins do not protect against cancer: quite the opposite. J Clin Oncol 33, 810-811, 2015.
Ricoult et al., Oncogenic PI3K and K-Ras stimulate de novo lipid synthesis through mTORC1 and SREBP. Oncogene 35, 1250-1260, 2016.
Rios-Esteves et al., Stearoyl CoA desaturase is required to produce active, lipid-modified Wnt proteins. Cell reports 4, 1072-1081, 2013.
Rohrig et al., The multifaceted roles of fatty acid synthesis in cancer. Nat Rev Cancer advance online publication, 2016.
Ru et al., Feedback Loop Regulation of SCAP/SREBP-1 by miR-29 Modulates EGFR Signaling-Driven Glioblastoma Growth. Cell reports 16, 1527-1535, 2016.
Ruggero et al., Does the ribosome translate cancer? Nat Rev Cancer 3, 179-192, 2003.
Santiago et al., Identification of two independent SUMO-interacting motifs in Daxx: evolutionary conservation from *Drosophila* to humans and their biochemical functions. Cell Cycle 8, 76-87, 2009.
Santos et al., Lipid metabolism in cancer. Febs J 279, 2610-2623, 2012.

(Continued)

*Primary Examiner* — Sudhakar Katakam
(74) *Attorney, Agent, or Firm* — Thomas | Horstemeyer, LLP

(57) ABSTRACT

Disclosed herein is a method for treating cancer in a subject that involves administering to the subject a therapeutically effective amount of a composition comprising a polypeptide that comprises an amino acid sequence corresponding to the C-terminal SUMO-interacting motif (SIM2) of a DAXX protein. The disclosed polypeptide is not a functional DAXX protein but competes with endogenous DAXX for binding to SUMO.

6 Claims, 81 Drawing Sheets

Specification includes a Sequence Listing.

(56) References Cited

PUBLICATIONS

Schug et al., Acetyl-CoA synthetase 2 promotes acetate utilization and maintains cancer cell growth under metabolic stress. Cancer Cell 27, 57-71, 2015.
Seo et al., Genome-wide localization of SREBP-2 in hepatic chromatin predicts a role in autophagy. Cell metabolism 13, 367-375, 2011.
Shaitelman et al., Impact of Statin Use on Outcomes in Triple Negative Breast Cancer. J Cancer 2017;8(11):2026-32.
Shao et al., Expanding roles for SREBP in metabolism. Cell metabolism 16, 414-419, 2012.
Simigdala et al., Cholesterol biosynthesis pathway as a novel mechanism of resistance to estrogen deprivation in estrogen receptor-positive breast cancer. Breast Cancer Res 2016;18(1):58.
Sundqvist et al., Control of lipid metabolism by phosphorylation-dependent degradation of the SREBP family of transcription factors by SCF(Fbw7). Cell metabolism 1, 379-391, 2005.
Tang et al., A joint analysis of metabolomics and genetics of breast cancer. Breast Cancer Res 16, 415, 2014.
Treuter et al., Transcriptional control of metabolic and inflammatory pathways by nuclear receptor SUMOylation. Biochim Biophys Acta 1812, 909-918, 2011.
Tzeng et al., Physiological and functional interactions between Tcf4 and Daxx in colon cancer cells. J Biol Chem 281, 15405-15411, 2006.
Wang et al., Transcriptional regulation of hepatic lipogenesis. Nat Rev Mol Cell Biol 16, 678-689, 2015.
Wang et al., Phosphorylation and recruitment of BAF60c in chromatin remodeling for lipogenesis in response to insulin. Mol Cell 49, 283-297, 2013.
Wang et al. Simvastatin-induced breast cancer cell death and deactivation of PI3K/Akt and MAPK/ERK signalling are reversed by metabolic products of the mevalonate pathway. Oncotarget 2016;7(3):2532-44.
Welcker et al., Fbw7 dimerization determines the specificity and robustness of substrate degradation. Genes Dev 27, 2531-2536, 2013.
Yang et al., Daxx, a Novel Fas-Binding Protein that Activates JNK and Apoptosis. Cell 89, 1067-1076, 1997.
Zhao et al., Negative regulation of p53 functions by Daxx and the involvement of MDM2. J Biol Chem 279, 50566-50579, 2004.
Altman et al., From Krebs to clinic: glutamine metabolism to cancer therapy. Nat Rev Cancer 16, 619-634, 2016.
Arito et al., Growth factor-induced phosphorylation of sterol regulatory element-binding proteins inhibits sumoylation, thereby stimulating the expression of their target genes, low density lipoprotein uptake, and lipid synthesis. J Biol Chem 283, 15224-15231, 2008.
Baek et al., The cholesterol metabolite 27 hydroxycholesterol facilitates breast cancer metastasis through its actions on immune cells. Nat Commun 2017;8(1):864.
Baumann et al., Lipid biology of breast cancer. Biochim Biophys Acta 1831, 1509-1517, 2013.
Becares et al., Posttranslational Modifications of Lipid-Activated Nuclear Receptors: Focus on Metabolism. Endocrinology 158, 213-225, 2017.
Beloribi-Djefaflia et al., Lipid metabolic reprogramming in cancer cells. Oncogenesis 5, e189, 2016.
Bengoechea-Alonso et al., SREBP in signal transduction: cholesterol metabolism and beyond. Curr Opin Cell Biol 19, 215-222, 2007.
Benitez et al., PTEN regulates glioblastoma oncogenesis through chromatinassociated complexes of DAXX and histone H3.3. Nature communications 8, 15223, 2017.
Boroughs et al., Metabolic pathways promoting cancer cell survival and growth. Nat Cell Biol 17, 351-359, 2015.
Boyd et al., Evidence of association between plasma high-density lipoprotein cholesterol and risk factors for breast cancer. J Natl Cancer Inst 1990;82(6):460-8.

Brown et al., Squalene epoxidase is a bona fide oncogene by amplification with clinical relevance in breast cancer. Scientific Reports 6, 2016.
Bulusu et al., Acetate Recapturing by Nuclear Acetyl-CoA Synthetase 2 Prevents Loss of Histone Acetylation during Oxygen and Serum Limitation. Cell reports 18, 647-658, 2017.
Chang et al., Structural and functional roles of Daxx SIM phosphorylation in SUMO paralog-selective binding and apoptosis modulation. Mol Cell 42, 62-74, 2011.
Chin et al., High-resolution aCGH and expression profiling identifies a novel genomic subtype of ER negative breast cancer. Genome Biol 8, R215, 2007.
Clendening et al., Targeting tumor cell metabolism with statins. Oncogene 31, 4967-4978, 2012.
Comerford et al., Acetate dependence of tumors. Cell 159, 1591-1602, 2014.
Croxton et al., Daxx represses expression of a subset of antiapoptotic genes regulated by nuclear factor-kappaB. Cancer Res 66, 9026-9035, 2006.
Di, Strategic approaches to optimizing peptide ADME properties. AAPS J 17, 134-143, 2015.
Drane et al., The death-associated protein DAXX is a novel histone chaperone involved in the replication-independent deposition of H3.3. Genes Dev 24, 1253-1265, 2010.
Elsasser et al., DAXX envelops a histone H3.3-H4 dimer for H3.3-specific recognition. Nature 491, 560-565, 2012.
Escobar-Cabrera et al., Structural characterization of the DAXX N-terminal helical bundle domain and its complex with Rassf1C. Structure 18, 1642-1653, 2010.
Fosgerau et al., Peptide therapeutics: current status and future directions. Drug Discov Today 20, 122-128, 2015.
Freed-Pastor et al., Mutant p53 disrupts mammary tissue architecture via the mevalonate pathway. Cell 2012;148(1-2):244-58.
Gao et al., Acetate functions as an epigenetic metabolite to promote lipid synthesis under hypoxia. Nature communications 7, 11960, 2016.
Goldberg et al., Distinct factors control histone variant H3.3 localization at specific genomic regions. Cell 140, 678-691, 2010.
Goldstein et al., A century of cholesterol and coronaries: from plaques to genes to statins. Cell 161, 161-172, 2015.
Gouw et al., Oncogene KRAS activates fatty acid synthase, resulting in specific ERK and lipid signatures associated with lung adenocarcinoma. Proc Natl Acad Sci U S A 114, 4300-4305, 2017.
Griffiths et al., Sterol regulatory element binding protein-dependent regulation of lipid synthesis supports cell survival and tumor growth. Cancer Metab 1, 3, 2013.
Guo et al., EGFR signaling through an Akt-SREBP-1-dependent, rapamycin-resistant pathway sensitizes glioblastomas to antilipogenic therapy. Science signaling 2, ra82, 2009.
Heinz S, et al. Mol Cell 2010 38(4):576-89.
Hirano et al, Sterol regulatory elementbinding proteins are negatively regulated through SUMO-1 modification independent of the ubiquitin/26 S proteasome pathway. J Biol Chem 278, 16809-16819, 2003.
Huang et al., Daxx positively modulates beta-catenin/TCF4-mediated transcriptional potential. Biochem Biophys Res Commun 386, 762-768, 2009.
Kambach et al., Disabled cell density sensing leads to dysregulated cholesterol synthesis in glioblastoma. Oncotarget 8, 2017.
Kaur et al., A mouse model for triple-negative breast cancer tumor-initiating cells (TNBC-TICs) exhibits similar aggressive phenotype to the human disease. BMC Cancer 12, 120, 2012.
Kim et al., A dysregulated acetyl/SUMO switch of FXR promotes hepatic inflammation in obesity. EMBO J 34, 184-199, 2015.
Kuzu et al., The Role of Cholesterol in Cancer. Cancer Research 76, 2063-2070, 2016.
Lee et al., PIASy-mediated sumoylation of SREBP1c regulates hepatic lipid metabolism upon fasting signaling. Mol Cell Biol 34, 926-938, 2014.
Lewis et al., SREBP maintains lipid biosynthesis and viability of cancer cells under lipid- and oxygen-deprived conditions and defines a gene signature associated with poor survival in glioblastoma multiforme. Oncogene 34, 5128-5140, 2015.

(56) References Cited

PUBLICATIONS

Lewis et al., Daxx is an H3.3-specific histone chaperone and cooperates with ATRX in replication-independent chromatin assembly at telomeres. Proc Natl Acad Sci U S A 107, 14075-14080, 2010.

Li et al., Inhibition of mTOR complex 2 induces GSK3/FBXW7-dependent degradation of sterol regulatory element-binding protein 1 (SREBP1) and suppresses lipogenesis in cancer cells. Oncogene 35, 642-650, 2016.

Li et al., EAP1/Daxx interacts with ETS1 and represses transcriptional activation of ETS1 target genes. Oncogene 19, 745-753, 2000.

Lin et al., Role of SUMO-interacting motif in Daxx SUMO modification, subnuclear localization, and repression of sumoylated transcription factors. Mol Cell 24, 341-354, 2006.

Lin et al., Daxx and TCF4 interaction links to oral squamous cell carcinoma growth by promoting cell cycle progression via induction of cyclin D1 expression. Clin Oral Investig 20, 533-540, 2016.

Liu et al., Structure of the variant histone H3.3-H4 heterodimer in complex with its chaperone DAXX. Nat Struct Mol Biol 19, 1287-1292, 2012.

Menendez et al., Fatty acid synthase and the lipogenic phenotype in cancer pathogenesis. Nat Rev Cancer 7, 763-777, 2007.

Michaelson et al., Loss of Daxx, a promiscuously interacting protein, results in extensive apoptosis in early mouse development. Genes Dev 13, 1918-1923, 1999.

Migita, T. et al. Fatty acid synthase: a metabolic enzyme and candidate oncogene in prostate cancer. J Natl Cancer Inst 101, 519-532, 2009.

Mishra et al., Metabolic Signatures of Human Breast Cancer. Mol Cell Oncol 2, 2015.

Mudduluru et al., Repositioning of drugs for intervention in tumor progression and metastasis: Old drugs for new targets. Drug Resist Updat 26, 10-27, 2016.

Mullen et al., The interplay between cell signalling and the mevalonate pathway in cancer. Nat Rev Cancer 2016; advance online publication.

\* cited by examiner

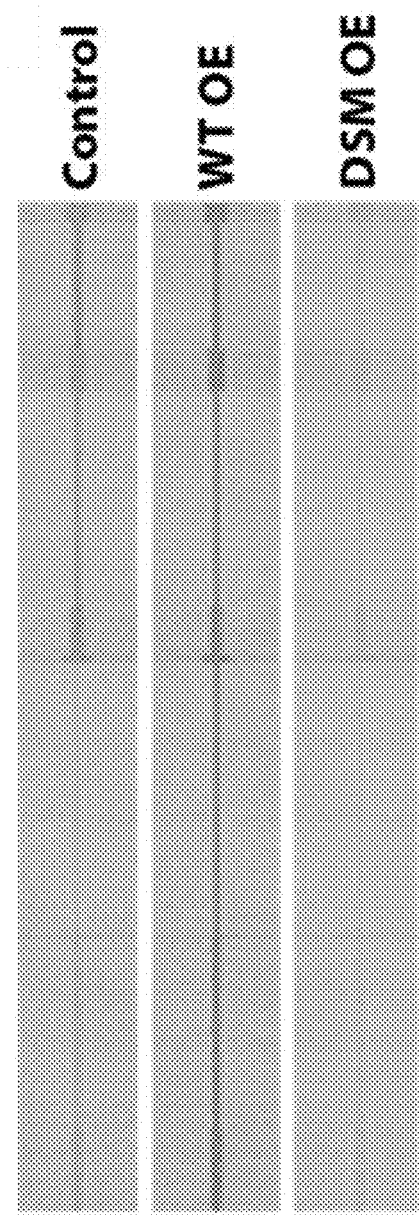
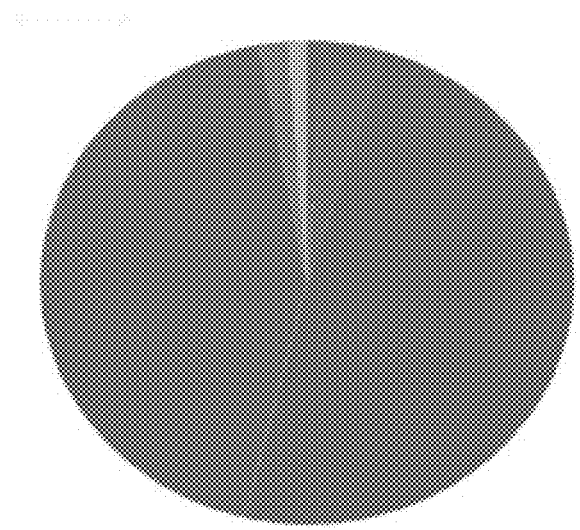
- 3' UTR (1%)
- 5' UTR (0%)
- Exon (6%)
- Intergenic (47%)
- Intron (40%)
- Promoter-TSS (4%)
- TSS (2%)
FIG. 3C
FIG. 3D

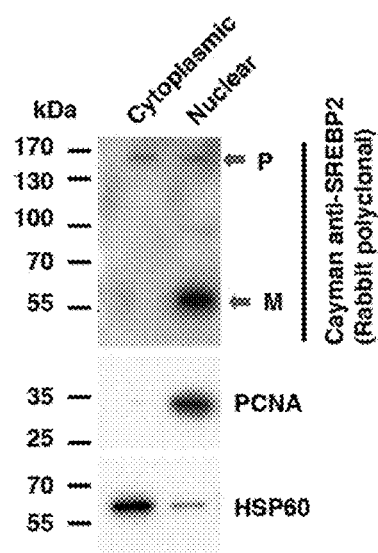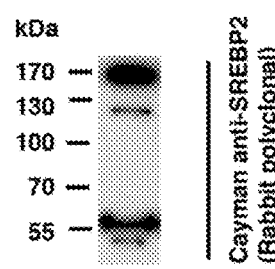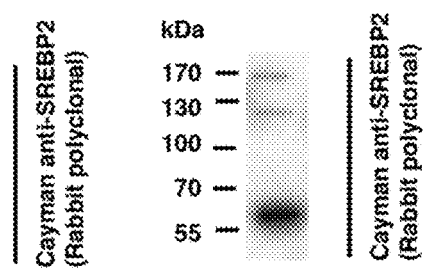
FIG. 12B
FIG. 12C

FIG. 14A

SEQUENCE LISTING

```
Sequence total quantity: 64
SEQ ID NO: 1            moltype = AA  length = 12
FEATURE                 Location/Qualifiers
source                  1..12
                        mol_type = protein
                        organism = synthetic construct
SEQUENCE: 1
DPEEIIVLSD SD                                                           12

SEQ ID NO: 2            moltype = AA  length = 12
FEATURE                 Location/Qualifiers
source                  1..12
                        mol_type = protein
                        organism = synthetic construct
SEQUENCE: 2
DPDDIIVLSD SD                                                           12

SEQ ID NO: 3            moltype = AA  length = 12
FEATURE                 Location/Qualifiers
source                  1..12
                        mol_type = protein
                        organism = synthetic construct
SEQUENCE: 3
DPEEIIVLSE SE                                                           12

SEQ ID NO: 4            moltype = AA  length = 12
FEATURE                 Location/Qualifiers
source                  1..12
                        mol_type = protein
                        organism = synthetic construct
SEQUENCE: 4
DPEEIIVLDD DD                                                           12

SEQ ID NO: 5            moltype = AA  length = 12
FEATURE                 Location/Qualifiers
source                  1..12
                        mol_type = protein
                        organism = synthetic construct
SEQUENCE: 5
DPEEKIVLSD SD                                                           12

SEQ ID NO: 6            moltype = AA  length = 12
FEATURE                 Location/Qualifiers
source                  1..12
                        mol_type = protein
                        organism = synthetic construct
SEQUENCE: 6
DPEEIIDLSD SD                                                           12

SEQ ID NO: 7            moltype = AA  length = 12
FEATURE                 Location/Qualifiers
```

```
source                   1..12
                         mol_type = protein
                         organism = synthetic construct
SEQUENCE: 7
EPEEIIVLSD SD                                                                    12

SEQ ID NO: 8             moltype = AA  length = 7
FEATURE                  Location/Qualifiers
source                   1..7
                         mol_type = protein
                         organism = synthetic construct
SEQUENCE: 8
IIVLSDS                                                                           7

SEQ ID NO: 9             moltype =   length =
SEQUENCE: 9
000

SEQ ID NO: 10            moltype =   length =
SEQUENCE: 10
000

SEQ ID NO: 11            moltype = AA  length = 10
FEATURE                  Location/Qualifiers
REGION                   1..2
                         note = MISC_FEATURE - Xaa is Asp, Glu, Ser, or Thr
REGION                   7..10
                         note = MISC_FEATURE - Xaa is Asp, Glu, Ser, or Thr
source                   1..10
                         mol_type = protein
                         organism = synthetic construct
SEQUENCE: 11
XXIIVLXXXX                                                                       10

SEQ ID NO: 12            moltype = DNA  length = 23
FEATURE                  Location/Qualifiers
source                   1..23
                         mol_type = other DNA
                         organism = synthetic construct
SEQUENCE: 12
gctcctcctg agcgcaagta ctc                                                        23

SEQ ID NO: 13            moltype = DNA  length = 20
FEATURE                  Location/Qualifiers
source                   1..20
                         mol_type = other DNA
                         organism = synthetic construct
SEQUENCE: 13
gtggacagcg aggccaggat                                                            20

SEQ ID NO: 14            moltype = DNA  length = 20
FEATURE                  Location/Qualifiers
source                   1..20
                         mol_type = other DNA
                         organism = synthetic construct
SEQUENCE: 14
gaggcgtctc tcctcacaac                                                            20

SEQ ID NO: 15            moltype = DNA  length = 20
FEATURE                  Location/Qualifiers
source                   1..20
                         mol_type = other DNA
                         organism = synthetic construct
SEQUENCE: 15
tctcatgcac tgacctttgc                                                            20

SEQ ID NO: 16            moltype = DNA  length = 20
FEATURE                  Location/Qualifiers
source                   1..20
                         mol_type = other DNA
                         organism = synthetic construct
SEQUENCE: 16
ctgctgtcca caaaagcaaa                                                            20

SEQ ID NO: 17            moltype = DNA  length = 20
FEATURE                  Location/Qualifiers
source                   1..20
                         mol_type = other DNA
                         organism = synthetic construct
```

```
SEQUENCE: 17
ggtcagtgtg tcctccacct                                                        20

SEQ ID NO: 18           moltype = DNA   length = 20
FEATURE                 Location/Qualifiers
source                  1..20
                        mol_type = other DNA
                        organism = synthetic construct
SEQUENCE: 18
atcgctcctc catcaatgac                                                        20

SEQ ID NO: 19           moltype = DNA   length = 20
FEATURE                 Location/Qualifiers
source                  1..20
                        mol_type = other DNA
                        organism = synthetic construct
SEQUENCE: 19
ttcctcagaa cgccagactt                                                        20

SEQ ID NO: 20           moltype = DNA   length = 20
FEATURE                 Location/Qualifiers
source                  1..20
                        mol_type = other DNA
                        organism = synthetic construct
SEQUENCE: 20
cacagggaca acctggagtt                                                        20

SEQ ID NO: 21           moltype = DNA   length = 20
FEATURE                 Location/Qualifiers
source                  1..20
                        mol_type = other DNA
                        organism = synthetic construct
SEQUENCE: 21
actccacagg tgggaacaag                                                        20

SEQ ID NO: 22           moltype = DNA   length = 20
FEATURE                 Location/Qualifiers
source                  1..20
                        mol_type = other DNA
                        organism = synthetic construct
SEQUENCE: 22
accaccaatg ccaaagtagc                                                        20

SEQ ID NO: 23           moltype = DNA   length = 20
FEATURE                 Location/Qualifiers
source                  1..20
                        mol_type = other DNA
                        organism = synthetic construct
SEQUENCE: 23
ctgcaggttc tcaatgcaaa                                                        20

SEQ ID NO: 24           moltype = DNA   length = 20
FEATURE                 Location/Qualifiers
source                  1..20
                        mol_type = other DNA
                        organism = synthetic construct
SEQUENCE: 24
tgttcgttgc cactttcttg                                                        20

SEQ ID NO: 25           moltype = DNA   length = 20
FEATURE                 Location/Qualifiers
source                  1..20
                        mol_type = other DNA
                        organism = synthetic construct
SEQUENCE: 25
gggggctaat gttcttgtca                                                        20

SEQ ID NO: 26           moltype = DNA   length = 20
FEATURE                 Location/Qualifiers
source                  1..20
                        mol_type = other DNA
                        organism = synthetic construct
SEQUENCE: 26
gcgaaagaaa cgagttccag                                                        20

SEQ ID NO: 27           moltype = DNA   length = 20
FEATURE                 Location/Qualifiers
source                  1..20
                        mol_type = other DNA
```

```
SEQUENCE: 27
tgacagacaa gcacgtctcc                                        20

SEQ ID NO: 28          moltype = DNA  length = 20
FEATURE                Location/Qualifiers
source                 1..20
                       mol_type = other DNA
                       organism = synthetic construct
SEQUENCE: 28
tgctttggtt gtgcagtcat                                        20

SEQ ID NO: 29          moltype = DNA  length = 20
FEATURE                Location/Qualifiers
source                 1..20
                       mol_type = other DNA
                       organism = synthetic construct
SEQUENCE: 29
ttccaaatgg agcctgaaac                                        20

SEQ ID NO: 30          moltype = DNA  length = 20
FEATURE                Location/Qualifiers
source                 1..20
                       mol_type = other DNA
                       organism = synthetic construct
SEQUENCE: 30
tacgctgatc acgcagtttc                                        20

SEQ ID NO: 31          moltype = DNA  length = 20
FEATURE                Location/Qualifiers
source                 1..20
                       mol_type = other DNA
                       organism = synthetic construct
SEQUENCE: 31
tgacgcctcc tgagaaaaat                                        20

SEQ ID NO: 32          moltype = DNA  length = 20
FEATURE                Location/Qualifiers
source                 1..20
                       mol_type = other DNA
                       organism = synthetic construct
SEQUENCE: 32
catgccagtg ctaaagtgga                                        20

SEQ ID NO: 33          moltype = DNA  length = 20
FEATURE                Location/Qualifiers
source                 1..20
                       mol_type = other DNA
                       organism = synthetic construct
SEQUENCE: 33
tactccaagg ccaaaaccac                                        20

SEQ ID NO: 34          moltype = DNA  length = 20
FEATURE                Location/Qualifiers
source                 1..20
                       mol_type = other DNA
                       organism = synthetic construct
SEQUENCE: 34
gggacacata tgcaacatgc                                        20

SEQ ID NO: 35          moltype = DNA  length = 20
FEATURE                Location/Qualifiers
source                 1..20
                       mol_type = other DNA
                       organism = synthetic construct
SEQUENCE: 35
cactgggcat ggatctttt                                         20

SEQ ID NO: 36          moltype = DNA  length = 20
FEATURE                Location/Qualifiers
source                 1..20
                       mol_type = other DNA
                       organism = synthetic construct
SEQUENCE: 36
gtcattccag ccaaggttgt                                        20

SEQ ID NO: 37          moltype = DNA  length = 20
FEATURE                Location/Qualifiers
source                 1..20
```

```
                        mol_type = other DNA
                        organism = synthetic construct
SEQUENCE: 37
catggcagag cccactaaat                                              20

SEQ ID NO: 38           moltype = DNA  length = 20
FEATURE                 Location/Qualifiers
source                  1..20
                        mol_type = other DNA
                        organism = synthetic construct
SEQUENCE: 38
ggcgagttgc taagaaaacg                                              20

SEQ ID NO: 39           moltype = DNA  length = 20
FEATURE                 Location/Qualifiers
source                  1..20
                        mol_type = other DNA
                        organism = synthetic construct
SEQUENCE: 39
ccctgggcgt atatggtcta                                              20

SEQ ID NO: 40           moltype = DNA  length = 20
FEATURE                 Location/Qualifiers
source                  1..20
                        mol_type = other DNA
                        organism = synthetic construct
SEQUENCE: 40
gtctccggaa agcagctatg                                              20

SEQ ID NO: 41           moltype = DNA  length = 20
FEATURE                 Location/Qualifiers
source                  1..20
                        mol_type = other DNA
                        organism = synthetic construct
SEQUENCE: 41
cagtggagca tggagttcct                                              20

SEQ ID NO: 42           moltype = DNA  length = 20
FEATURE                 Location/Qualifiers
source                  1..20
                        mol_type = other DNA
                        organism = synthetic construct
SEQUENCE: 42
attgacttgt ggtggcatga                                              20

SEQ ID NO: 43           moltype = DNA  length = 20
FEATURE                 Location/Qualifiers
source                  1..20
                        mol_type = other DNA
                        organism = synthetic construct
SEQUENCE: 43
ctgtgtgaac cacacccttg                                              20

SEQ ID NO: 44           moltype = DNA  length = 20
FEATURE                 Location/Qualifiers
source                  1..20
                        mol_type = other DNA
                        organism = synthetic construct
SEQUENCE: 44
tgccgactac atctgcaaag                                              20

SEQ ID NO: 45           moltype = DNA  length = 20
FEATURE                 Location/Qualifiers
source                  1..20
                        mol_type = other DNA
                        organism = synthetic construct
SEQUENCE: 45
ggttcagcaa ggtcagcttc                                              20

SEQ ID NO: 46           moltype = DNA  length = 20
FEATURE                 Location/Qualifiers
source                  1..20
                        mol_type = other DNA
                        organism = synthetic construct
SEQUENCE: 46
tgattcgcaa acttcccttc                                              20

SEQ ID NO: 47           moltype = DNA  length = 20
FEATURE                 Location/Qualifiers
```

```
source                      1..20
                            mol_type = other DNA
                            organism = synthetic construct
SEQUENCE: 47
gtcttcaaaa aggccaacca                                                    20

SEQ ID NO: 48               moltype = DNA   length = 20
FEATURE                     Location/Qualifiers
source                      1..20
                            mol_type = other DNA
                            organism = synthetic construct
SEQUENCE: 48
gcccagtgtt tcttctgctt                                                    20

SEQ ID NO: 49               moltype = DNA   length = 20
FEATURE                     Location/Qualifiers
source                      1..20
                            mol_type = other DNA
                            organism = synthetic construct
SEQUENCE: 49
tctccgcagt ttcctcaaat                                                    20

SEQ ID NO: 50               moltype = DNA   length = 20
FEATURE                     Location/Qualifiers
source                      1..20
                            mol_type = other DNA
                            organism = synthetic construct
SEQUENCE: 50
agtagacaag ccagccagga                                                    20

SEQ ID NO: 51               moltype = DNA   length = 20
FEATURE                     Location/Qualifiers
source                      1..20
                            mol_type = other DNA
                            organism = synthetic construct
SEQUENCE: 51
gtactgctgc tggagccttc                                                    20

SEQ ID NO: 52               moltype = DNA   length = 20
FEATURE                     Location/Qualifiers
source                      1..20
                            mol_type = other DNA
                            organism = synthetic construct
SEQUENCE: 52
tagagggagc cagagagacg                                                    20

SEQ ID NO: 53               moltype = DNA   length = 19
FEATURE                     Location/Qualifiers
source                      1..19
                            mol_type = other DNA
                            organism = synthetic construct
SEQUENCE: 53
gctgctcgta cctggtgag                                                     19

SEQ ID NO: 54               moltype = DNA   length = 20
FEATURE                     Location/Qualifiers
source                      1..20
                            mol_type = other DNA
                            organism = synthetic construct
SEQUENCE: 54
caagggaaat tgaggctgag                                                    20

SEQ ID NO: 55               moltype = DNA   length = 20
FEATURE                     Location/Qualifiers
source                      1..20
                            mol_type = other DNA
                            organism = synthetic construct
SEQUENCE: 55
cgttccagga gcatctgatt                                                    20

SEQ ID NO: 56               moltype = DNA   length = 20
FEATURE                     Location/Qualifiers
source                      1..20
                            mol_type = other DNA
                            organism = synthetic construct
SEQUENCE: 56
actgttggga gggaacctct                                                    20

SEQ ID NO: 57               moltype = DNA   length = 20
```

```
FEATURE                 Location/Qualifiers
source                  1..20
                        mol_type = other DNA
                        organism = synthetic construct
SEQUENCE: 57
cccctctgct ctcaaacaag                                               20

SEQ ID NO: 58           moltype = DNA  length = 20
FEATURE                 Location/Qualifiers
source                  1..20
                        mol_type = other DNA
                        organism = synthetic construct
SEQUENCE: 58
gtgaaccatg actgcaccac                                               20

SEQ ID NO: 59           moltype = DNA  length = 20
FEATURE                 Location/Qualifiers
source                  1..20
                        mol_type = other DNA
                        organism = synthetic construct
SEQUENCE: 59
gagccctcgg tgacatacat                                               20

SEQ ID NO: 60           moltype = DNA  length = 20
FEATURE                 Location/Qualifiers
source                  1..20
                        mol_type = other DNA
                        organism = synthetic construct
SEQUENCE: 60
tcatggccaa actgttgaaa                                               20

SEQ ID NO: 61           moltype = DNA  length = 20
FEATURE                 Location/Qualifiers
source                  1..20
                        mol_type = other DNA
                        organism = synthetic construct
SEQUENCE: 61
tggggtccat tgtttctgat                                               20

SEQ ID NO: 62           moltype = DNA  length = 44
FEATURE                 Location/Qualifiers
source                  1..44
                        mol_type = other DNA
                        organism = synthetic construct
SEQUENCE: 62
cagctgaagc ttgcatgcct gcaggtaggc agctgggaag atga                    44

SEQ ID NO: 63           moltype = DNA  length = 44
FEATURE                 Location/Qualifiers
source                  1..44
                        mol_type = other DNA
                        organism = synthetic construct
SEQUENCE: 63
gagtatatat aggactgggg atccgtgagg gtctccatgg tctc                    44

SEQ ID NO: 64           moltype = DNA  length = 19
FEATURE                 Location/Qualifiers
source                  1..19
                        mol_type = other DNA
                        organism = synthetic construct
SEQUENCE: 64
ggagttggat ctctcagaa                                                19
```

POLYPEPTIDE INHIBITOR OF DE NOVO LIPOGENESIS IN CANCER CELLS

CROSS-REFERENCE TO RELATED APPLICATIONS

This application is a divisional of U.S. application Ser. No. 17/044,547, filed Oct. 1, 2020, which is a National Stage of International Application No. PCT/US2019/026011, filed Apr. 5, 2019, which claims benefit of U.S. Provisional Application No. 62/653,183, filed Apr. 5, 2018, all of which are hereby incorporated herein by reference in their entireties.

SEQUENCE LISTING

This application contains a sequence listing filed in ST.26 format entitled "222107-1076 Sequence Listing" created on Sep. 26, 2023, having 56,544 bytes. The content of the sequence listing is incorporated herein in its entirety.

BACKGROUND

Cancer cells exhibit elevated de novo intracellular lipogenesis, resulting in increased levels of fatty acids, membrane phospholipids, and cholesterol (Menendez, J. A. & Lupu, R. Nat Rev Cancer 7:763-777 (2007); Santos, C. R. & Schulze, A. Febs J 279:2610-2623 (2012); Mishra, P. & Ambs, S. Mol Cell Oncol 2 (2015); Migita, T. et al. J Natl Cancer Inst 101:519-532 (2009)). Notably, de novo lipogenesis only contributes minimally to the overall lipid content of normal non-proliferating cells, which generally rely on the uptake of lipids from the circulation. Increased de novo lipogenesis in cancer cells is required to supply lipids for the synthesis of membrane and signaling molecules during rapid cell proliferation and tumor growth, due to limited availability of lipids from the circulation in the tumor microenvironment (Santos, C. R. & Schulze, A. Febs J 279:2610-2623 (2012); Beloribi-Djefaflia, S., et al. Oncogenesis 5:e189 (2016); Lewis, C. A. et al. Oncogene 34:5128-5140 (2015); Baumann, J., et al. Biochim Biophys Acta 1831: 1509-1517 (2013); Rios-Esteves, J., et al. Cell reports 4:1072-1081 (2013); Pavlova, N. N. & Thompson, C. B. Cell metabolism 23:27-47 (2016); Boroughs, L. K. & DeBerardinis, R. J. Nat Cell Biol 17:351-359 (2015)). Because of heightened intracellular lipogenesis in cancer, it has been widely reported that drugs that inhibit lipogenesis may have anticancer potential (Mishra, P. & Ambs, S. Mol Cell Oncol 2 (2015); Mudduluru, G., et al. Drug Resist Updat 26:10-27 (2016); Kuzu, O. F., et al. Cancer Research 76:2063-2070 (2016); Kambach, D. M. et al. Oncotarget 8:14860-14875 (2017)). Indeed, numerous completed and active clinical trials have tested statins, which inhibit HMG-CoA reductase and lower blood cholesterol levels, for cancer prevention and treatment (Mudduluru, G., et al. Drug Resist Updat 26:10-27 (2016)). However, it remains controversial as to whether statins provide benefits for cancer prevention or treatment (Mudduluru, G., et al. Drug Resist Updat 26:10-27 (2016); Clendening, J. W. & Penn, L. Z. Oncogene 31:4967-4978 (2012); Ravnskov, U., et al. J Clin Oncol 33:810-811 (2015)). The lack of clear effects of statins on cancer in clinical studies highlights the need to clearly understand the mechanisms that control de novo lipogenesis in cancer cells and to identify biomarkers that can predict treatment responses to statins and the development of potential new agents targeting the lipogenesis pathway for effective cancer therapy.

Lipogenesis is controlled by sterol regulatory element-binding proteins, SREBP1 and SREBP2, that have also been shown to play a critically important role in maintaining lipid synthesis in cancer (Griffiths, B. et al. Cancer Metab 1:3 (2013)). SREBP1/2 precursors are sequestered in endoplasmic reticulum (ER). When sterol supply is low, SREBP1/2 are transported to the Golgi apparatus where they are cleaved by proteases, and the N-terminal domain of SREBPs are then released and imported into the nucleus to activate genes that contain the sterol regulatory element (SRE) required for lipogenesis. Oncogenic drivers such as KRAS, P13K and mTOR signaling have been shown to promote de novo lipogenesis in breast and other cancer types (Ricoult, S. J. et al. Oncogene 35:1250-1260 (2016); Ru, P. et al. Cell reports 16:1527-1535 (2016); Guo, D. et al. Science signaling 2:ra82 (2009)). mTOR signaling apparently promotes lipogenesis through stabilizing SREBP1 and SREBP2 by opposing phosphorylation-dependent poly-ubiquitination of SREBP1/2 by the E3 ubiquitin ligase and tumor suppressor FBXW7 and subsequent proteasomal degradation (Sundqvist, A. et al. Cell metabolism 1:379-391 (2005); Welcker, M., et al. Genes Dev 27:2531-2536 (2013); Li, S., et al. Oncogene 35:642-650 (2016)). Notably, tumors efficiently convert acetate to acetyl-CoA (Comerford, S. A. et al. Cell 159:1591-1602 (2014); Schug, Z. T. et al. Cancer Cell 27:57-71 (2015)), which is predominantly used for lipid synthesis (Bulusu, V. et al. Cell reports 18:647-658 (2017)), highlighting the need for cancer cells to produce lipogenic enzymes (Gao, X., et al. Nature communications 7:11960 (2016)). While the dependence on de novo lipogenesis in cancer is well documented, the mechanisms that directly control SREBP-mediated transcription underlying de novo lipogenesis in cancer cells remain largely unknown.

SUMMARY

Genetic depletion of DAXX-encoding death domain-associated protein is shown herein to markedly downregulate the expression of key lipogenic regulators and impair de novo lipogenesis. DAXX interacts with sterol regulatory element-binding proteins (SREBP1 and SREBP2) and activates SREBP-mediated transcription and is associated with chromatins containing SREBP-binding cis-acting elements. SREBP2 knockdown markedly attenuates DAXX-mediated effects on lipogenesis, indicating that DAXX directly promotes the SREBP2 lipogenic pathway. Notably, the DAXX/SREBP2 axis also activates MYC expression. In vivo, DAXX depletion attenuates, while DAXX overexpression enhances, the growth of xenograft tumors. Strikingly, a DAXX mutant deficient of small ubiquitin-related modifier (SUMO)-binding fails to activate de novo lipogenesis, and this mutant is completely defective for stimulating tumor growth. Thus, DAXX's SUMO-binding property is critical for cancer lipogenesis program. Remarkably, a peptide derived from the C-terminal SUMO-interacting motif of DAXX (termed SIM2) is spontaneously cell-membrane permeable, inhibits de novo lipogenesis in cells and tumor growth in vivo, highlighting therapeutic potential of SIM2. These results establish DAXX as a key regulator of de novo lipogenesis and a therapeutic target for cancer therapy. Therefore, disclosed herein is a method for treating cancer in a subject that involves administering to the subject a therapeutically effective amount of a composition comprising a polypeptide that comprises an amino acid sequence corresponding to at the C-terminal SUMO-interacting motif (SIM2) of a DAXX protein. The disclosed polypeptide is not a functional DAXX protein but competes with endogenous DAXX for binding to SUMO.

DAXX has two SUMO interacting motifs (SIMs) that interact with SUMO. SIM1 is at the N-terminus, and SIM2 is at the C-terminus (aa 729-740 of human DAXX). Therefore, in some embodiments, the polypeptide comprises at least amino acids 729 to 740 of human DAXX protein, or a homologue or variant thereof that binds SUMO. In some embodiments, the polypeptide lacks amino acids 1 to 728 of the DAXX protein. In some embodiments, the polypeptide comprises or consists of the amino acid sequence DPEEIIVLSDSD (SEQ ID NO:1, SIM2), or a variant thereof, e.g. having one or two conservative amino acid substitutions, that binds SUMO-1. Therefore, in some embodiments, the polypeptide comprises or consists of an amino acid sequence selected from the group comprising DPDDIIVLSDSD (SEQ ID NO:2, SIM008), DPEEIIVLSESE (SEQ ID NO:3, SIM009), DPEEIIVLDDDD (SEQ ID NO:4, SIM010), DPEEKIVLSDSD (SEQ ID NO:5, SIM011), DPEEIIDLSDSD (SEQ ID NO:6, SIM012), EPEEIIVLSDSD (SEQ ID NO:7, SIM013), and IIVLSDS (SEQ ID NO:8, SIM014). In some embodiments, the polypeptide comprises the amino acid sequence $X_1PX_2X_3X_4X_5X_6X_7X_8X_9X_{10}X_{11}$ (SEQ ID NO:9), wherein $X_1$ is D or E, $X_2$ is E or D, $X_3$ is E or D, $X_4$ is I, V or L, $X_5$ is I, V, or L, $X_6$ is V, I, or L, $X_7$ is L, I, or V, $X_8$ is S, T, E or D, $X_9$ is D or E, $X_{10}$ is S, T, E or D, and $X_{11}$ is D or E.

In some embodiments, the polypeptide comprises the amino acid sequence $X_1X_2X_3X_4X_5X_6X_7X_8$ (SEQ ID NO:10), wherein $X_1$ is S, T, D or E, $X_2$ is S, T, D, or E, $X_3$ is I, V or L, $X_4$ is I, V, or L, $X_5$ is V, I, or L, $X_6$ is L, I, or V, $X_7$ is S, T, E or D, $X_8$ is S, T, D or E.

In some embodiments, the polypeptide comprises the amino acid sequence XXIIVLXXXX (SEQ ID NO:11), wherein X is D, E, S, or T.

The cancer of the disclosed methods can be any cell in a subject undergoing unregulated growth, invasion, or metastasis. In some aspects, the cancer is breast cancer, prostate cancer, or colon cancer. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed polypeptides can be used in combination with any compound, moiety or group which has a cytotoxic or cytostatic effect. Drug moieties include chemotherapeutic agents, which may function as microtubule inhibitors, mitosis inhibitors, topoisomerase inhibitors, or DNA intercalators, and particularly those which are used for cancer therapy. The disclosed polypeptides can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Also disclosed is a composition comprising the disclosed polypeptide in a pharmaceutically acceptable excipient. For example, in some embodiments, the polypeptide is encapsulated in a biocompatible nanoparticle. In particular embodiments, the polypeptide is formulated in a vehicle containing a mixture of 2-Hydroxypropyl)-β-cyclodextrin (HPBCD) water solution and polyethylene glycols (e.g., PEG400).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows validation of shRNA-mediated DAXX knockdown (KD) and the overexpression of DAXX wt (WT) and the SUMO-binding defective mutant (DSM) compared to cells with a control vector (Control, CTL) in MDA-MB-231 and MDA-MB-468 cells by immunoblotting. Total cell lysates were prepared from cells cultured in the presence of 10% serum. FIG. 1B is a heatmap of select genes in the lipogenesis pathway in MDA-MB-231-derived cells (Control, KD and wt OE) based on microarray data (triplicates for each group). mRNAs for microarray analysis were isolated from cells cultured with 10% serum. FIG. 1C shows IPA pathway analysis based on mRNA microarray data as in panel B. Select downregulated metabolic pathways and upstream regulators repressed in DAXX KD cells compared to control cells (pathway activity z-scores<−2). FIG. 1D shows gene set enrichment analyses (GSEA) of cholesterol biosynthesis genes downregulated due to DAXX KD (left) or upregulated due to DAXX WT OE in MDA-MB-231 cells. The KEGG cholesterol biosynthesis geneset was used for the GSEA plots. FIG. 1E is a heatmap of select genes in the fatty acid and cholesterol biosynthesis pathways in MDA-MB-231-derived cells (control, KD, WT and DSM OE) based on RNA-seq data (average values of duplicate samples for each group). mRNAs for RNA-seq analysis were isolated from cells cultured with serum-free DMEM medium for 24 h. FIG. 1F shows IPA pathway analysis based on RNA-seq data as in panel E. Pathways with activity z scores<−2 are shown as in panel C. FIG. 1G shows impact of DAXX expression levels on acetate-dependent de novo lipid synthesis using [$^{14}$C] acetate labeling in the absence of serum in cell lines derived from MDA-MB-231 and MDA-MB-468. FIGS. 1H and 1I show principal component analysis (PCA) of lipidome in the panel of four MDA-MB-231 and MDA-MB-468-derived cell lines (control, KD, WT, and DSM). Levels of cholesterol and diacylglycerols in the indicated cell lines. GGPP: Geranylgeranyl diphosphate.

FIG. 2A shows the endogenous DAXX and SREBP2 interact. MDA-MB-231 or PC3 cell extracts were subjected to IP with a control (IgG) or an anti-DAXX monoclonal antibody. The immunoprecipitated SREBP2 was detected. P, precursor; M, mature SREBP2. FIGS. 2B, 2C, and 2D show there are two independent binding sites in DAXX for mature SREBP2. 293T cells were cotransfected with FLAG-SREBP2 (mature) and GFP or an indicated GFP-DAXX construct. The cell lysates were subjected to FLAG IP. Note that the DAXX amino acid (aa) 129-190 and 574-740 constructs are not recognized by the antibody used for detecting DAXX in (FIGS. 2B and 2D); these constructs were detected with a GFP antibody (FIGS. 2B and 2C, lane 2), or a mouse mAb recognizing a C-terminal epitope of DAXX (panel D, DAXX 574-740 part, lane 3). HC: IgG heavy chain. *: non-specific band. FIG. 2E is a schematic drawing of DAXX-SREBP2 interactions. The two independent SREBP2-binding sites are depicted. Also shown is the sequence of aa 327-335 within the DAXX HBD critical for the DAXX-SREBP2 interactions. SIM: SUMO-interacting motif; DHB: DAXX helical bundle; HBD: histone-binding domain; PEST: proline, glutamic acid, serine, and threonine-rich sequence. Numbers refer to aa residue positions in the DAXX protein. Note that the irrelevant lanes in the same blots (between the input and IP samples in the PC3 blot in panel A, between lanes 4 and 5, and lanes 12 and 13 in panel B, and between lanes 1 and 2 in panel D) are left out.

FIGS. 3A to 3F show DAXX activates SREBP-mediated transcription and occupies the promoters of lipogenic genes. FIG. 3A shows MDA-MB-231 cells were transfected with a luciferase reporter driven by a promoter fragment from the SREBF2 gene along with SREBP2, SREBP1a, SREBP1c, wt DAXX or the DSM mutant cDNA as indicated. Dual luciferase assays were done. FIGS. 3B-3F shows ChIP-seq analysis of genome-wide occupancy of DAXX. FIGS. 3B and 3C show ChIP-seq signal intensity plot (a comparison of the average DAXX ChIP-seq tag intensities) and heat maps in MDA-MB-231 control, wt OE, and DSM OE cell lines; signals are centralized to transcriptional start sites (TSS); FIG. 3D show the genome-wide distribution of DAXX chromatin occupancy; FIG. 3E shows motifs enriched as determined by the DAXX ChIP-seq dataset of MDA-MB-231 wt OE cells, and FIG. 3F shows occupancy of wt and the DSM mutant OE in select lipogenic genes based on ChIP-seq data.

FIGS. 4A and 4B show cell lines derived from MDA-MB-231 or MDA-MB-468 stably transduced with a control vector (Control), DAXX shRNA (KD), wt DAXX cDNA (WT OE), or the mutant defective of SUMO-binding (DSM OE) were implanted into mammary fat pads of female NSG mice. Longitudinal tumor volumes are plotted. Tumor images and weights at the endpoint are shown. FIG. 4C shows DAXX overexpression was maintained for both the WT and DSM mutant proteins. Protein extracts from three representative xenograft tumors were analyzed for DAXX protein levels using immunoblotting. HSP60 was detected as a loading control. FIG. 4D shows lipid profiles of xenograft tumors derived from MDA-MB-231 cell line panel as in FIG. 4A. Box plots of representative lipid species in tumor extracts are shown. The p values were calculated based on Student's t-test. *: p<0.05; : p<0.01; *: p<0.001. 25/27-HC: 25- or 27-hydroxycholesterol.

FIG. 5A shows cells derived from MDA-MB-231 cell line with a vector for a control, an SREBF2 shRNA, or SREBP2 (mature) cDNA were subjected to qRT-PCR for assessing SREBP2 expression, and de novo lipogenesis assays. FIGS. 5B and 5C show cells xenografted into mammary fat pads of female NSG mice. Tumor volumes were plotted against time (left). Representative images of dissected tumors are shown (middle). The final tumor weights are plotted. The p values were calculated (vs. control) based on Student's t-test. *: p<0.05; : p<0.01; *: p<0.001. For FIG. 5C, control or SREBP2 shRNA were expressed in MDA-MB-231 cells with wt DAXX OE. The levels of the indicated proteins were assessed by immunoblotting (left).

FIG. 6A shows GFP-DAXX constructs cotransfected with FLAG-SREBP2 into 293T cells. The GFP-wt DAXX was transfected alone in the absence of FLAG-SREBP2 as a control (lane 7). The lysates of transfected cells were subjected to IP with an anti-FLAG antibody. Both DAXX and FLAG-SREBP2 were detected in immunoprecipitates and input lysates. FIG. 6B shows dual luciferase assays of transfected 293T cells with the indicated reporter and other plasmids were conducted. FIG. 6C shows MDA-MB-231 cells stably expressing wt DAXX, and the DSM, S495A and S671A mutants were subjected to ChIP with a control IgG, anti-DAXX (5G11) and anti-FLAG (M2, all the DAXX constructs carrying an N-terminal FLAG tag). The precipitated DNAs were subjected to qPCR with primers specific to promoter regions of the indicated genes. qPCRs for the 3' UTR of the FASN and ACACA genes serve as negative control. FIG. 6D shows qRT-PCR analyses of the indicated genes in MDA-MB-231-derived cells (control, S671A and S495A) cultured in DMEM medium without serum for 24 h. ATRX qRT-PCR serves as a control for genes not regulated by SREBPs. FIG. 6E shows immunoblotting analyses of MDA-MB-231-derived cells (control, KD, S671A and S495A) for the expression of the indicated proteins. Cells were serum-starved for 24 h. DMSO or a mTOR inhibitor (0.1 µM final concentration) was added for 5 h before cell lysis. FIG. 6F shows in vivo xenograft tumor growth rate of MDA-MB-231-derived cells (WT DAXX, S671A, S495A, DCT and Y222P). FIG. 6G shows lipidomic profiling of xenograft tumors of the indicated cell types from FIG. 6F. FIG. 6H shows inhibited metabolic pathways and repressed/activated upstream regulators in MDA-MB-231 cells expressing S495A or S671A based on mRNA microarray data. RNAs were isolated from cells cultured in serum-free DMEM for 24 h as in FIG. 6D.

FIG. 7A shows the nuclear extracts of MDA-MB-231 cells were subjected to anti-DAXX IP in the absence (0) or the presence of SIM2 (1 and 5 µM). The immunoprecipitates, input and supernatants were analyzed by immunoblotting. FIG. 7B shows the MDA-MB-231 cells were implanted into mammary fat pads of female NSG mice. Mice were dosed i.p. daily weekdays for three weeks with vehicle or SIM2 (25 mg/kg). Longitudinal tumor volumes, mouse body weights, and endpoint tumor weights and images are shown. FIG. 7C shows SIM2 dosing reduced the expression of DAXX, SREBP2 and FASN in tumors. Protein extracts from three representative MDA-MB-231 xenograft tumors in vehicle and SIM2-treated mice were subjected to immunoblotting. HSP60 was detected as a loading control. FIG. 7D shows the mouse mammary tumor 4T1 cells were injected into mammary fat pads of female BALB/c mice. Mice were dosed as in FIG. 7B. Longitudinal tumor volumes, mouse body weights, and endpoint tumor weights and tumor images are shown. FIG. 7E shows lipid profiles of MDA-MB-231 xenograft tumors treated with vehicle or SIM2. Shown are a plot of a principal component analysis of lipid molecules detected by LC/MS, a heatmap of top lipid species, and bar graphs of relative abundance of the indicated lipid molecules. Gray and red bars represent tumor samples from mice treated with vehicle or SIM2 respectively. The p values were calculated based on Student's t-test. *: $p<0.05$; **: $p<0$.

FIG. 8A shows a principal component analysis of lipogenesis gene expression in normal breast tissues and breast cancer samples from a TOGA breast cancer dataset (TOGA, Nature, 2012). FIG. 8B is a gene expression heatmap of the indicated genes in normal breast tissues and breast cancer samples based on a TOGA breast cancer dataset (TOGA, Nature, 2012). FIG. 8C shows the mRNA expression levels for DAXX and SREBP2 in normal breast tissues and tumors of the indicated breast cancer subtypes based on an analysis of a TOGA breast cancer dataset. FIG. 8D shows cholesterol levels in normal control and breast tumors of the indicated subtypes based on a published dataset (Tang X. et al., 2014; PMID: 25091696). FIG. 8E is a heatmap of relative mRNA levels of DAXX along with select genes in the lipid metabolism pathways. The red and blue groups refer to a high level or low level of mRNA expression of the indicated genes according to combined expression scores in an individual tumor sample. FIG. 8F shows genomic features of DAXX and the indicated genes in the lipid metabolism pathways. The percentages of breast tumor samples with the gain (mRNA upregulation or copy number gains), and the loss of gene functions (mRNA upregulation or copy number losses) are shown. FIG. 8G is a Kaplan-Meier plot of the correlation between gene expression levels of the select genes in FIG. 8C and patient survival time. P values: *: <0.05, : <0.01, *: <0.001 (panels A and B; Student's t test). For panel E, the p value was based on a Mantel-Cox log-rank test; n, number of patients in each group.

FIG. 9A shows MDA-MB-231 cells stably transfected with a control vector (Control), a DAXX shRNA (KD), or the wt DAXX cDNA (OE) were cultured in the presence of serum or serum-starved for 24 hours. The cells were then fixed and stained with an anti-FASN polyclonal antibody and counter-stained with DAPI for visualizing nuclei. The cells were imaged using a fluorescence microscope. All images were captured with the same duration of light exposure for the red or blue channel. FIG. 9B shows immunoblotting analysis of cell extracts of the four MDA-MB-231-derived cell lines, cultured in the DMEM medium with 10% bovine calf serum with antibodies against the indicated proteins. FIG. 9C shows immunoblotting analysis of cell extracts of the H1299 cells expressing tetracycline (Tet)-inducible wt DAXX, cultured in the DMEM medium with 10% bovine calf serum in the presence of control (DMSO) or Tet with antibodies against the indicated proteins. FIG. 9D shows qRT-PCR validation of mRNA levels for the indicated genes in the four MDA-MB-231-derived cell lines as in FIG. 9B. Cells were cultured in serum-free medium for 24 h. RNAs were isolated for RT and qPCR *: $p<0.05$;**: $p<0.01$ (t-test vs control). FIG. 9E shows gene set enrichment analyses (GSEA) of lipogenic genes (fatty acid or cholesterol biosynthesis) that are downregulated in MDA-MB-231 DAXX DSM OE cells compared to DAXX wt OE cells. The cells were cultured in the DMEM medium without serum for 24 h and RNAs were isolated for RNA-seq analysis. Differentially expressed genes (±1.3 fold) between the two cell lines were included for IPA.

FIGS. 10A and 10B show mass spectrometry quantification of lipid species in cell lines (control: CTL, shDAXX: KD, wt DAXX OE: WT, or DSM OE: DSM) derived from MDA-MB-231 (FIG. 10B) or MDA-MB-468 (FIG. 10C). Lipid extraction and mass spectrometry analysis were conducted as in FIG. 1E. The p values were based on two-tailed unequal variance Student's t-test. *: $p<0.05$;  $p<0.01$; *: $p<0.001$. FIG. 10C shows mass spectrometry quantification of select lipid species in MDA-MB-231 cells with a control vector (CTL) and DAXX depletion by CRISPR/Cas9 (CRISPR DAXX). A validation immunoblot of DAXX depletion is shown. Mass spectrometry was done as above. FIG. 10D shows DAXX knockdown reduces acetate-dependent lipogenesis in cancer cells. The luminal estrogen receptor-expressing BC cell lines MCF7 and T47D and the colon cancer cell line HCT116 with a control vector or a DAXX-specific shRNA were subject to de novo lipogenesis assay using [$^{14}$C] acetate labeling as in FIG. 1G. The radioactivity counts were normalized against total protein levels. Shown are average values (±SEM, n=3).

FIG. 11A is a heatmap of the indicated lipogenic genes in control and DAXX KD cells of the human prostate cancer PC3 cell line. FIG. 11B is a heatmap of the indicated lipogenic genes in wt and DAXX KO cells of the mouse embryonic stem cells (mESC). FIG. 11C is a heatmap of the indicated lipogenic genes in liver tissues from mice with Scap deletion (Scap−/−), the nuclear form of Srebp1a or Srebp2 transgene. FIG. 11D are Pearson correlation plots of the mRNA levels of DAXX vs. SREBF1 or SREBF2 based on the METABRIC breast cancer dataset. The p values were based on two-tailed unequal variance Student's t-test.

Figure 12A:
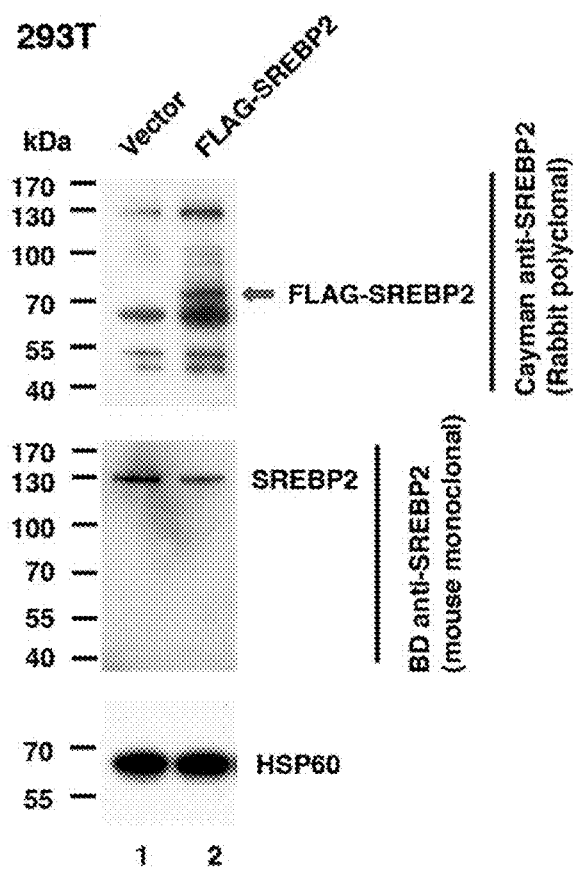

FIGS. 12A to 12C show validation of SREBP2 expression in immunoblotting. FIG. 12A shows 293T cells transfected with a control vector or a vector for FLAG-SREBP2 (mature). The cell lysates were subjected to immunoblotting with two different anti-SREBP2 antibodies: a rabbit polyclonal antibody raised against an immunogen within the mature form of SREBP2 (Cayman, catalog #10007663; upper panel) and a mouse mAb raised against human SREBP2 aa. 833-1141 (BD Biosciences, catalog #557037; lower panel). The transfected mature form of SREBP2 with a FLAG tag is denoted with an arrow, which was detected by the Cayman antibody but not the BD antibody. FIG. 12B shows MDA-MB-231 cells fractionated into cytoplasmic and nuclear fraction, which were analyzed in immunoblotting using the Cayman antibody as in FIG. 12A. Note that the mature form (M) of SREBP2 (~55 kDa) was only detected in the nuclear fraction. P: the precursor form of SREBP2. FIG. 12C shows whole cell lysates of the breast cancer cell line Hs578T and colon cancer cell line HCT116 were subjected to immunoblotting using the Cayman antibody as in FIGS. 12A and 12B.

Figure 13A:
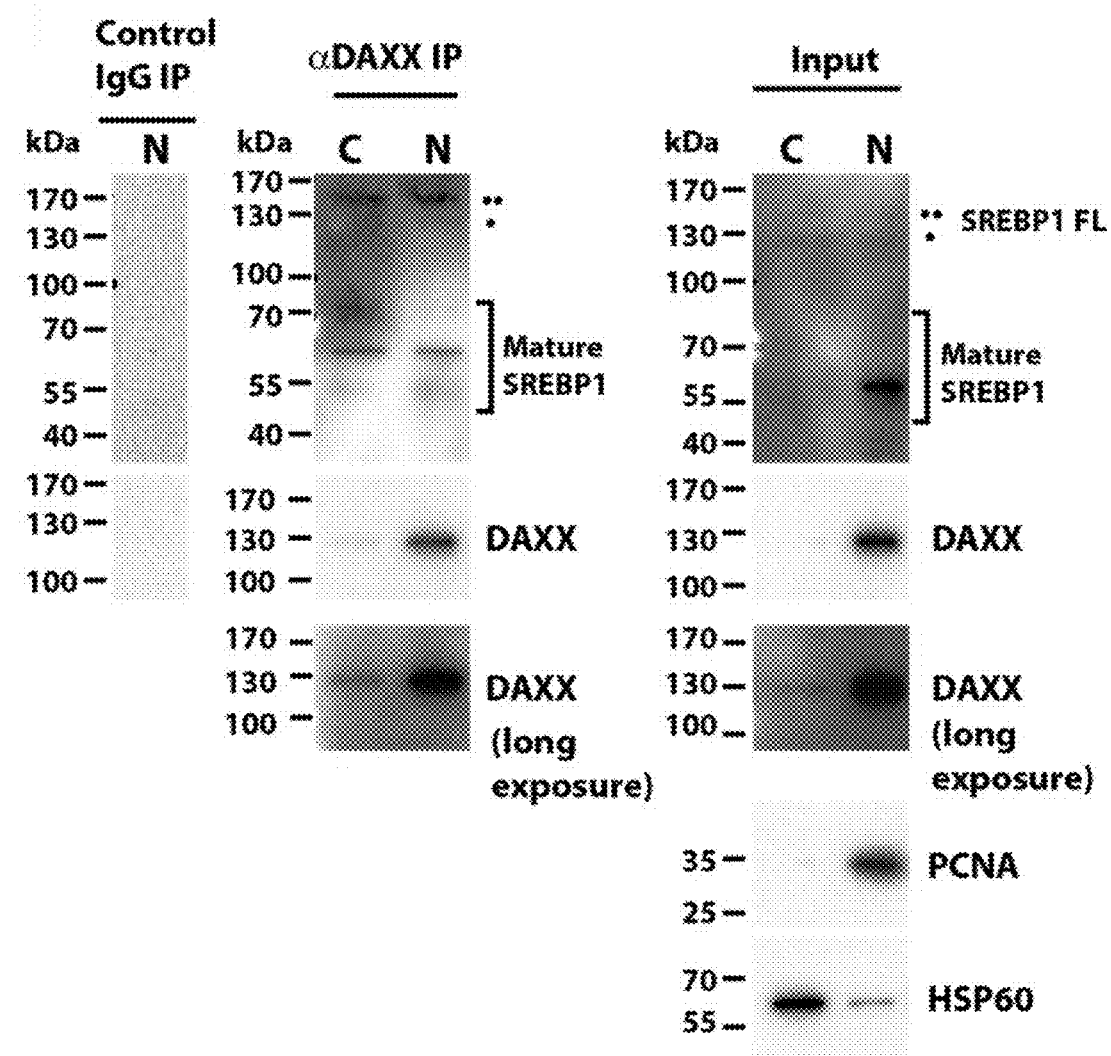
Figure 13B:
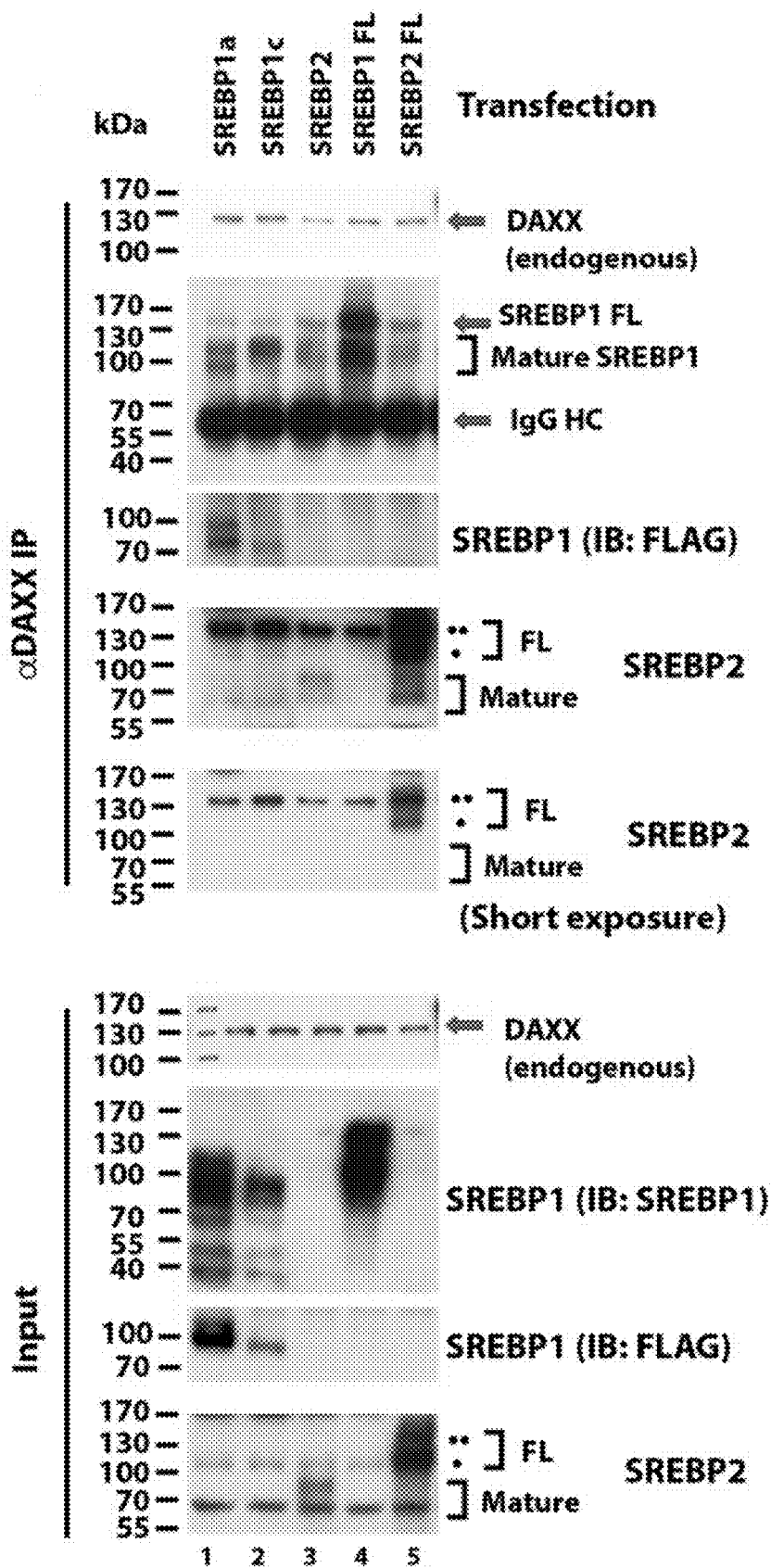
Figure 13C:
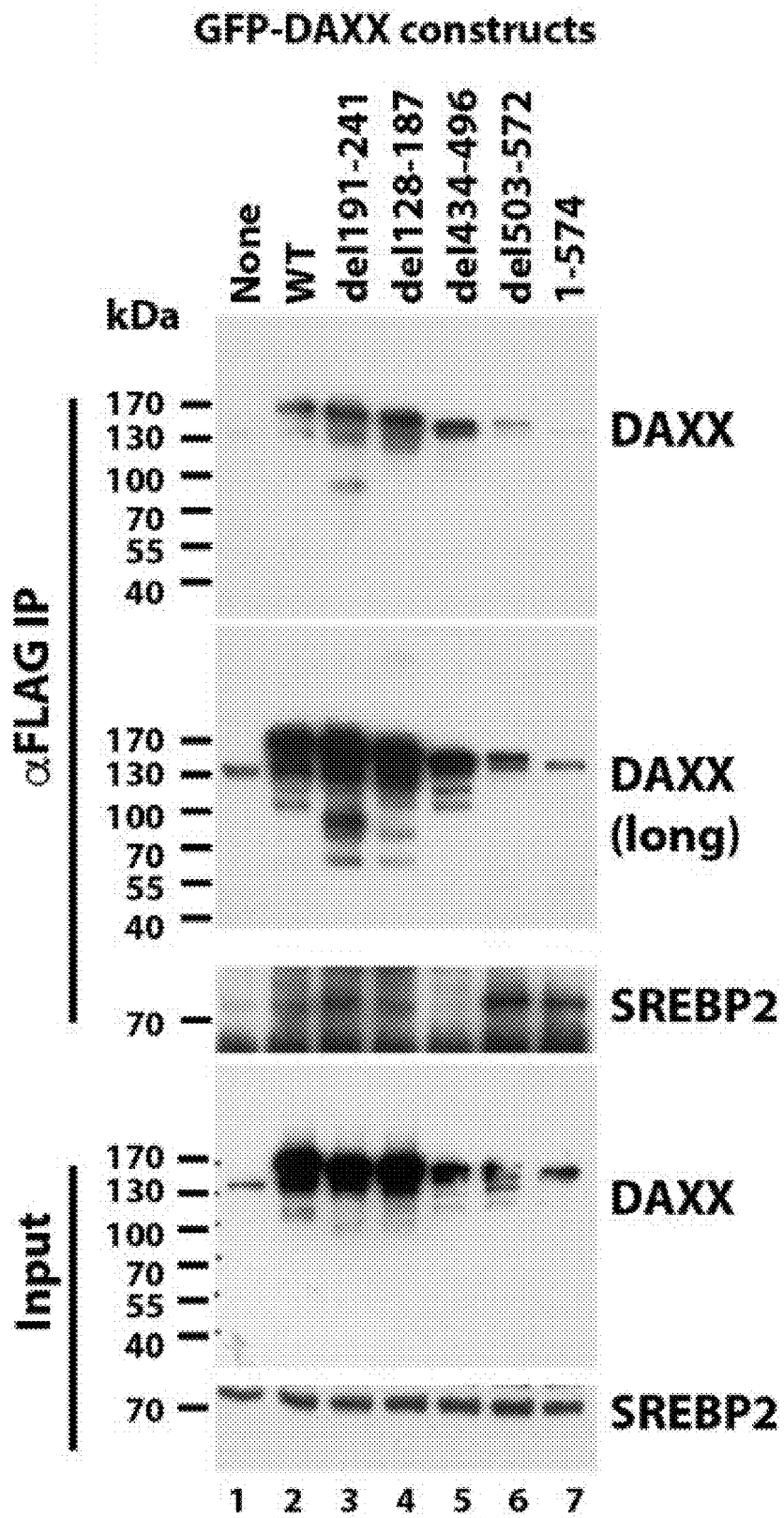
Figure 13D:
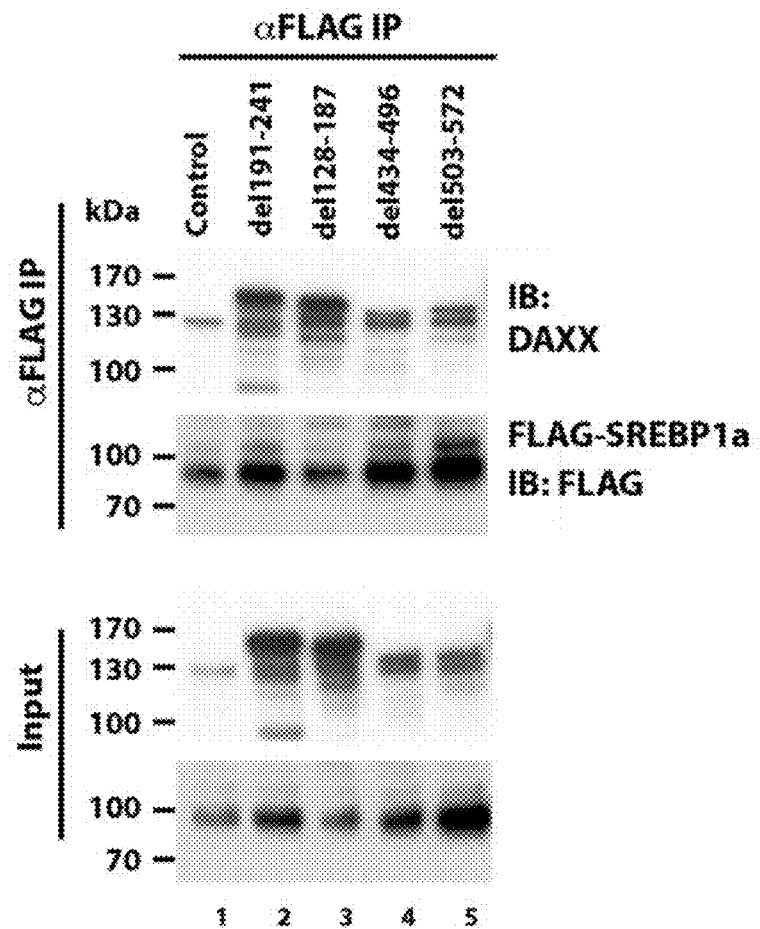
Figure 13E:
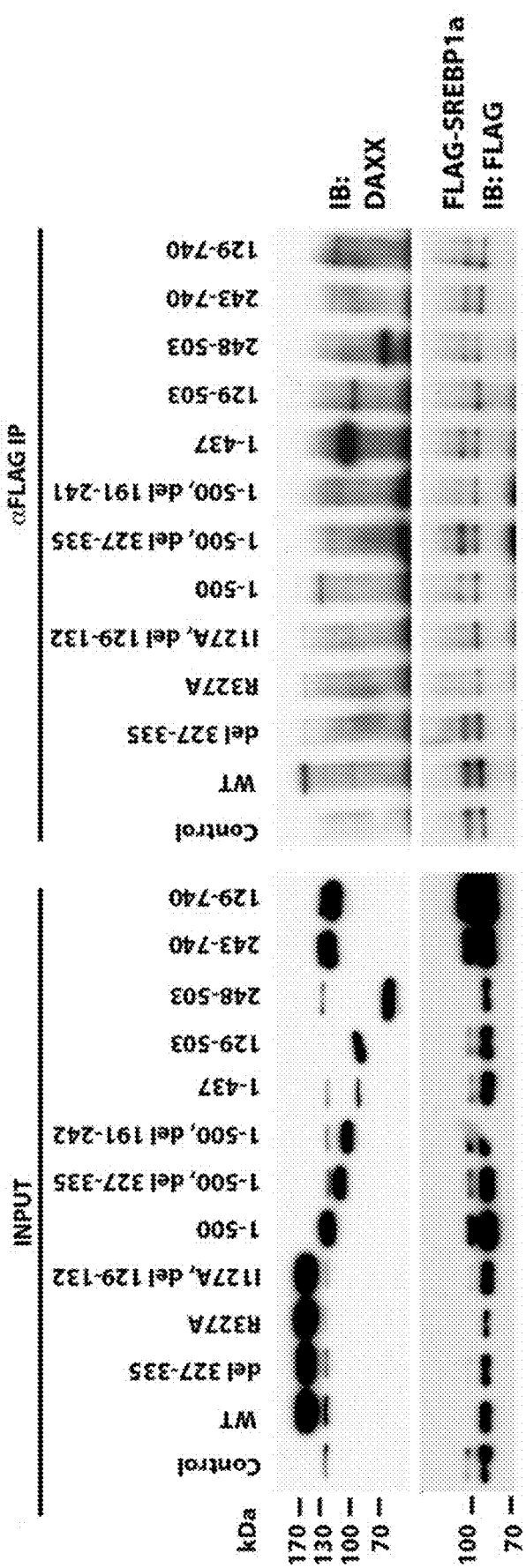

FIGS. 13A to 13E show DAXX interacts with SREBP1 and SREBP2. FIG. 13A shows MDA-MB-231 cells were fractionated into the cytoplasmic (C) and nuclear fraction (N). The corresponding cytoplasmic and nuclear extracts were subjected to IP with a mouse anti-DAXX mAb or a control IgG. SREBP1 and DAXX were detected by immunoblotting. Two larger bands of SREBP1 (likely the precursors, denoted with • and •• respectively) were detected. The upper band (>130 kDa) was the major SREBP1 precursor band in the DAXX immunoprecipitates. The mature forms of SREBP1 consist of several species, with the major band (~60 kDa) being seen predominantly in the nucleus (input sample). Notably, the mature SREBP1 was markedly enriched in the cytoplasmic fraction in DAXX immunoprecipitates, indicating that DAXX has a high affinity to mature SREBP1. FIG. 13B shows an expression vector for the mature form of SREBP1a, SREBP1c, or SREBP2 as well as for the full-length SREBP1 or SREBP2 was transfected to 293T cells. The total lysates of transfected cells were subjected to IP and immunoblotting as in FIG. 13A. Note that two bands of FL SREBP2 were seen in the SREBP2 FL-transfected cells. The lower band (denoted with) was the major band in the absence of SREBP2 FL transfection, which is likely the canonical SREBP2 precursor (~125 kDa). The upper band (>130 kDa, denoted with) was the major SREBP2 precursor band in the DAXX immunoprecipitates. FIG. 13C shows 293T cells cotransfected with FLAG-SREBP2 (mature) and GFP or an indicated GFP-DAXX construct. The cell lysates were subjected to FLAG IP and immunoblotting. FIGS. 13D and 13E show cotransfection of FLAG-SREBP1a (mature) and DAXX constructs, IP and immunoblotting experiments were performed as in FIGS. 13B and 13C.

Figure 14A:
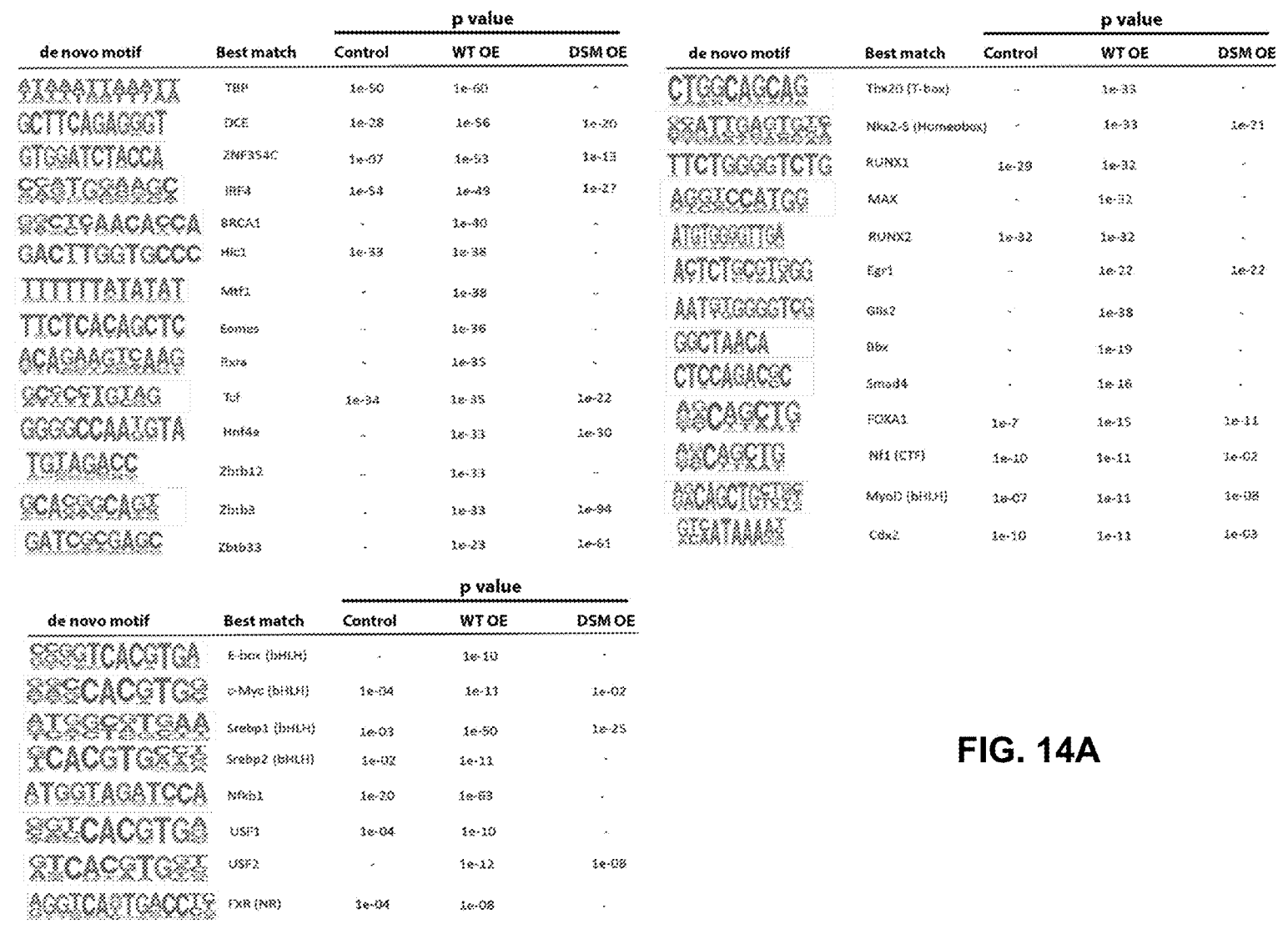
Figure 14B:
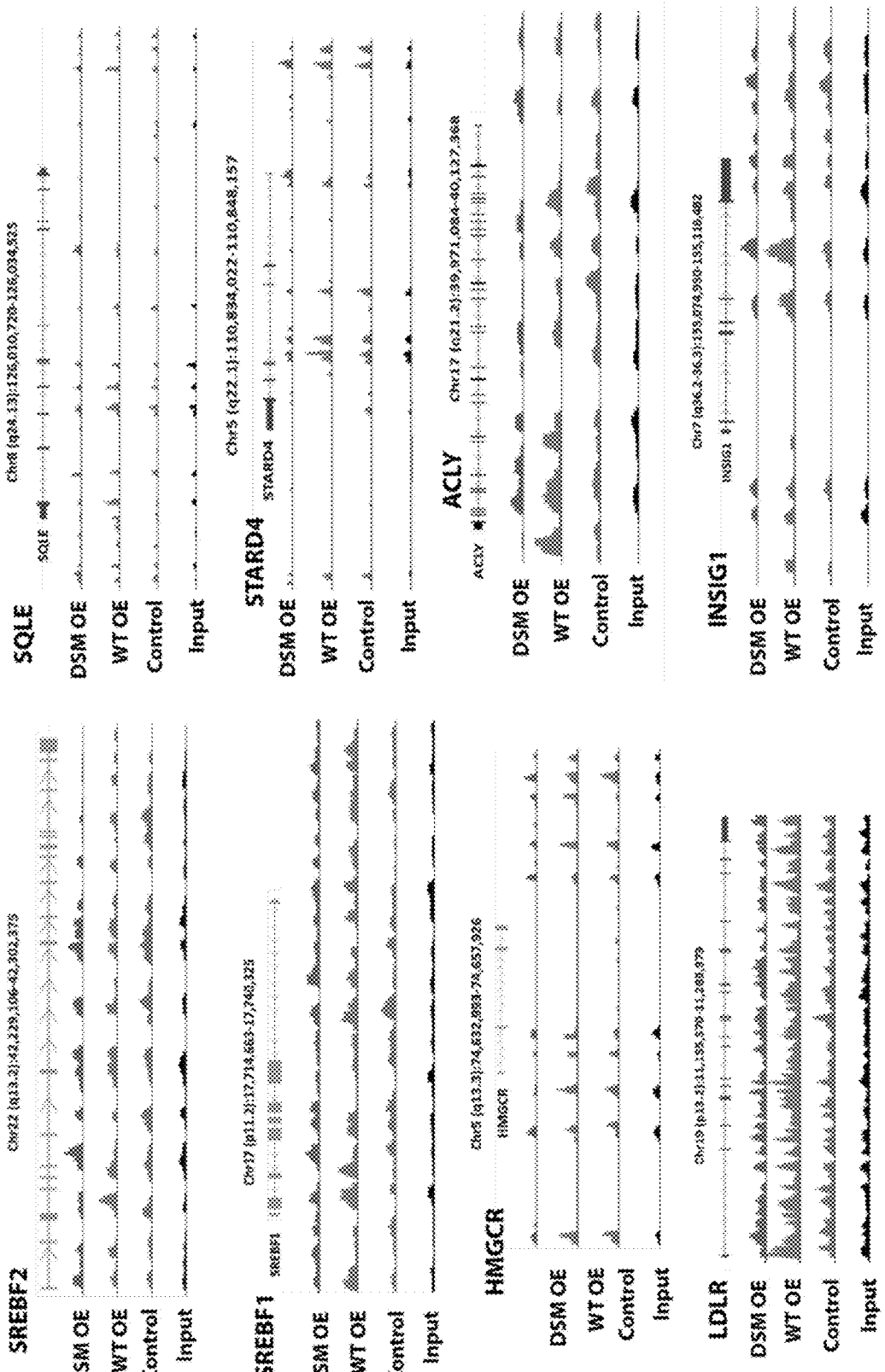
Figure 14C:
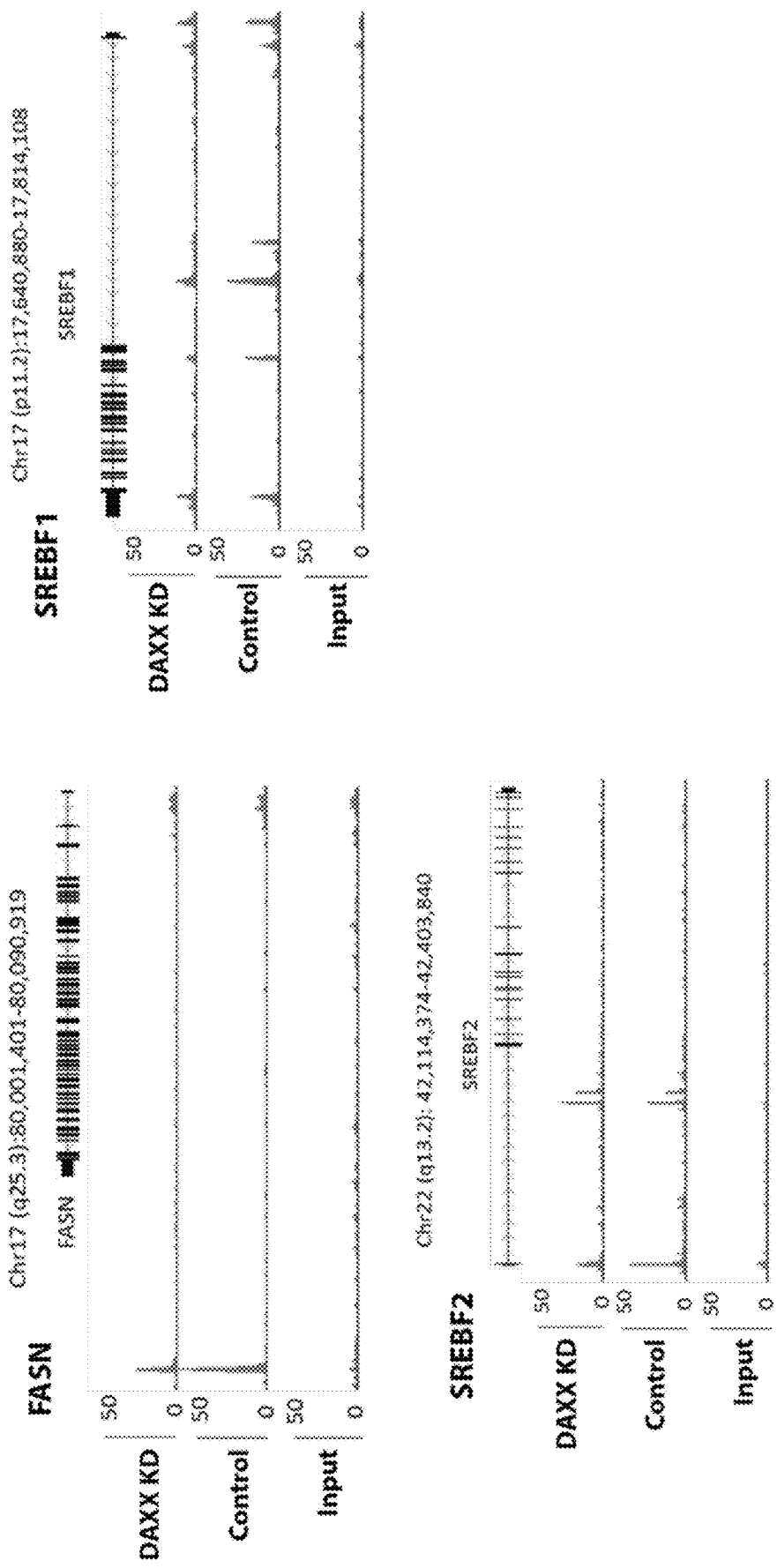

FIGS. 14A to 14C show chromatin-binding activity of DAXX. FIG. 14A show de novo motifs associated with DAXX as revealed by ChIP-seq. DAXX ChIP-seq and motif analysis were done as in FIG. 3. Motifs enriched in MDA-MB-231-derived cells (control, wt OE and DSM OE) are shown. FIG. 14B shows DAXX chromatin-binding profiles of the indicated individual lipogenic genes in MDA-MB-231-derived cells (control, wt OE and DSM OE) are depicted. FIG. 14C shows DAXX chromatin-binding profiles of the indicated individual lipogenic genes in PC3-derived cells (control vs. KD; Puto et al., 2015) are shown.

Figure 15A:
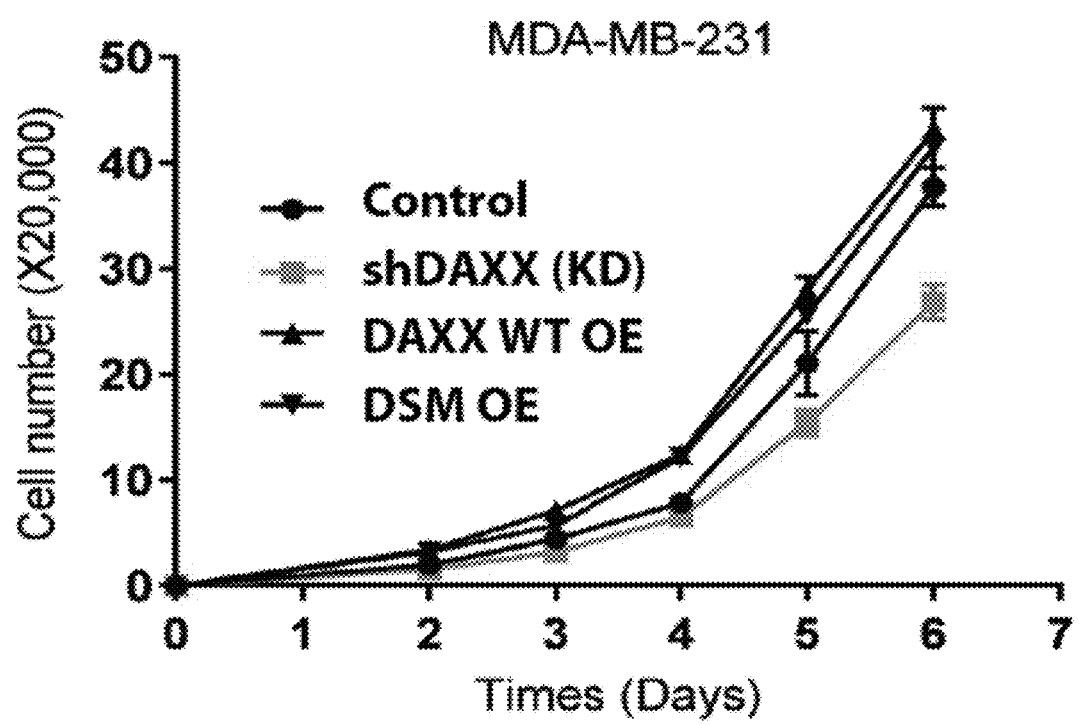
Figure 15B:
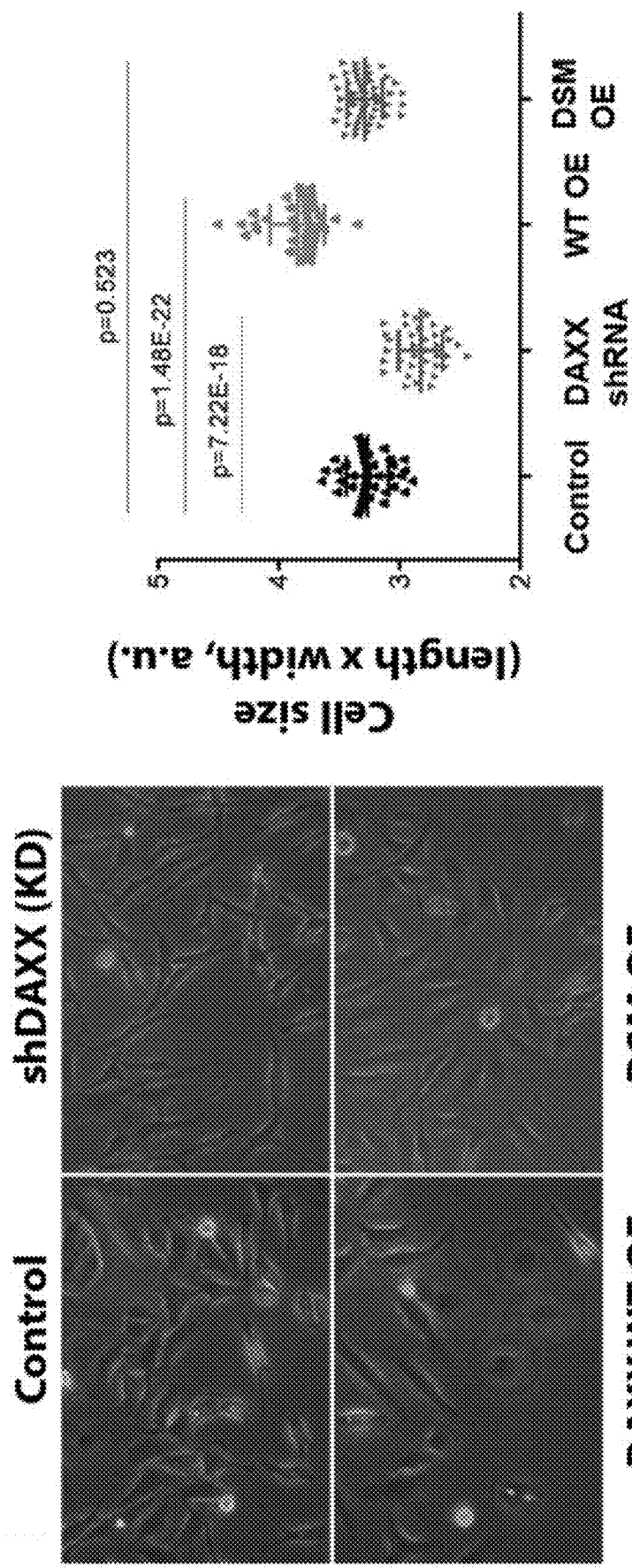
Figure 15C:
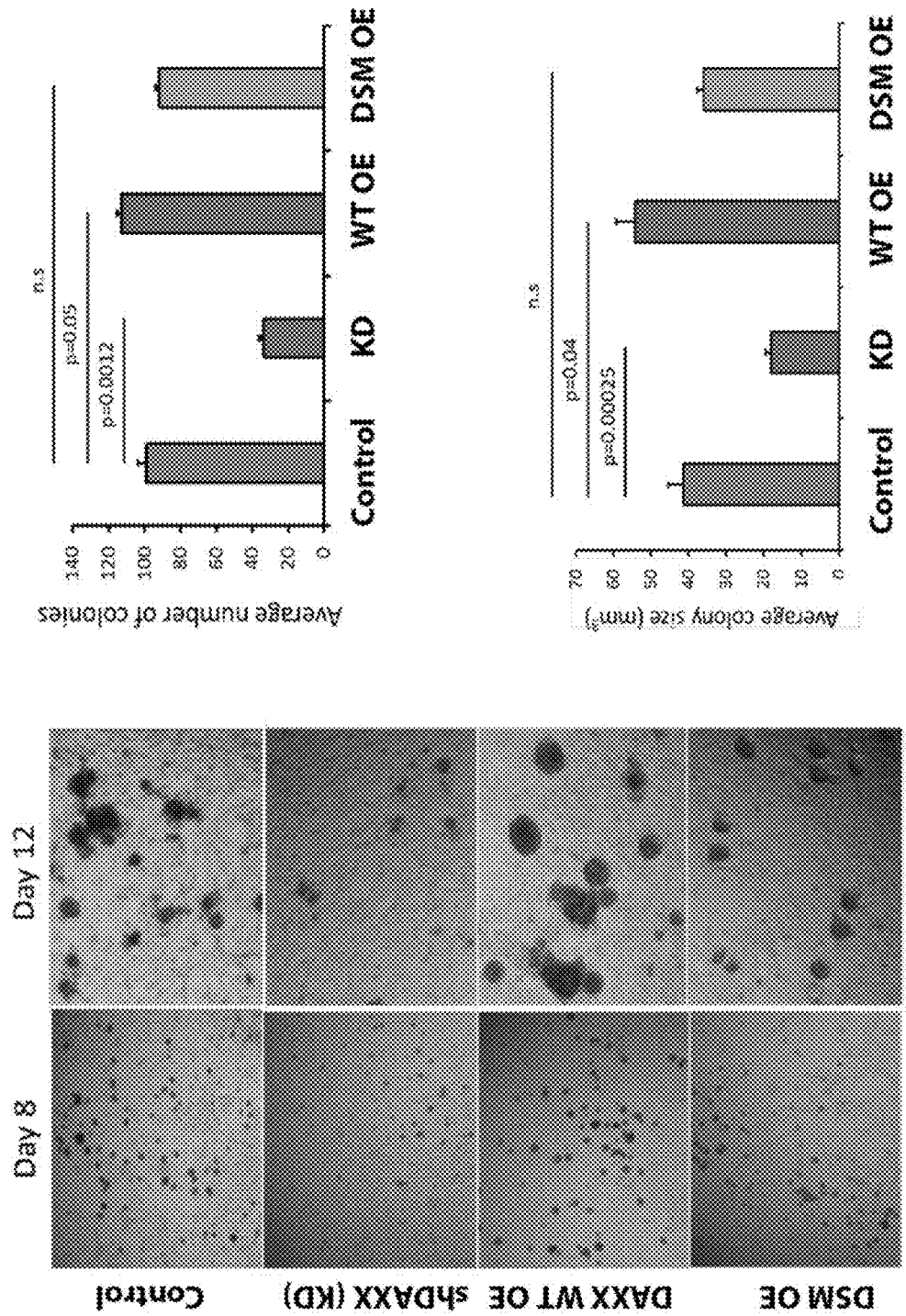
Figure 15E:
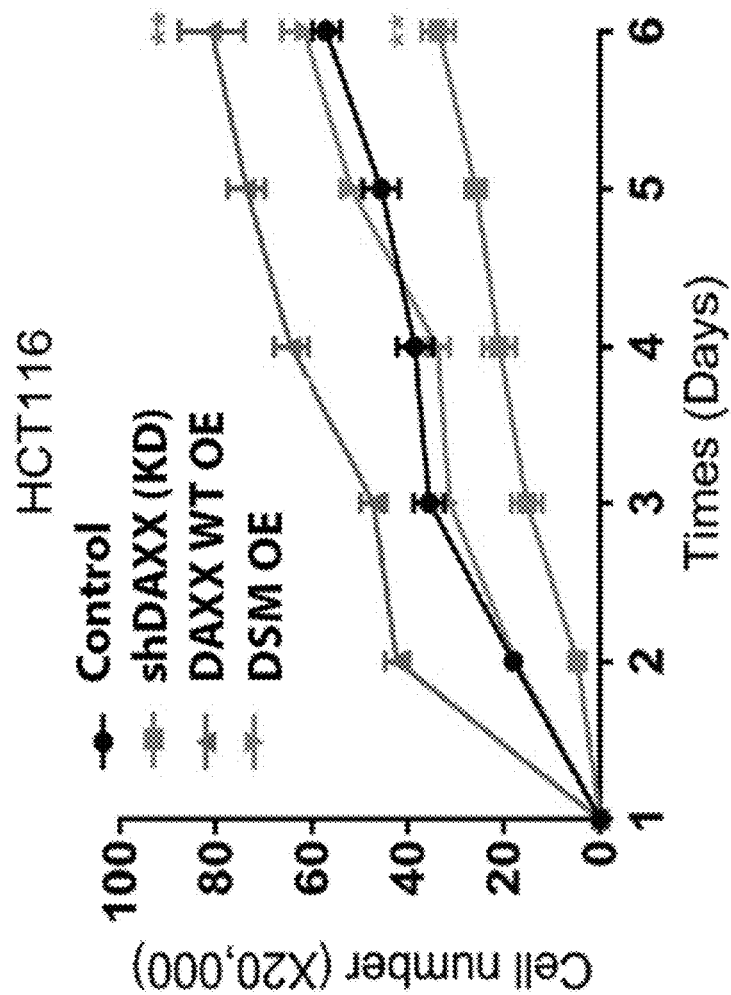
Figure 15D:
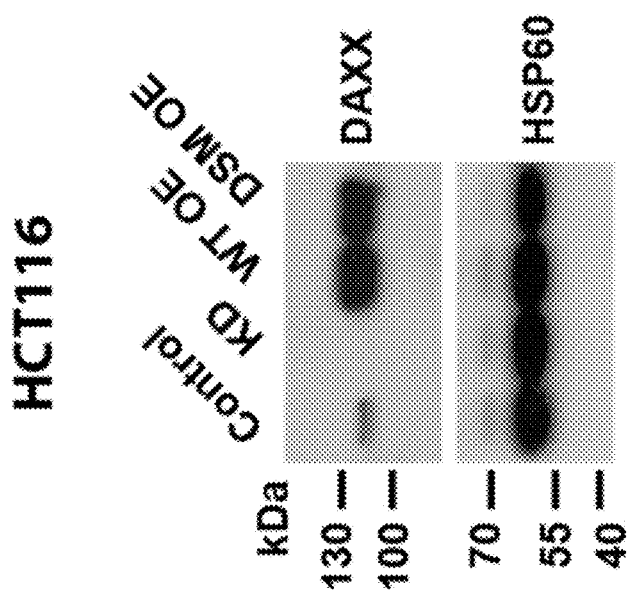
Figure 15F:
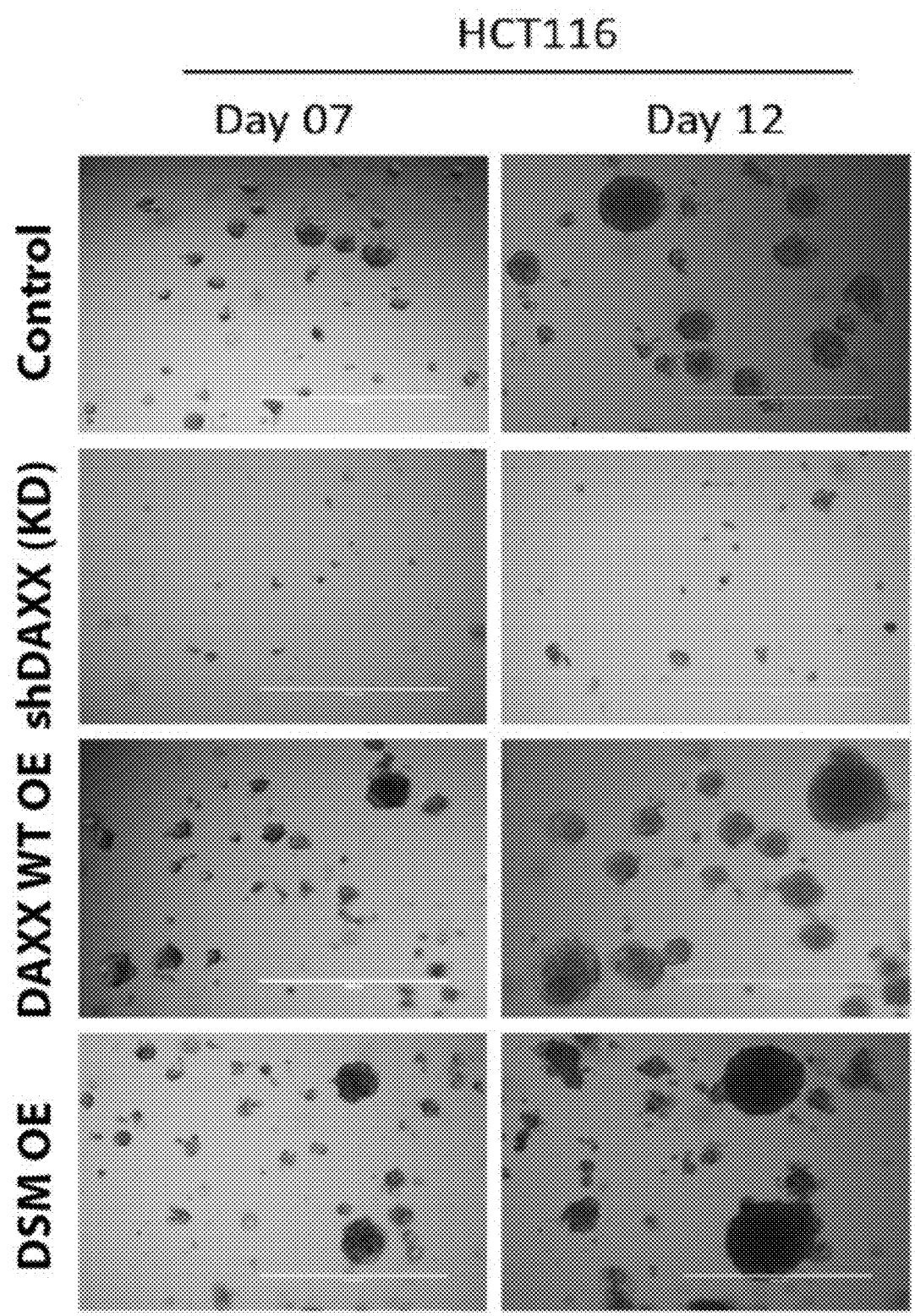
Figure 15G:
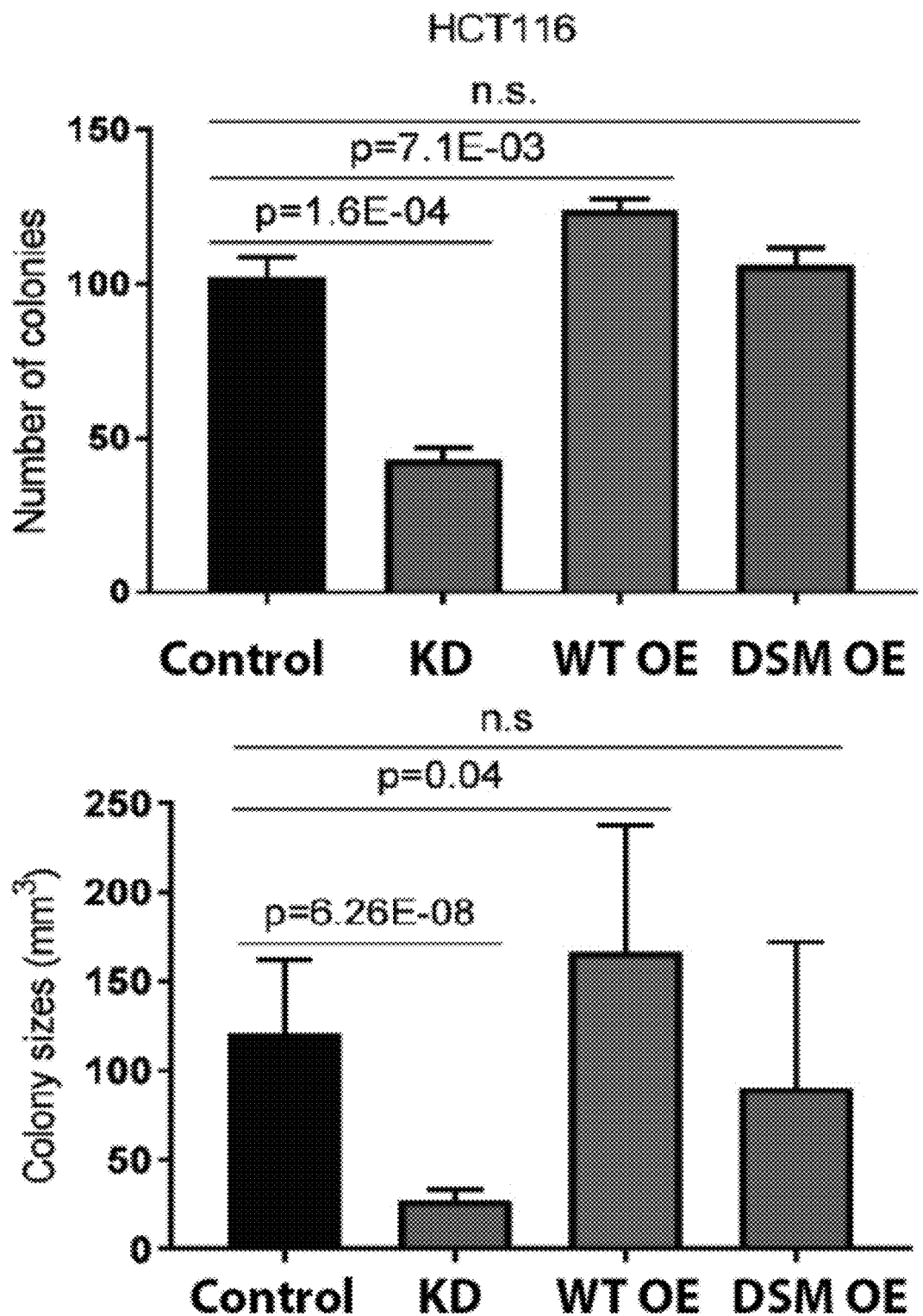
Figure 15H:
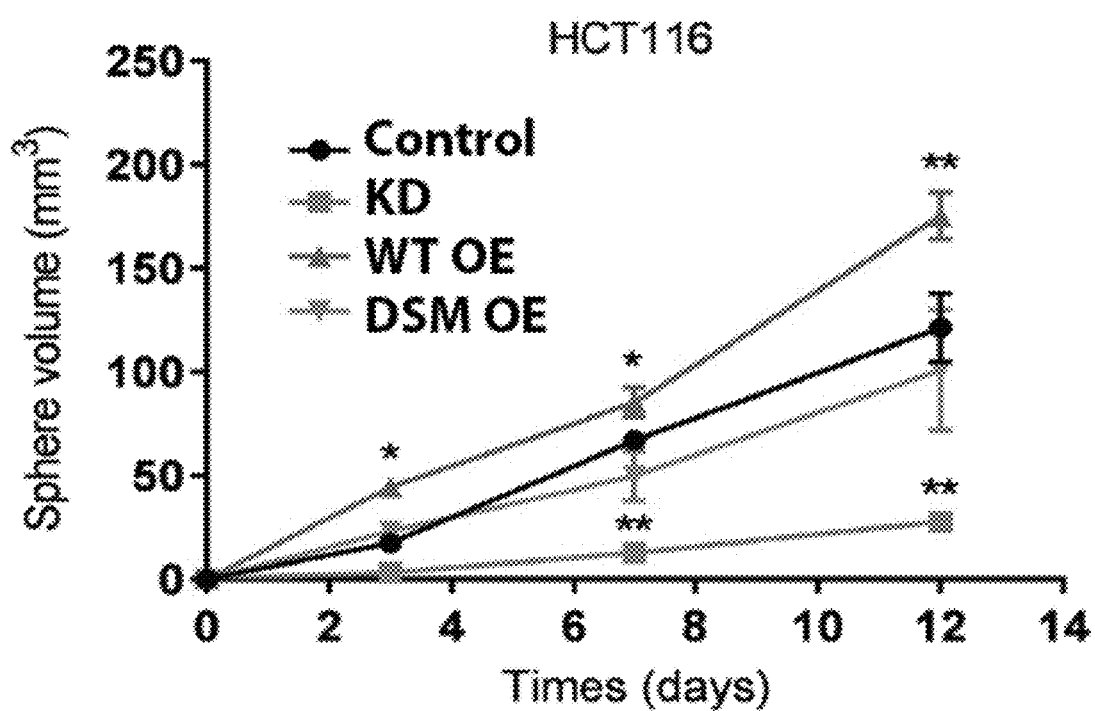

FIGS. 15A to 15H show DAXX promotes cell proliferation and 3D colony growth. FIG. 15A shows the panel of MDA-MB-231 derived cell lines cultured under conventional 2D cell culture conditions. The number of cells for each line was determined using an automatic cell counter and plotted vs. time. Shown are average cell numbers (±SEM, n=3). FIG. 15B are images of the cultures of the four MDA-MB-231-derived lines and cell size quantification. FIG. 15C shows cells cultured in a suspension with Matrigel and complete DMEM medium. The 3D colonies of each line were imaged at the indicated time. Colony number and size were quantified at Day 12. FIG. 15D shows DAXX protein levels in HCT116 cell line with a control vector, DAXX shRNA, wt DAXX cDNA and the DSM mutant as assessed by immunoblotting. FIG. 15E shows cell proliferation of the four HCT116 derived cell lines in 2D cell cultures was quantified as in FIG. 15A. FIG. 15F are representative images of 3D cultures of the four HCT116-derived cell lines on Day 7 and Day 12. Cells were cultured in Matrigel as in FIG. 15C. FIG. 15G shows colony number and size quantified as in FIG. 15C. FIG. 15H shows growth curves of the four HCT116-derived lines in 3D.

Figure 16A:
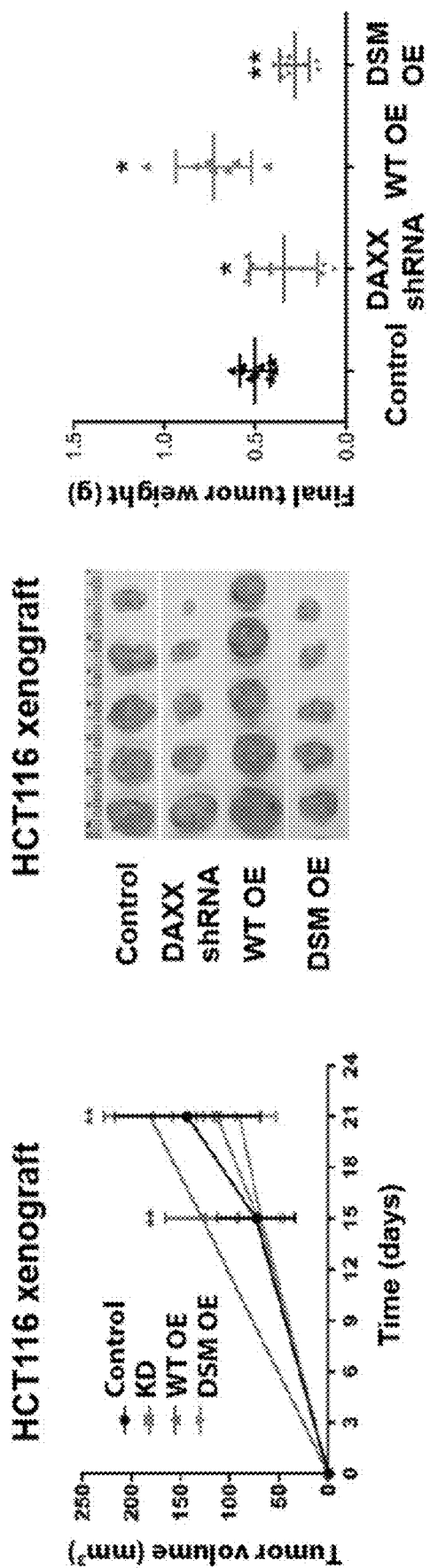
Figure 16B:
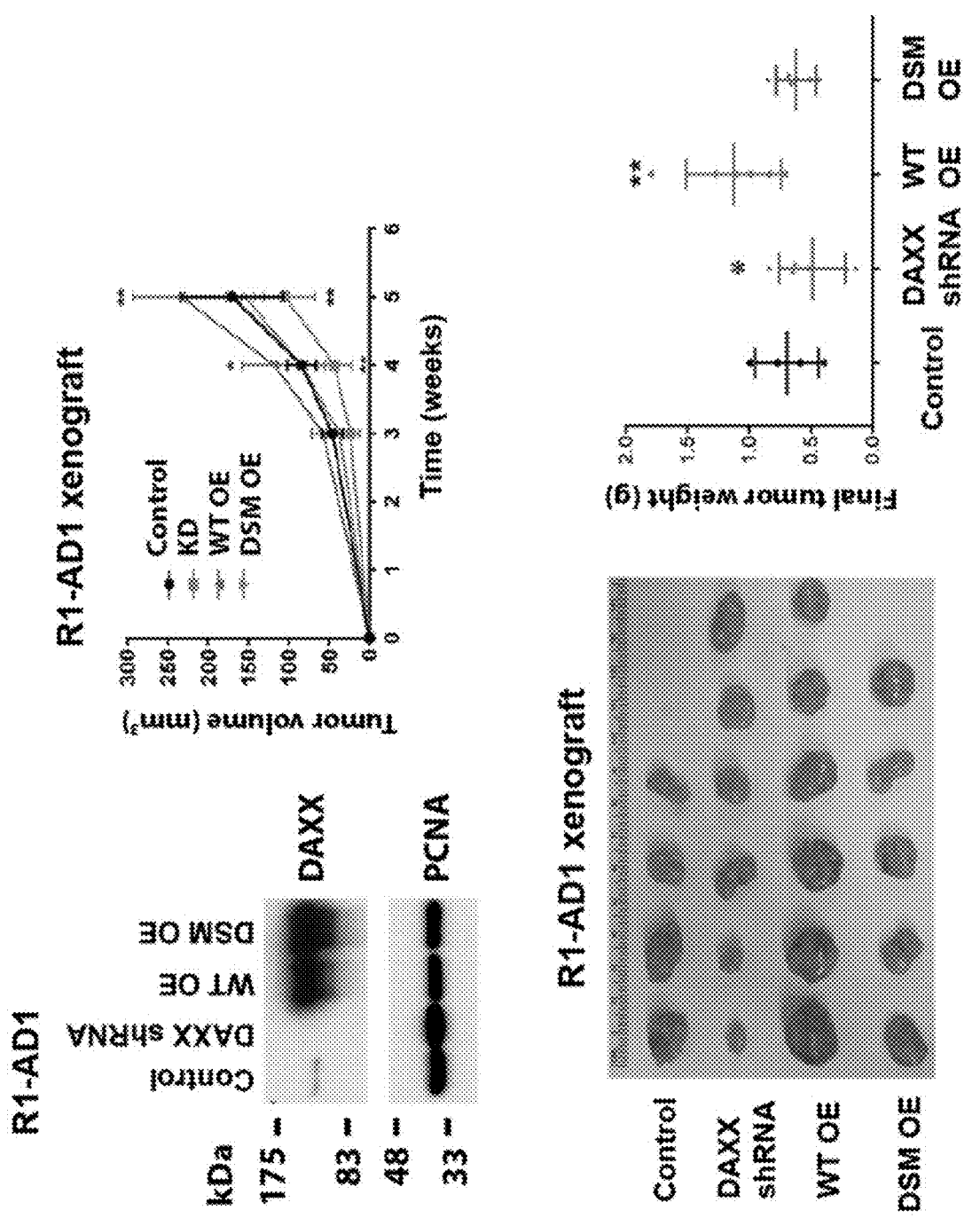
Figure 16C:
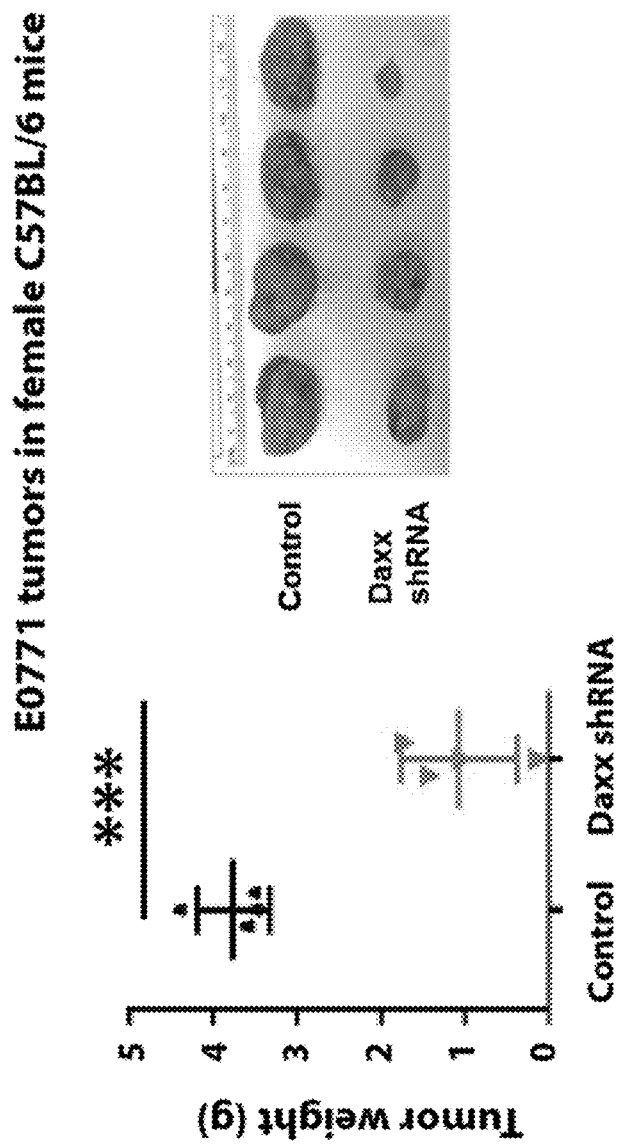
Figure 16C:
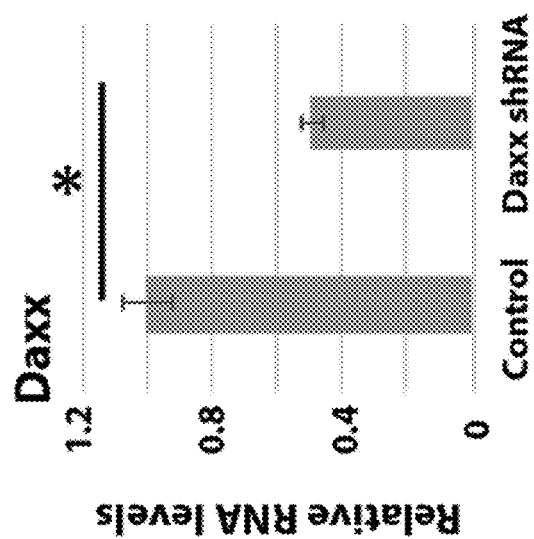
Figure 16D:
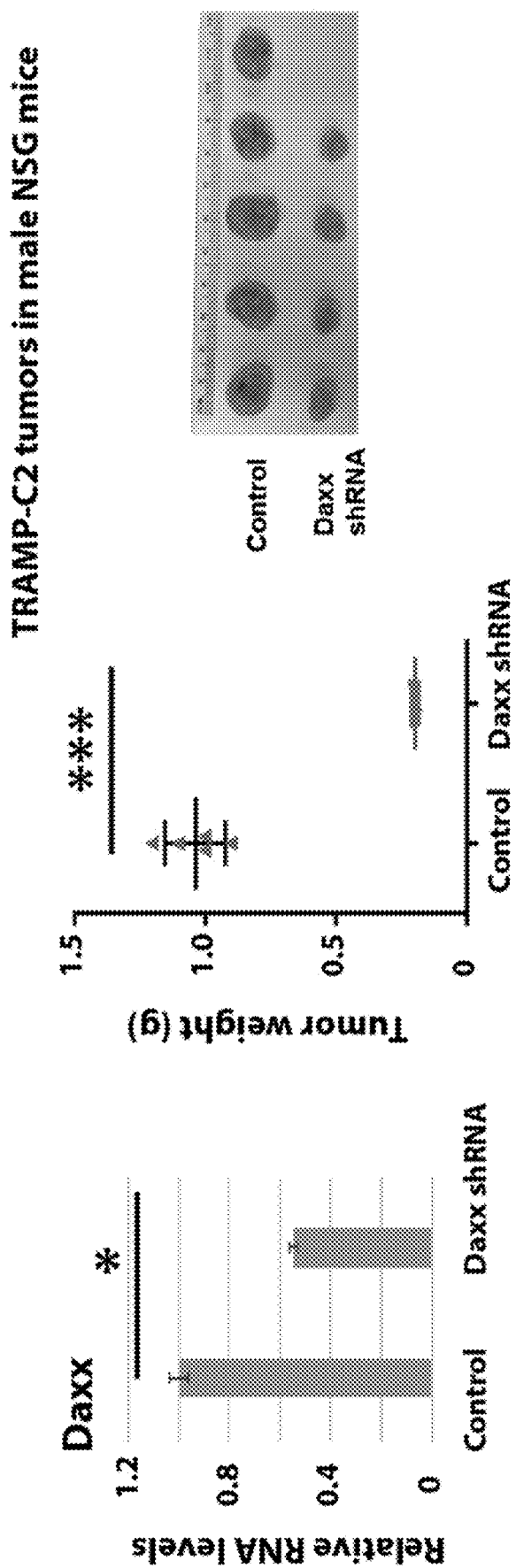

FIGS. 16A to 16D show DAXX enhances in vivo tumor growth. FIG. 16A shows the four HCT116-derived cell lines xenografted subcutaneously in a flank of NSG mice (both male and female). Tumor volumes were recorded and plotted (left). Representative images of dissected tumors are shown (middle). The final tumor weights are plotted and compared among groups (right). FIG. 16B shows DAXX protein levels in cells derived from the prostate cancer cell line R1-AD1 with a control vector, DAXX shRNA, wt DAXX cDNA or the delS mutant are shown (left). These cells were mixed with Matrigel and transplanted to male NSG mice subcutaneously as in FIG. 16A. Tumor volume plots, images of dissected tumors and their weights are shown. FIG. 16C shows the mouse breast cancer E0771 cells stably transduced with a control or a mouse Daxx shRNA were subjected to qRT-PCR (left). The cells were engrafted into the mammary fat pads of female C57BLJ6 mice. The final tumor weights are plotted (middle). The images of dissected tumors are shown (right). FIG. 16D shows the mouse prostate cancer TRAMP-C2 cells stably transduced with a control or a mouse Daxx shRNA were subjected to qRT-PCR (left). The cells were engrafted into male NSG mice subcutaneously as in FIG. 16B. The final tumor weights are plotted (middle). The images of dissected tumors are shown (right).

Figure 17A:
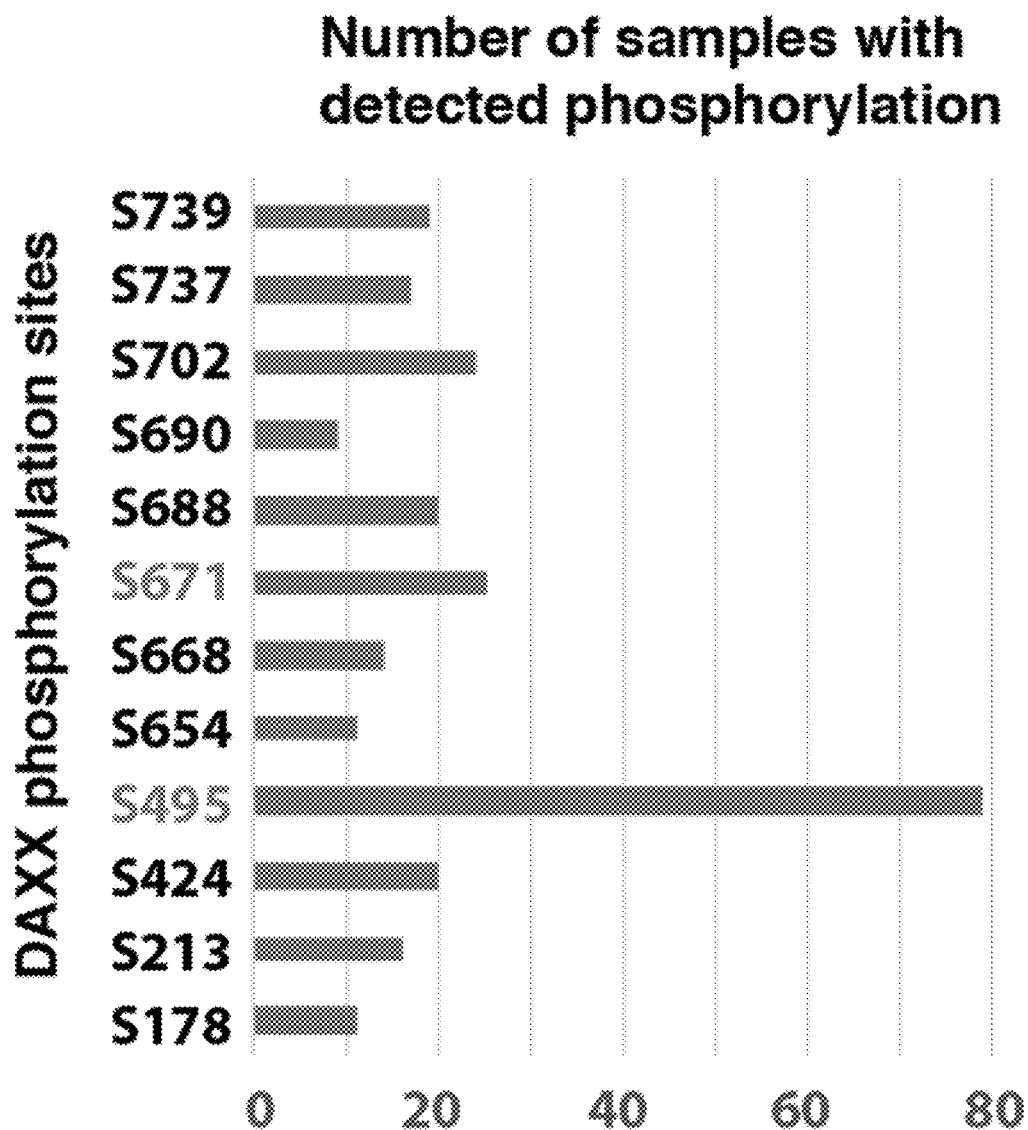
Figure 17B:
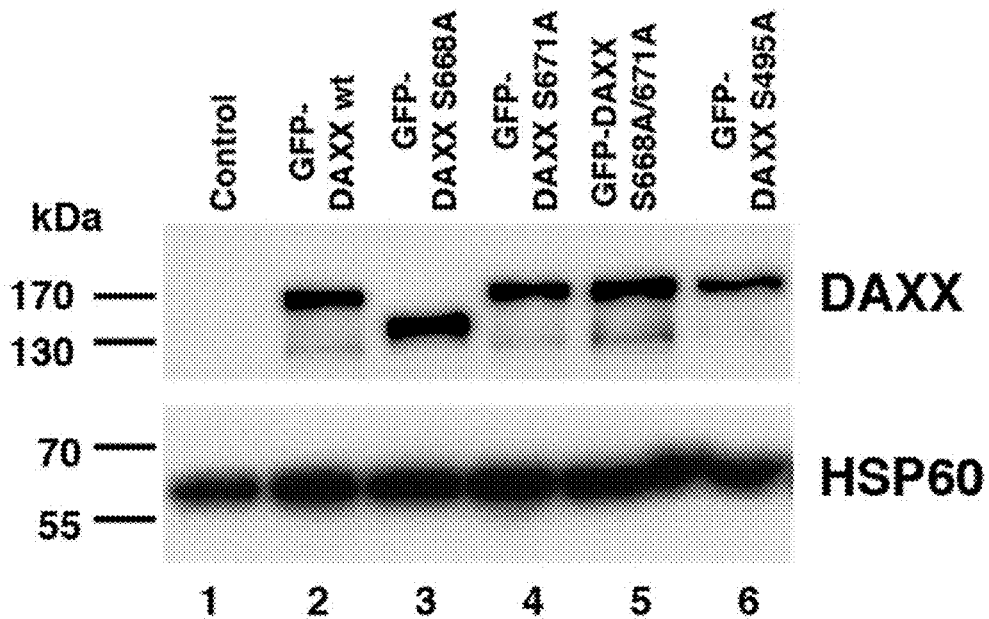
Figure 17C:
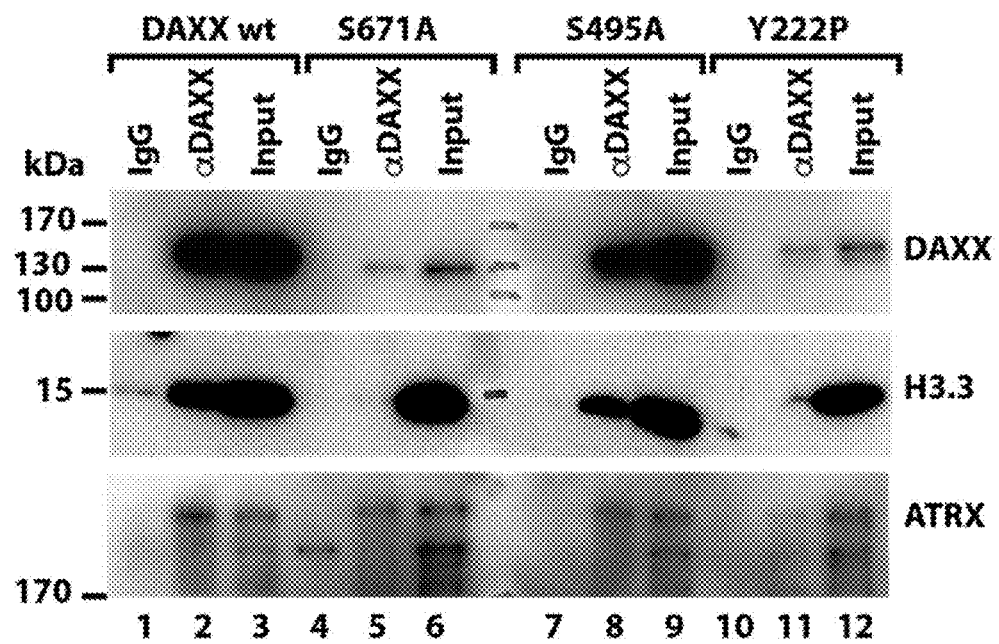
Figure 17D:
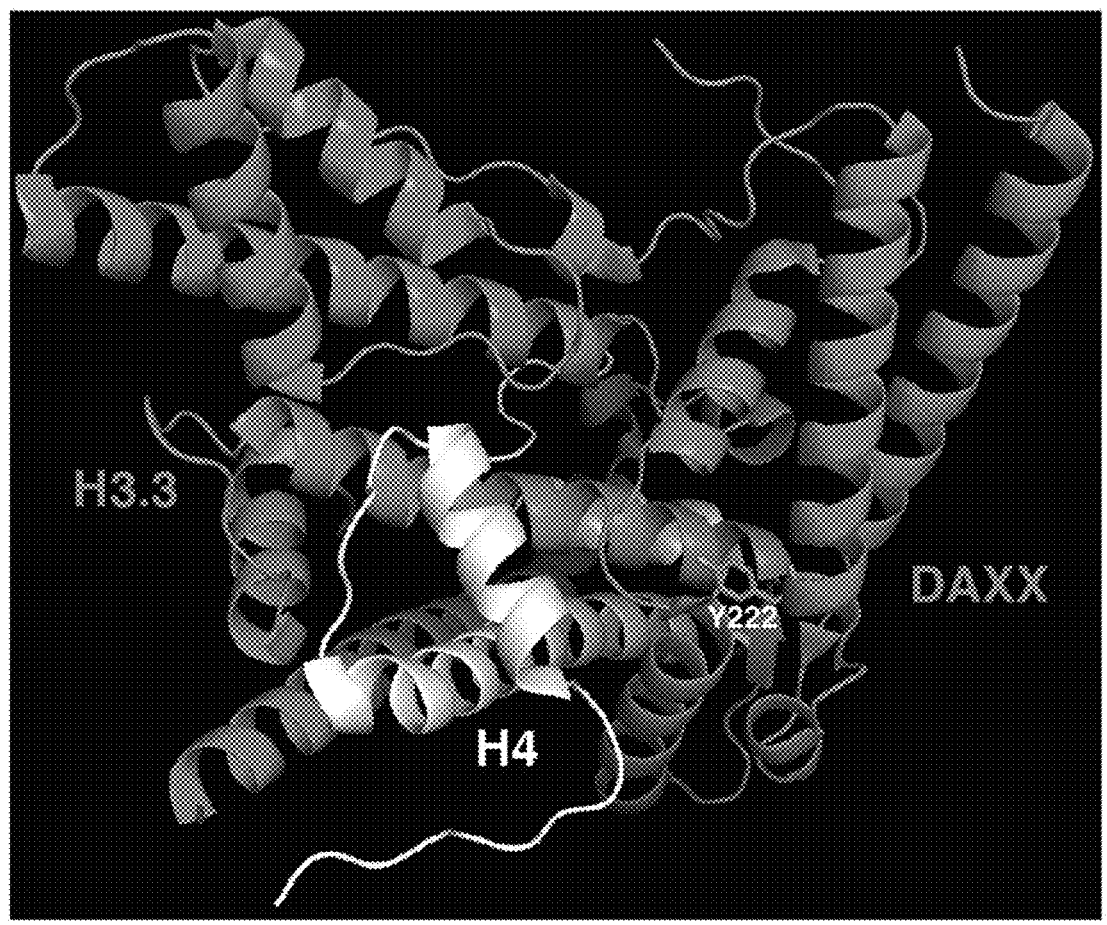

FIGS. 17A to 17D show characterization of DAXX mutants. FIG. 17A shows highly phosphorylated DAXX residues. FIG. 17B shows the indicated DAXX constructs were transfected to MDA-MB-231 cells and the lysates of transfected cells were subjected to immunoblotting with an anti-DAXX antibody. HSP60 was detected as a loading control. FIG. 17C shows co-immunoprecipitation of wt DAXX and the indicated mutants in MDA-MB-231 cell extracts with H3.3 and ATRX. FIG. 17D shows structure of DAXX HBD-H3.3/H4 dimer. The position of residue Y222 in DAXX is shown.

Figure 18A:
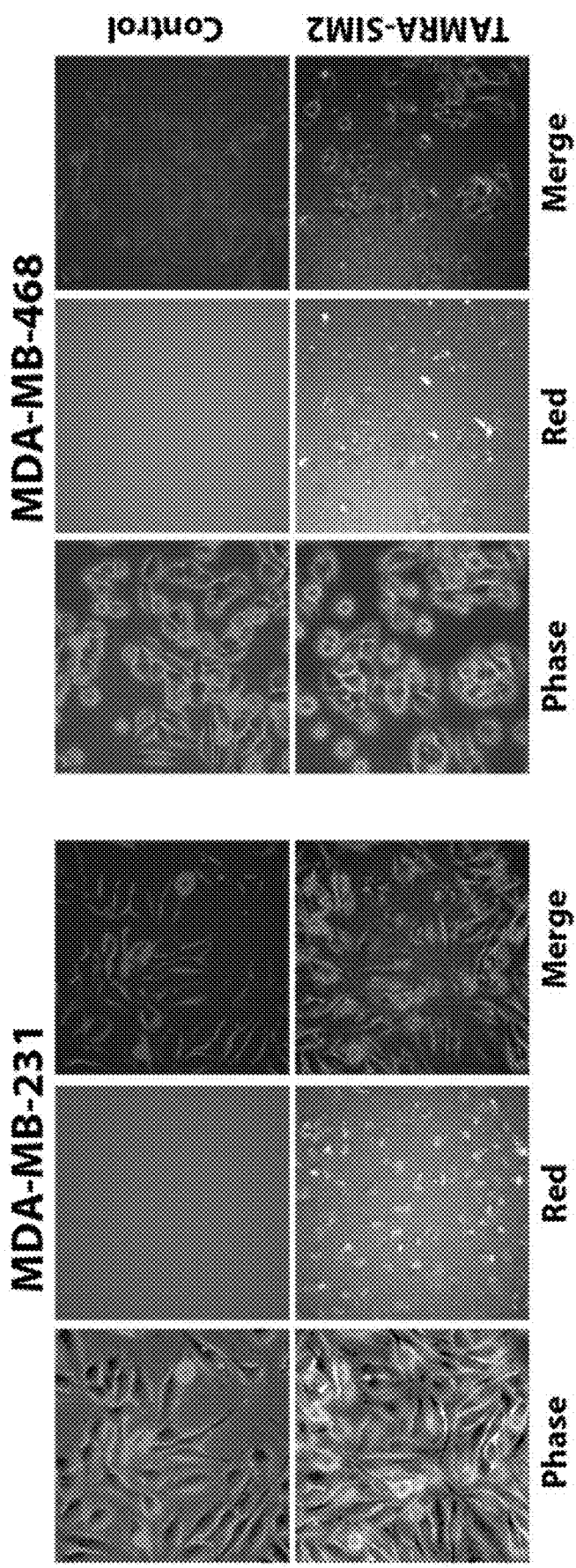
Figure 18B:
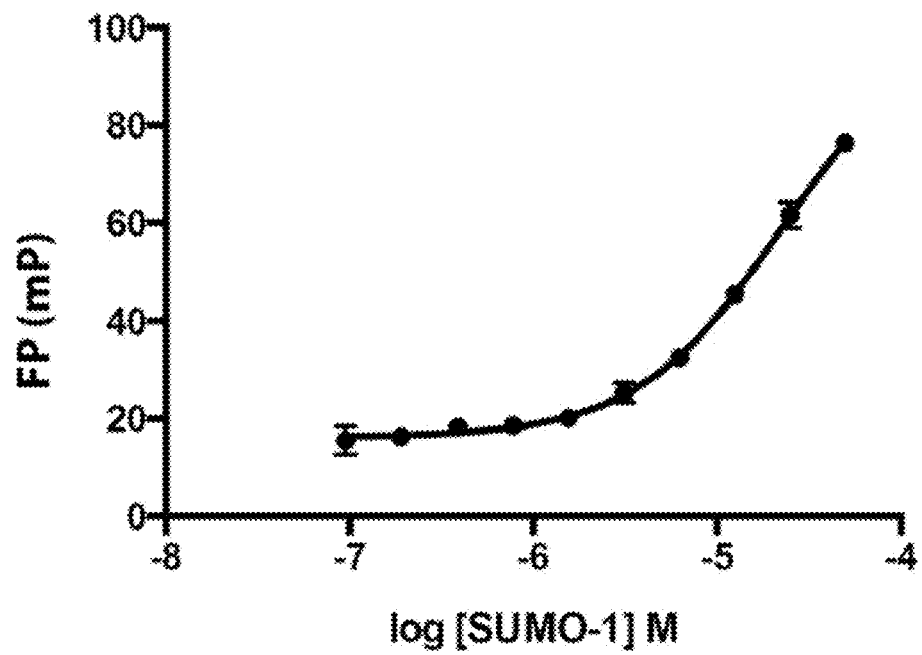
Figure 18C:
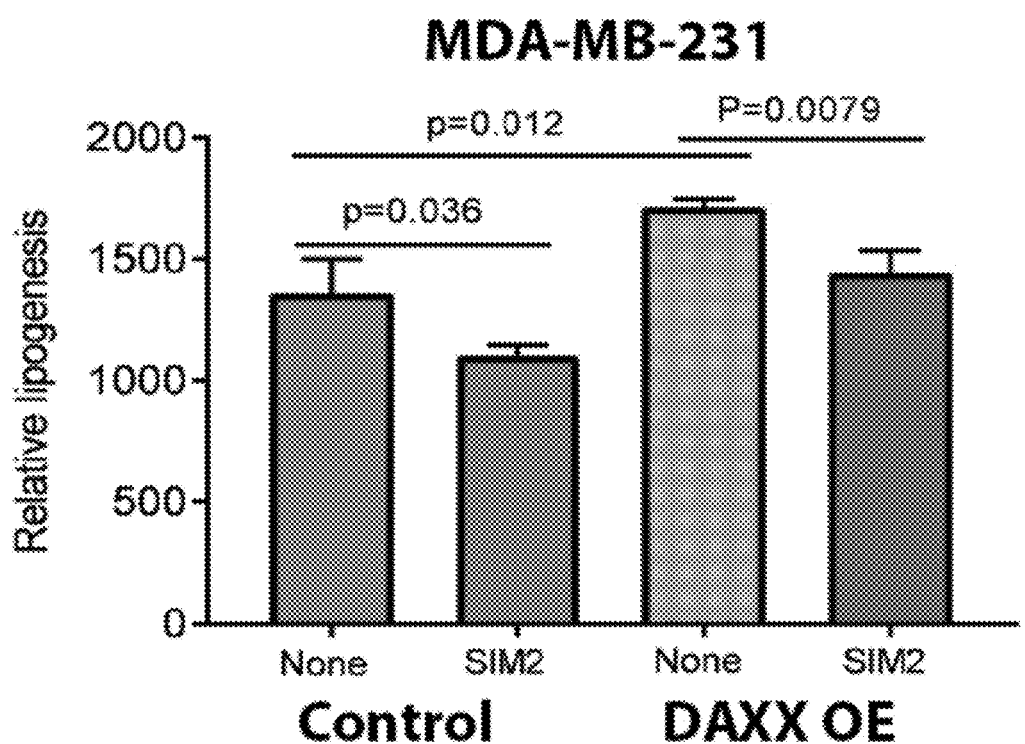
Figure 18D:
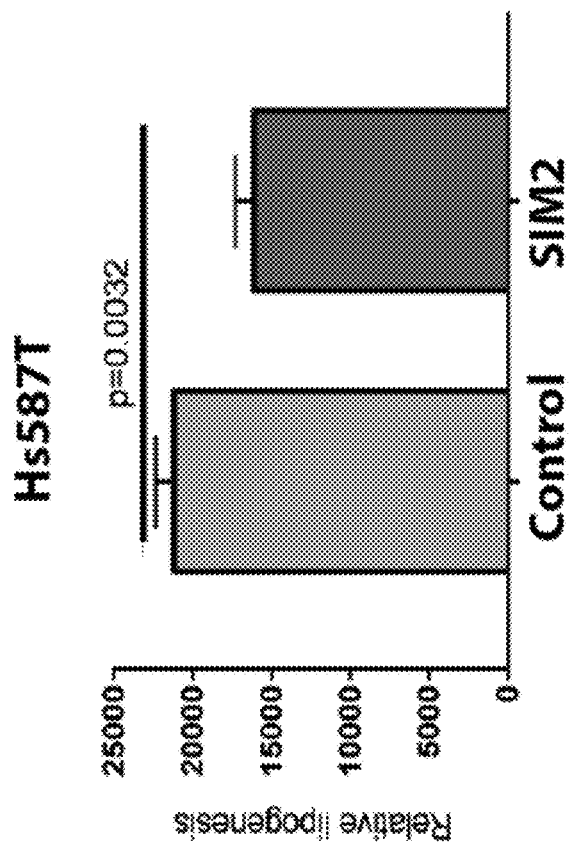
Figure 18D:
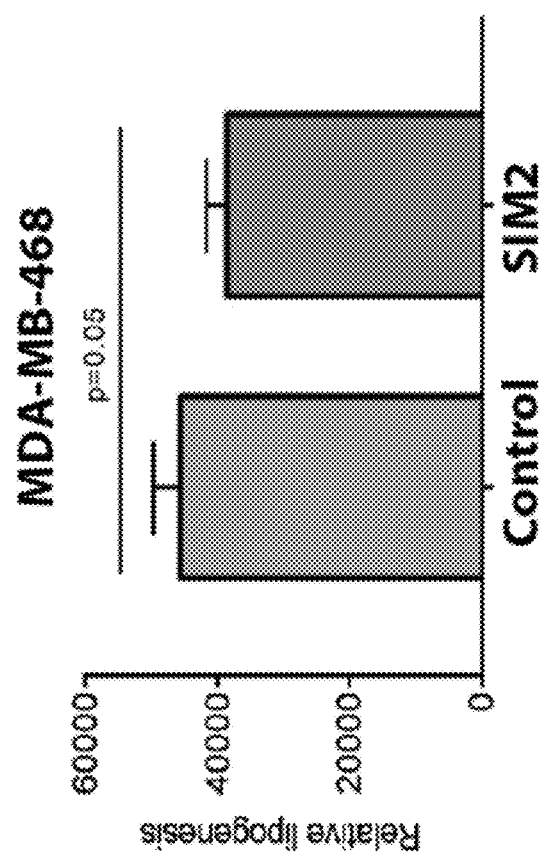
Figure 18E:
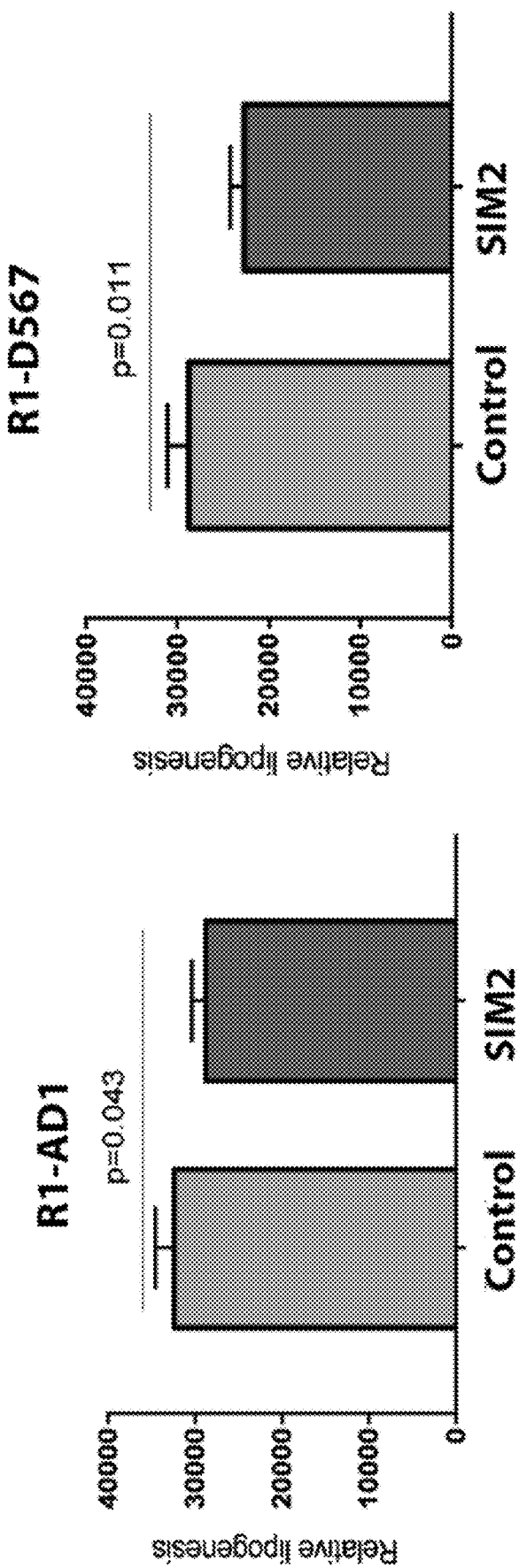
Figure 18F:
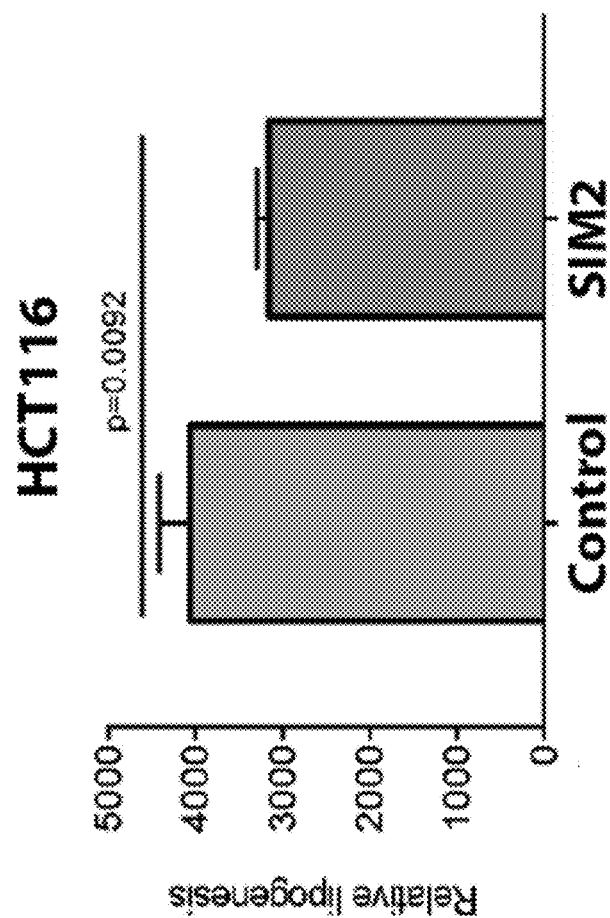
Figure 18H:
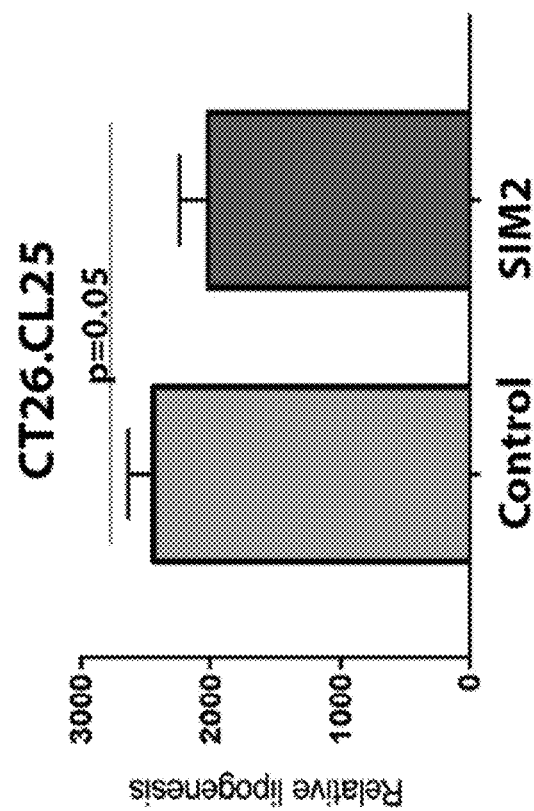
Figure 18G:
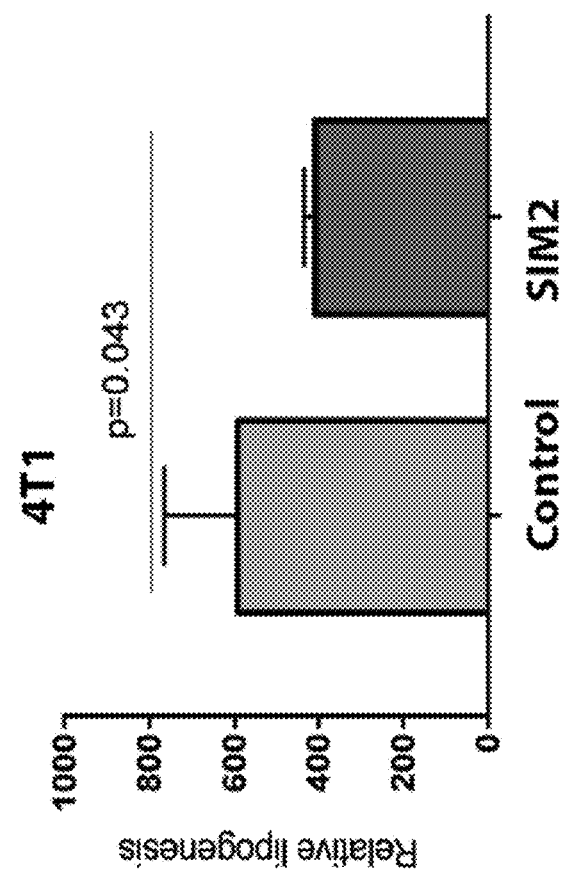
Figure 18I:
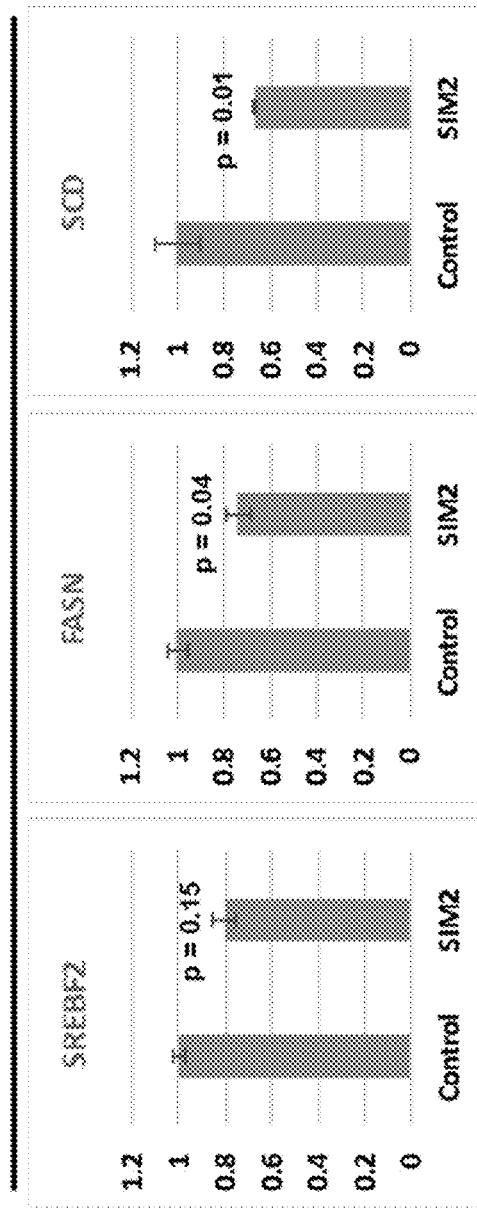
Figure 18I:
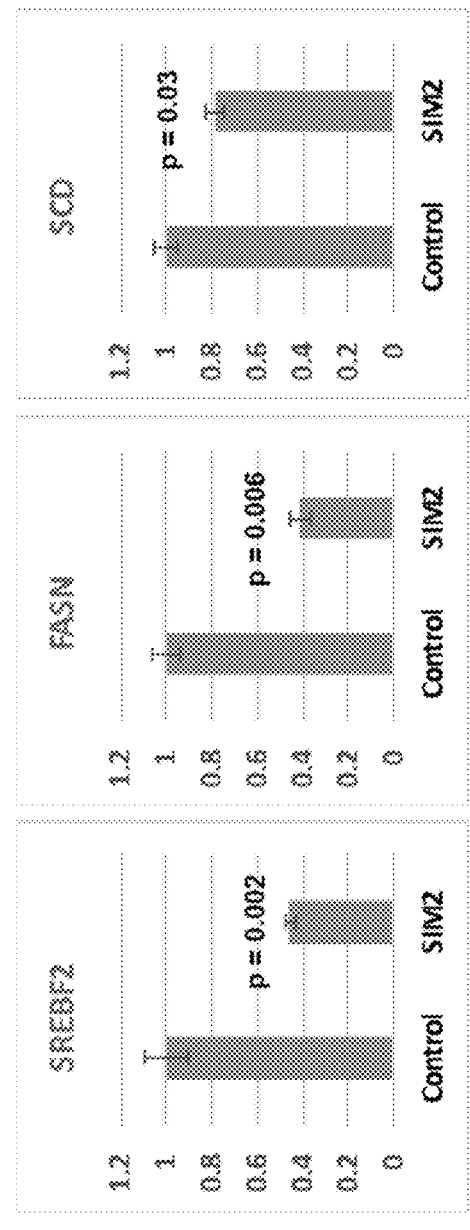

FIGS. 18A to 18I show SIM2 peptide blocks lipogenesis. FIG. 18A shows the DAXX SIM2 peptide is rapidly internalized. MDA-MB-231 and MDA-MB-468 cells were exposed to TAMRA-SIM2 (1 µM) for 1 hour and visualized by microscopy. FIG. 18B shows the SIM2 peptide binds to SUMO1. Fluorescence polarization assay was performed in the presence of TAMRA-SIM2 and increased concentrations of SUMO1. FIGS. 18C-18H show SIM2 blocks de novo lipogenesis in MDA-MB-231 control or DAXX OE (FIG. 18C), MDA-MB-468 (FIG. 18D), Hs578T (FIG. 18E), HCT116 (FIG. 18F), 4T1 (FIG. 18G), and CT26.CL25 (FIG. 18H). Serum-starved cells were not treated (control) or exposed to SIM2 (10 µM) and labeled with [$^{14}$C] acetate. The levels of labeled lipids were quantified. FIG. 18I shows SIM2 inhibits lipogenic gene expression. MDA-MB-231 control and DAXX OE cell lines were untreated (control) or treated with SIM2 (10 µM). At 24 h after treatment, RNA was isolated and subject to qRT-PCR. RNA levels were normalized against that of ACTB. The p values shown are based on t-test.

DETAILED DESCRIPTION

As disclosed herein, DAXX is as a key regulator of cancer lipogenesis pathway. DAXX interacts with SREBPs and is recruited to SREBP-binding chromatin sites. While DAXX depletion impairs, DAXX overexpression promotes lipogenesis and tumor growth. DAXX expression is induced in the absence of exogenous lipid supplies; under which DAXX activates MYC expression through SREBP2. Strikingly, a SUMO-binding defective DAXX mutant could not promote lipogenesis and tumor growth, and a DAXX SIM-derived peptide (SIM2) blocks gene expression, de novo lipogenesis and tumor growth. Thus, the DAXX SIM/SUMO interface represents a tractable therapeutic target with the SIM2 peptide. These studies define a previously unknown oncogenic mechanism underlying cancer biology and a therapeutic approach with translational potential for cancer therapy.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

SIM2 Polypeptide

Disclosed herein is a method for treating cancer in a subject that involves administering to the subject a therapeutically effective amount of a composition comprising a polypeptide that comprises an amino acid sequence corresponding to at the C-terminal SUMO-interacting motif (SIM2) of a DAXX protein. The polypeptide is not a functional DAXX protein. Therefore, in some embodiments, the polypeptide lacks all of part of one or more of the SIM domain, DAXX helical bundle (DHB) domain; histone binding domain (HBD); or PEST domain of the DAXX protein. Therefore, in some embodiments, the polypeptide lacks one or more of amino acids 1-17, 55-144, 180-384, or 500-728. In some embodiments, the polypeptide lacks all of amino acids 1 to 728 of the DAXX protein.

Therefore, in some embodiments, the polypeptide lacks at least 10, 11, 12, 13, 14, 15, 16, 17, 18, 19, 20, 25, 30, 35, 40, 45, 50, 60, 70, 80, 90, 100, 110, 120, 130, 140, 141, 142, 143, 144, 145, 156, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 420, 430, 440, 441, 442, 443, 444, 445, 456, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 525, 626, 527, 628, 629, 630, 631, 632, 633, 634, 635, 636, 637, 638, 639, 640, 641, 642, 643, 644, 645, 646, 647, 648, 649, 660, 661, 662, 663, 664, 665, 666, 667, 668, 669, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, or 728 consecutive amino acids of amino acids 1 to 728 of the DAXX protein.

In some embodiments, the polypeptide comprises or consists of the amino acid sequence DPEEIIVLSDSD (SEQ ID NO:1, SIM2), or a variant thereof, e.g. having one or two conservative amino acid substitutions, that binds SUMO-1. Therefore, in some embodiments, the polypeptide comprises or consists of an amino acid sequence selected from the group comprising DPDDIIVLSDSD (SEQ ID NO:2, SIM008), DPEEIIVLSESE (SEQ ID NO:3, SIM009), DPEEIIVLDDDD (SEQ ID NO:4, SIM010), DPEEKIVLSDSD (SEQ ID NO:5, SIM011), DPEEI-IDLSDSD (SEQ ID NO:6, SIM012), EPEEIIVLSDSD (SEQ ID NO:7, SIM013), and IIVLSDS (SEQ ID NO:8, SIM014). In some embodiments, the polypeptide comprises the amino acid sequence $X_1PX_2X_3X_4X_5X_6X_7X_8X_9X_{10}X_{11}$ (SEQ ID NO:9), wherein $X_1$ is D or E, $X_2$ is E or D, $X_3$ is E or D, $X_4$ is I, V or L, $X_5$ is I, V, or L, $X_6$ is V, I, or L, $X_7$ is L, I, or V, $X_8$ is S, T, E or D, $X_9$ is D or E, $X_{10}$ is S, T, E or D, AND $X_{11}$ is D or E.

In some embodiments, the disclosed polypeptide is a peptidomimetic. As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The disclosed composition can be linked to an internalization sequence or a protein transduction domain to effectively enter the cell. Recent studies have identified several cell penetrating peptides, including the TAT transactivation domain of the HIV virus, antennapedia, and transportan that can readily transport molecules and small peptides across the plasma membrane (Schwarze et al., Science. 1999 285 (5433):1569-72; Derossi et al. J Biol Chem. 1996 271(30): 18188-93; Yuan et al., Cancer Res. 2002 62(15):4186-90). More recently, polyarginine has shown an even greater efficiency of transporting peptides and proteins across the plasma, membrane making it an attractive tool for peptide mediated transport (Fuchs and Raines, Biochemistry. 2004 43(9):2438-44). Nonaarginine has been described as one of the most efficient polyarginine based protein transduction domains, with maximal uptake of significantly greater than TAT or antennapeadia. Peptide mediated cytotoxicity has also been shown to be less with polyarginine-based internalization sequences. $R_9$ mediated membrane transport is facilitated through heparan sulfate proteoglycan binding and endocytic packaging. Once internalized, heparan is degraded by heparanases, releasing $R_9$ which leaks into the cytoplasm (Deshayes et al., Cell Mol Life Sci. 2005 62(16): 1839-49). Studies have recently shown that derivatives of polyarginine can deliver a full length p53 protein to oral cancer cells, suppressing their growth and metastasis, defining polyarginine as a potent cell penetrating peptide (Takenobu et al., Mol Cancer Ther. 2002 1(12):1043-9). Thus, the provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In some embodiments, the polypeptide is a chimeric molecule comprising a "targeting molecule" or "targeting moiety." A targeting molecule is a molecule such as a ligand or an antibody that specifically binds to its corresponding target, for example a receptor on a cell surface. Thus, for example, where the targeting molecule is a ligand, the chimeric molecule will specifically bind (target) cells and tissues bearing expressing the receptor for that ligand.

Pharmaceutical Compositions

Also disclosed is a composition comprising the disclosed polypeptide in a pharmaceutically acceptable excipient. Pharmaceutical carriers suitable for administration of the compounds provided herein include any such carriers known to those skilled in the art to be suitable for the particular mode of administration. The polypeptides can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the polypeptides described above are formulated into pharmaceutical compositions using techniques and procedures well known in the art (See, e.g., Ansel, Introduction to Pharmaceutical Dosage Forms, 4th Edition, 1985, 126).

In addition, the compounds may be formulated as the sole pharmaceutically active ingredient in the composition or may be combined with other active ingredients. For example, the compounds may be formulated or combined with known NSAIDs, anti-inflammatory compounds, steroids, and/or antibiotics.

In one embodiment, the compositions are formulated for single dosage administration. To formulate a composition, the polypeptide is dissolved, suspended, dispersed or otherwise mixed in a selected carrier at an effective concentration such that the treated condition is relieved or one or more symptoms are ameliorated.

In some embodiments, the peptide is formulated in a suitable peptide-delivery nanoparticle, such as encapsulated within nanoparticles of poly(lactide-co-glycolide) copolymer, cyclodextrin nanoparticles, or cetyl alcoholipolysorbate.

Peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. For example, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane.

To ensure full gastric resistance a coating can be impermeable to at least pH 5.0. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The peptides could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

To aid dissolution of peptides into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

In some embodiments, the polypeptide is encapsulated in a biocompatible nanoparticle. In particular embodiments, the polypeptide is formulated in a vehicle containing about 33% 2-Hydroxypropyl)-8-cyclodextrin (HPBCD) in PBS and about 45% polyethylene glycol 400.

Cancer Treatment

The cancer of the disclosed methods can be any cell in a subject undergoing unregulated growth, invasion, or metastasis. In some aspects, the cancer is breast cancer, prostate cancer, or colon cancer. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed polypeptides can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed polypeptides can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

In one embodiment, the disclosed polypeptide compositions are administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of polypeptide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Although the polypeptide compositions may be administered once or several times a day, and the duration of the treatment may be once per day for a period of about 1, 2, 3, 4, 5, 6, 7 days or more, it can be more preferably to administer either a single dose in the form of an individual dosage unit or several smaller dosage units or by multiple administration of subdivided dosages at certain intervals. For instance, a dosage unit can be administered from about 0 hours to about 1 hr, about 1 hr to about 24 hr, about 1 to about 72 hours, about 1 to about 120 hours, or about 24 hours to at least about 120 hours. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours. Subsequent dosage units can be administered any time following the initial administration such that a therapeutic effect is achieved.

A number of embodiments of the invention have been described. Nevertheless, it will be understood that various modifications may be made without departing from the spirit and scope of the invention. Accordingly, other embodiments are within the scope of the following claims.

EXAMPLES

Example 1

DAXX Drives De Novo Lipogenesis and Represents a Novel Therapeutic Target for Cancer Therapy Introduction Cancer cells exhibit elevated de novo intracellular lipogenesis, resulting in increased levels of fatty acids, membrane phospholipids, and cholesterol (Rohrig F, et al. Nat Rev Cancer 2016 16(11):732-49). Obesity and hypercholesterolemia are known cancer risk factors (Boyd N F, et al. J Natl Cancer Inst 1990 82(6):460-8). Notably, de novo lipogenesis contributes minimally to the overall lipid content of normal non-proliferating cells, which generally rely on the uptake of lipids from the circulation. Increased de novo lipogenesis in cancer cells is thought to supply lipids for the synthesis of membranes and signaling molecules during rapid cell proliferation and tumor growth, due to limited availability of lipids from the circulation in the tumor microenvironment ((Rohrig F, et al. Nat Rev Cancer 2016 16(11):732-49; Lewis C A, et al. Oncogene 2015 34(40): 5128-40). Thus, targeting de novo lipogenesis may be an effective strategy for cancer therapy. Indeed, epidemiological studies have shown that the use of statins, which inhibit 3-hydroxy-3-methylglutaryl-CoA reductase (HMGCR)—the rate-limiting enzyme in cholesterol synthesis via the mevalonate pathway—appears to provide survival benefits for some breast cancer (BC) patients (Shaitelman S F, et al. J Cancer 2017 8(11):2026-32). Statins have antiproliferative and apoptotic effects in BC cells in tissue cultures and tumor specimens obtained from patients treated with statins (Freed-Pastor W A, et al. Cell 2012 148(1-2):244-58; Ricoult S J, et al. Oncogene 2016 35(10):1250-60; Pandyra A A, et al. Oncotarget 2015 6(29):26909-21; Wang T, et al. Oncotarget 2016 7(3):2532-44), suggesting that this classic metabolic pathway is intrinsically active within tumor cells for cell survival, proliferation and tumor growth (Mullen P J, et al. Nat Rev Cancer. 2016 16(11):718-731). Significantly, heightened cholesterol production is linked to treatment resistance and poor prognosis (Simigdala N, et al. Breast Cancer Res 2016 18(1):58). Certain cholesterol metabolites such as 25- and 27-hydroxycholesterol (25-HC and 27-HC) are partial ligands for estrogen receptor-α (ER) and have been shown to promote ER-mediated transcription, enhance tumor growth and confer treatment resistance (Simigdala N, et al. Breast Cancer Res 2016 18(1):58; Nelson ER, et al. Science 2013 342(6162):1094-8). Recent works also show that 27-HC appears to promote BC metastatic progression (Baek A E, et al. Nat Commun 2017 8(1):864).

Lipogenesis is controlled by several transcription factors, such as the sterol regulatory element-binding proteins, SREBP1 and SREBP2 (collectively referred to as SREBP1/2), that have also been shown to play an important role in maintaining lipid synthesis in cancer (Griffiths B, et al. Cancer Metab 2013 1(1):3). SREBP1/2 precursors are sequestered in endoplasmic reticulum. When sterol supply is low, SREBP1/2 are transported to the Golgi apparatus where they are cleaved by proteases, and the N-terminal domain of SREBPs are then released and imported into the nucleus to promote transcription of genes that contain the sterol regulatory elements (SREs) required for lipogenesis. Oncogenic drivers such as KRAS, PI3K and mTOR have been shown to promote de novo lipogenesis in breast and other cancers (Rohrig F, et al. Nat Rev Cancer 2016 16(11):732-49; Ricoult S J, et al. Oncogene 2016 35(10):1250-60; Guo D, et al. Sci Signal 2009 2(101):ra82). For example, mTOR promotes lipogenesis through stabilizing SREBP1/2 by opposing phosphorylation-dependent poly-ubiquitination by the E3 ubiquitin ligase FBXW7 and subsequent proteasomal degradation (Sundqvist A, et al. Cell Metab 2005 1(6):379-91). Notably, tumors efficiently convert acetate to acetyl-CoA (Comerford S A, et al. Cell 2014 159(7):1591-602), which is predominantly used for lipid synthesis (Bulusu V, et al. Cell Rep 2017 18(3):647-58), highlighting the need for cancer cells to produce lipogenic enzymes (Gao X, et al. Nat Commun 2016 7:11960). While the dependence on de novo lipogenesis in cancer is well documented, the mechanisms that control SREBP-mediated transcription underlying oncogenic de novo lipogenesis remain poorly understood.

DAXX, originally discovered as a context-dependent regulator of cell death or survival (Yang X L, et al. Cell 1997 89(7):1067-76; Michaelson J S, et al. Genes Dev 1999 13(15):1918-23), has an extensively documented role in transcriptional regulation through interacting with transcription factors including p53 (Zhao L Y, et al. J Biol Chem 2004 279(48):50566-79) and NF-κB (Puto L A, et al. Genes Dev 2008 22(8):998-1010). DAXX is a small ubiquitin-related modifier (SUMO)-binding protein via two SUMO-interacting motifs (SIMs) and that the SUMO-binding property of DAXX appears critical for it to regulate transcription (Santiago A, et al. Cell Cycle 2009 8(1):76-87; Chang C C, et al. Mol Cell 2011 42(1):62-74; Lin D Y, et al. Mol Cell 2006 24(3):341-54). More recent studies have defined DAXX as a specific chaperone for the histone variant H3.3 (Lewis P W, et al. Proc Natl Acad Sci USA 2010 107(32):14075-80; Goldberg A D, et al. Cell 2010 140(5):678-91; Drane P, et al. Genes Dev 2010 24(12):1253-65). DAXX binds specifically to the H3.3/H4 dimer and deposits it onto chromatin (Elsasser S J, et al. Nature 2012 491(7425):560-5; Liu C P, et al. Nat Struct Mol Biol 2012 19(12):1287-92). Emerging evidence suggests that DAXX has an oncogenic role in diverse cancer types (Pan W W, et al. J Biol Chem 2013 288(19):13620-30; Puto L A, et al. J Biol Chem 2015 290(25):15406-20), which appears to be linked to its functions in gene regulation (Puto L A, et al. J Biol Chem 2015 290(25):15406-20; Benitez J A, et al. Nat Commun 2017 8:15223). Whereas the levels of DAXX expression directly correlate with its ability to promote tumor growth (Pan W W, et al. J Biol Chem 2013 288(19):13620-30; Puto L A, et al. J Biol Chem 2015 290(25):15406-20; Benitez J A, et al. Nat Commun 2017 8:15223), the molecular mechanisms underlying DAXX's oncogenic function remain to be defined. Of critical importance is to understand whether DAXX is a tractable therapeutic target for cancer therapy.

In this Example, DAXX was identified as a key regulator of cancer lipogenesis pathway, through interacting with SREBPs, thereby activating lipogenic gene expression programs mediated by SREBPs and promoting cancer cell proliferation in vitro and tumor growth in vivo. Strikingly, a SUMO-binding defective DAXX mutant could not stimulate lipogenesis and tumor growth, and a DAXX SIM-derived peptide (SIM2) blocks DAXX-SREBP interactions, lipogenic gene expression, de novo lipogenesis and tumor growth. Thus, the DAXX SIM/SUMO interface represents a tractable therapeutic target with the SIM2 peptide. Disclosed herein is a previously unknown oncogenic mechanism underlying cancer biology and a novel therapeutic approach with translational potential for cancer therapy.

Results

Figure 1A:
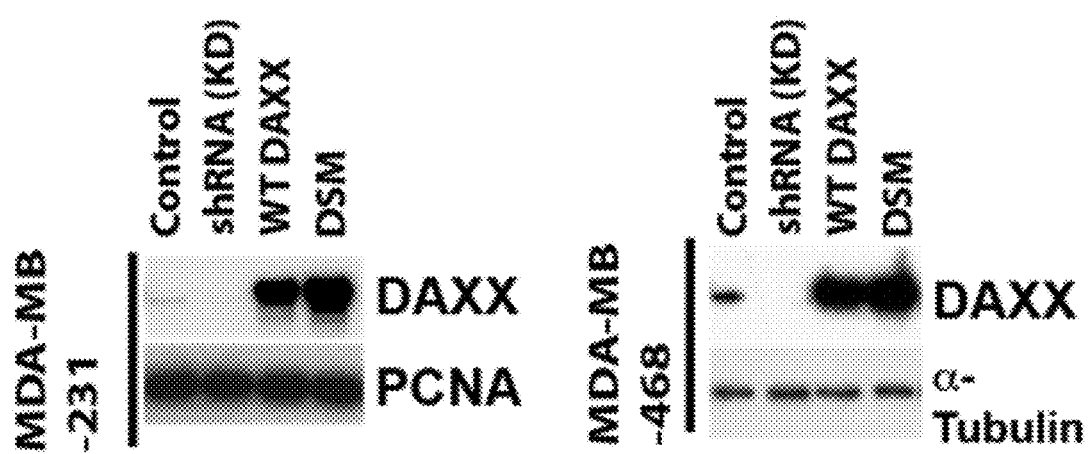
FIGS. 1A to 1I show DAXX regulates the SREBP lipogenesis pathway.
Figure 1B:
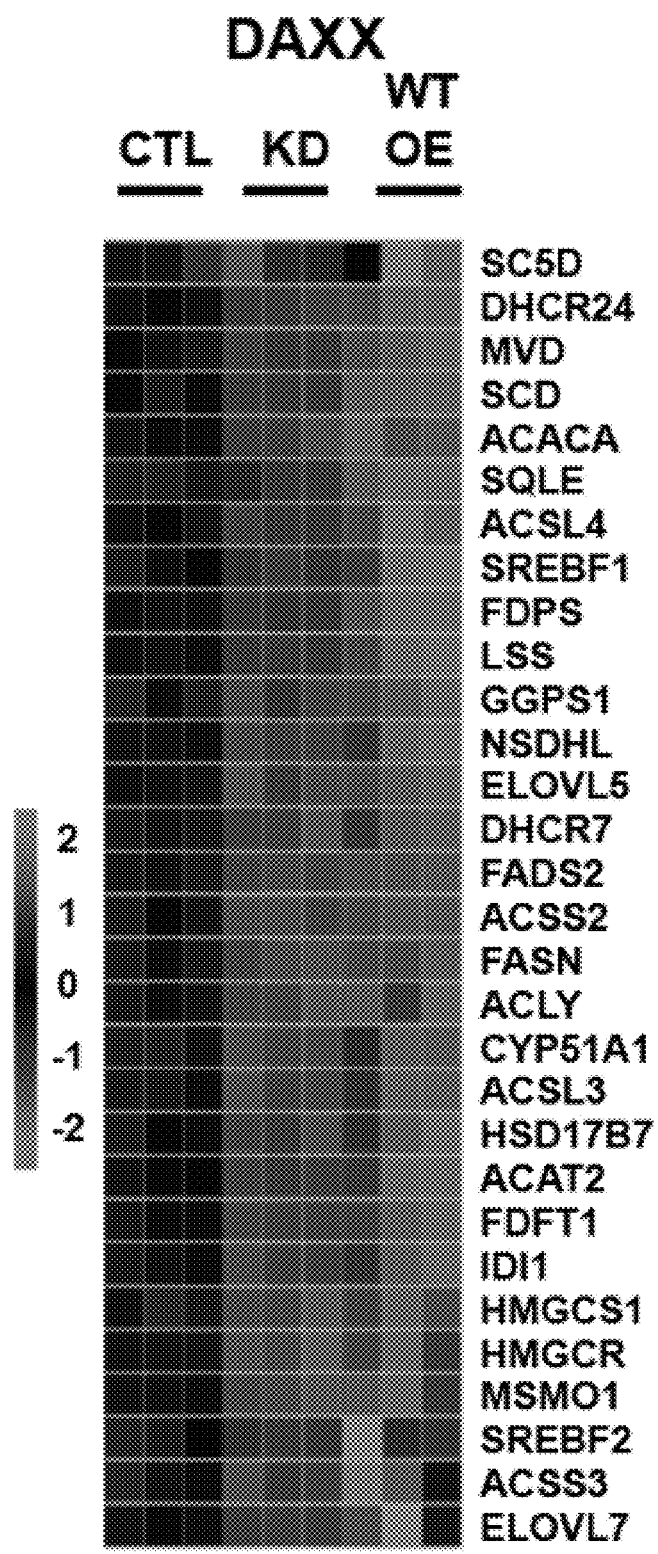
Figure 1C:
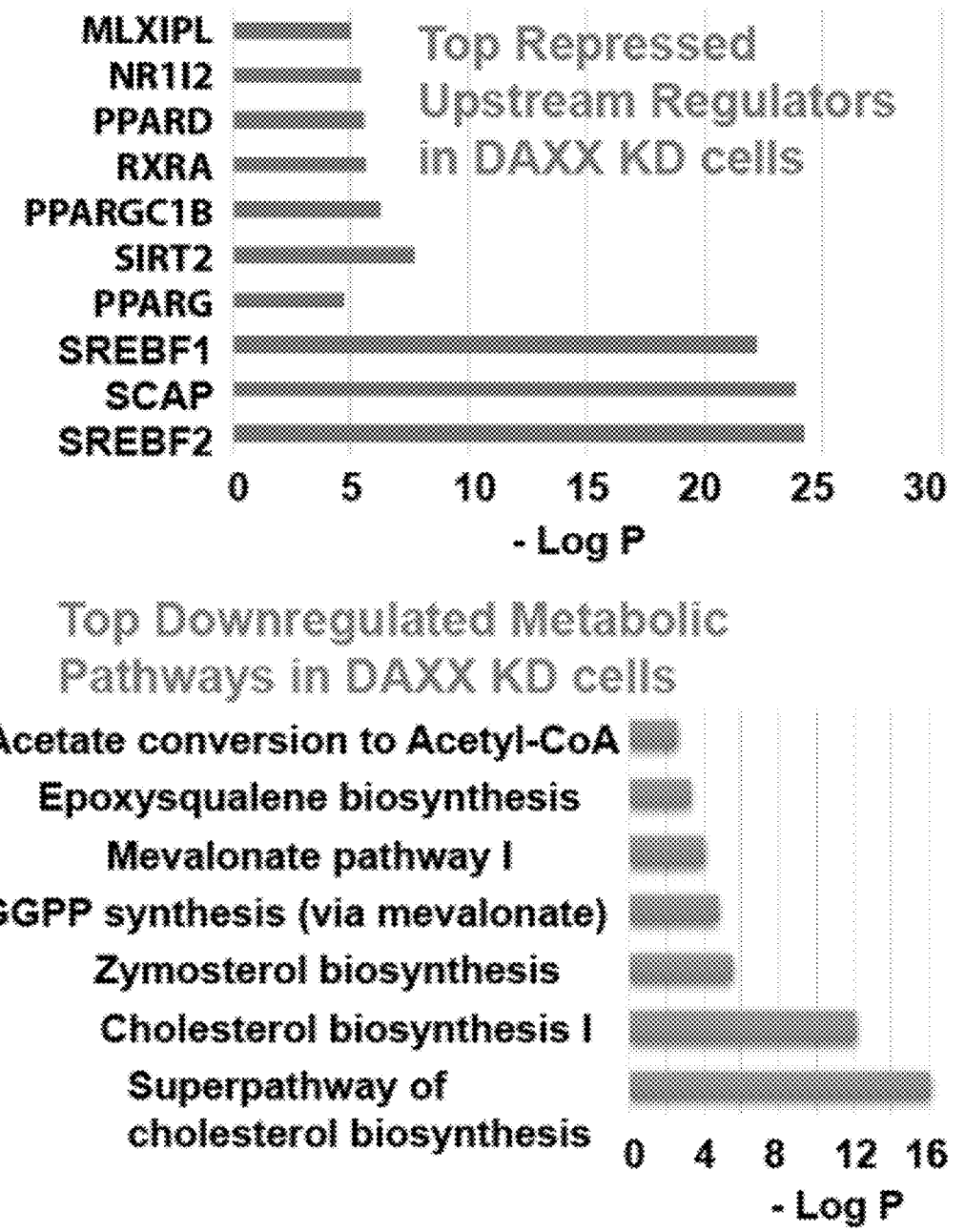
Figure 1D:
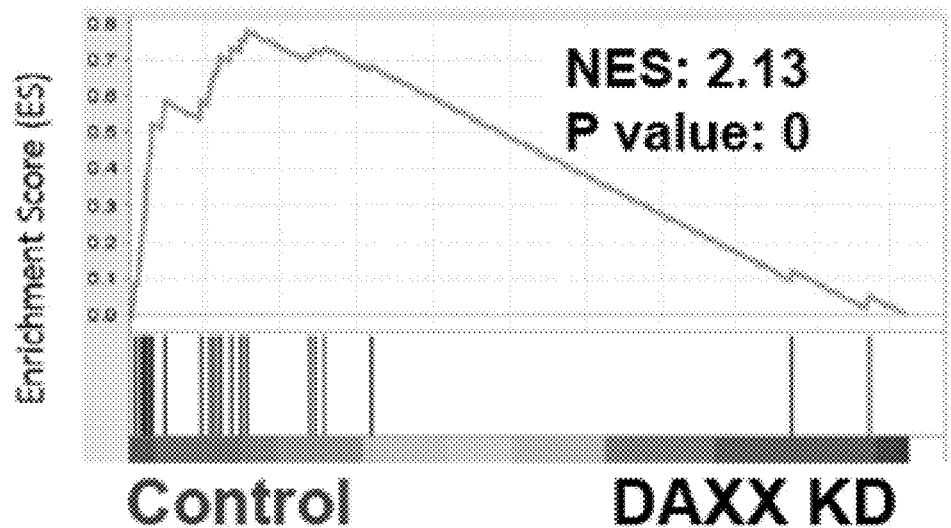
Figure 1D:
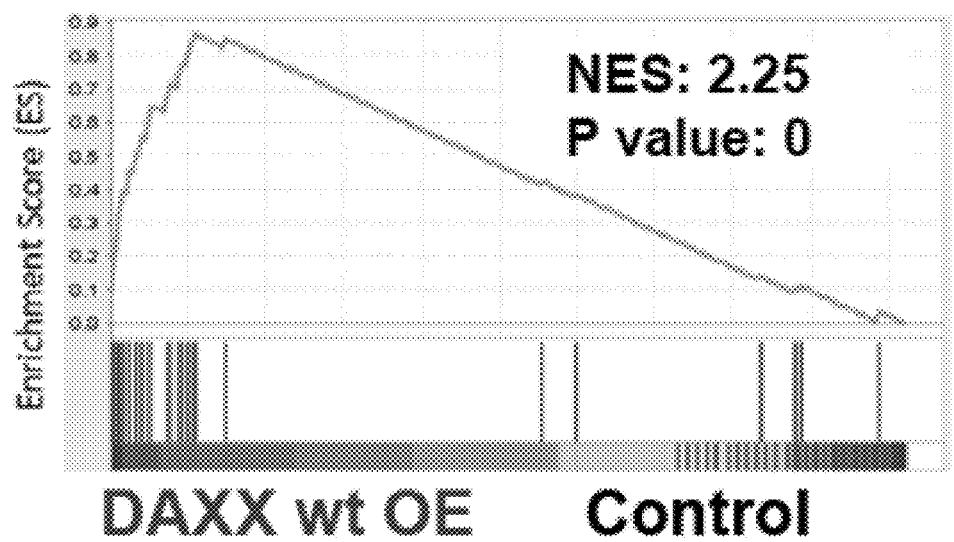
Figure 1E:
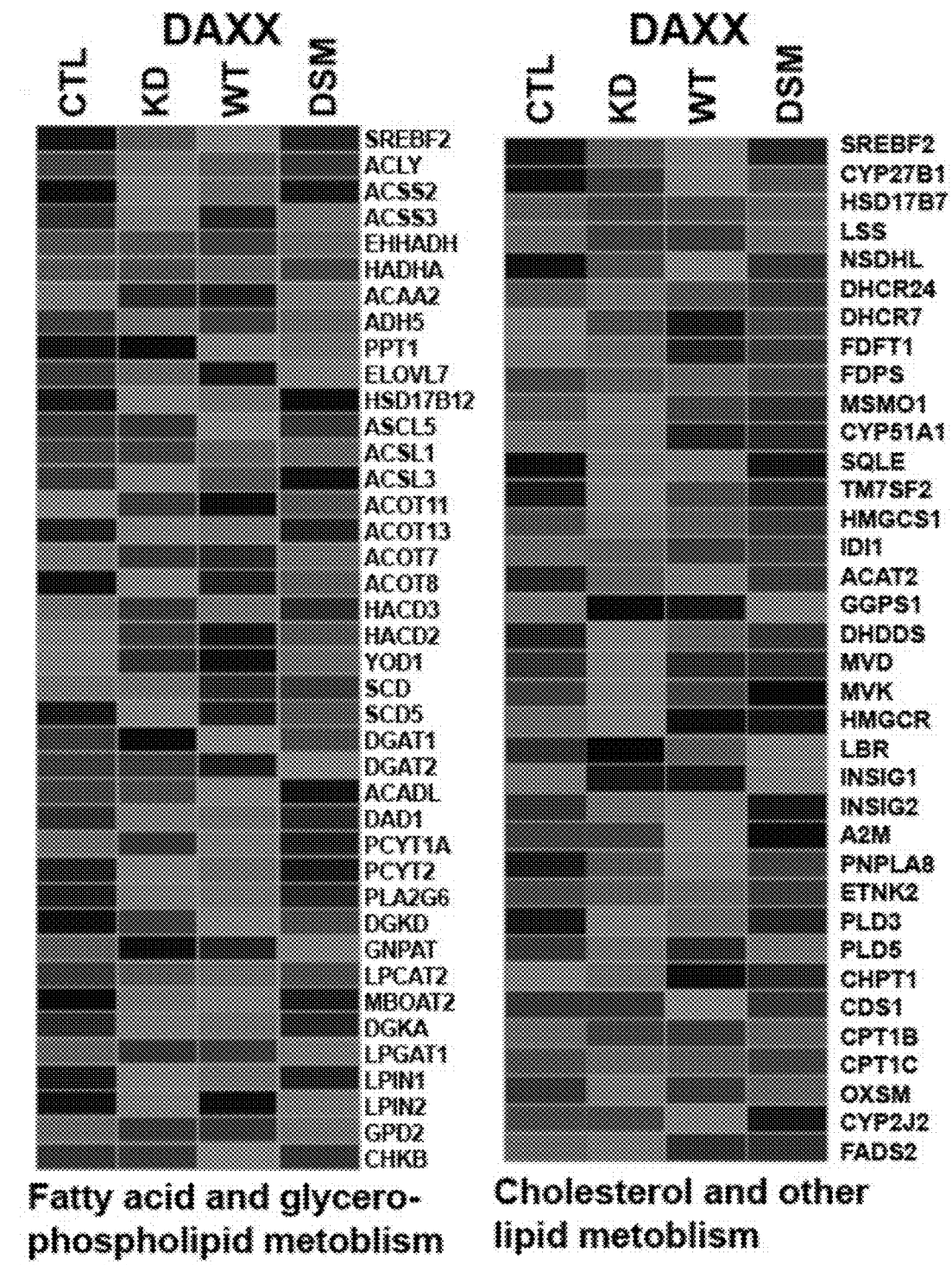
Figure 9A:
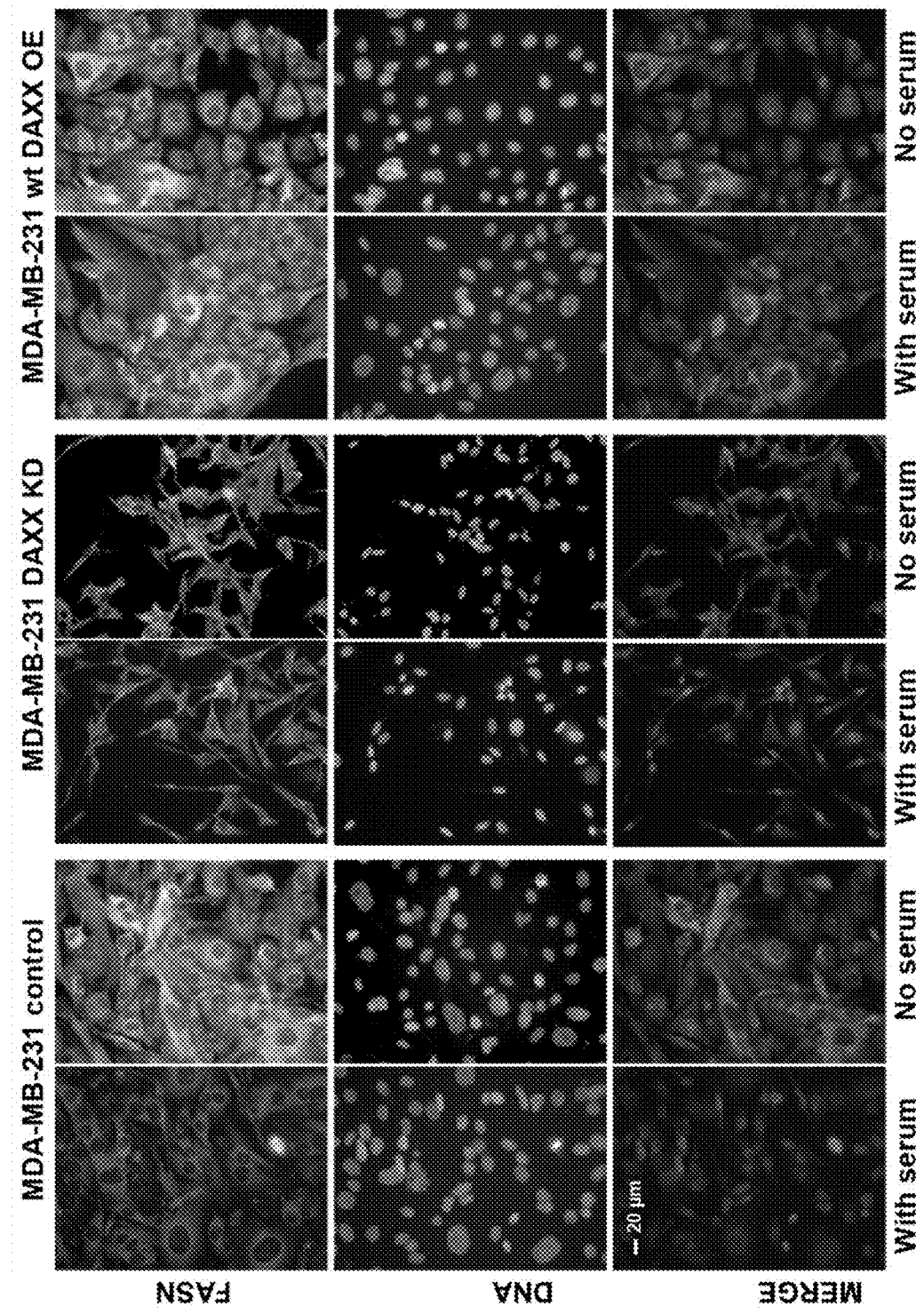
FIGS. 9A to 9E show DAXX promotes the de novo lipogenic program.
Figures 9B, 9C:
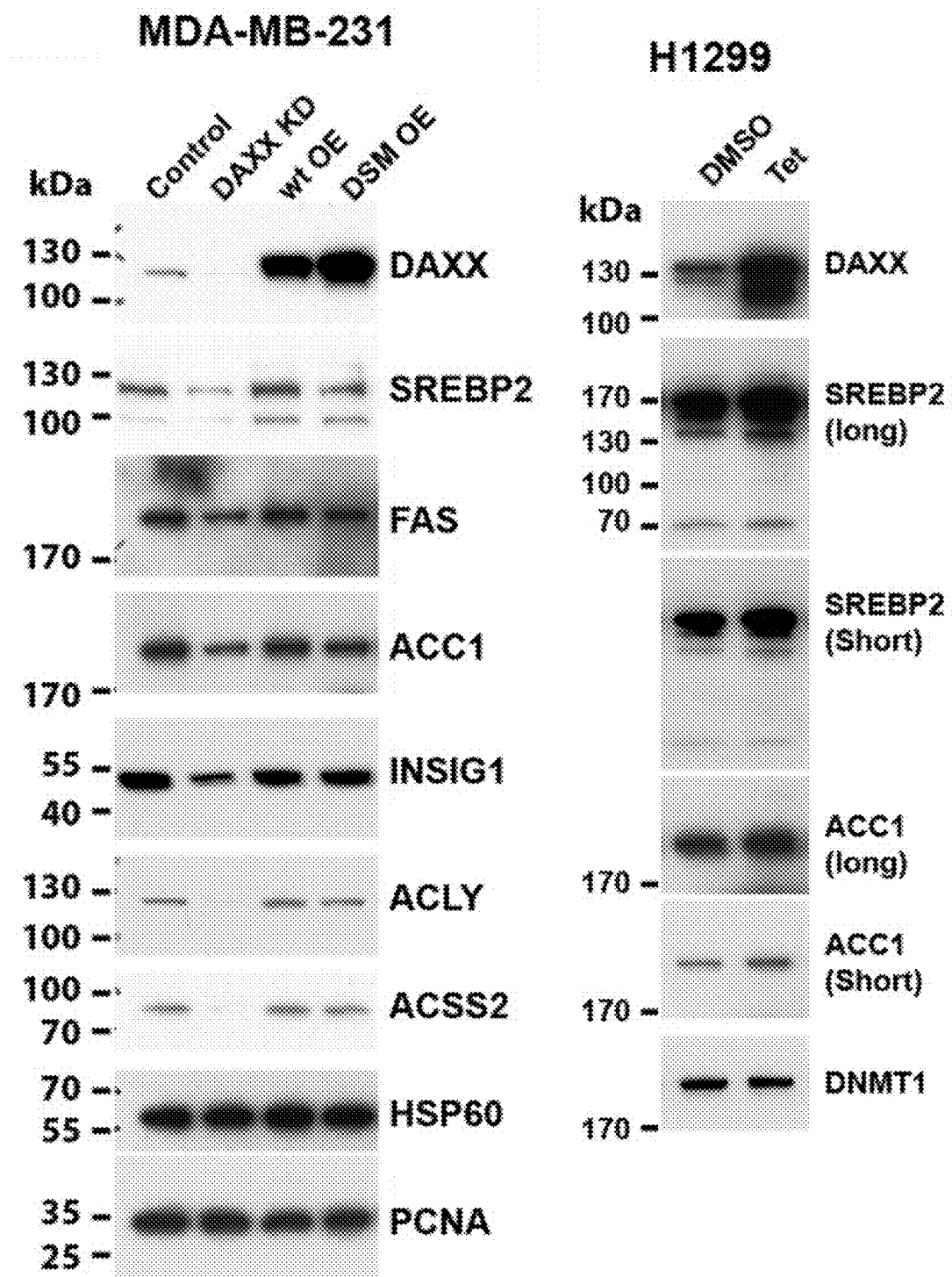
Figure 9D:
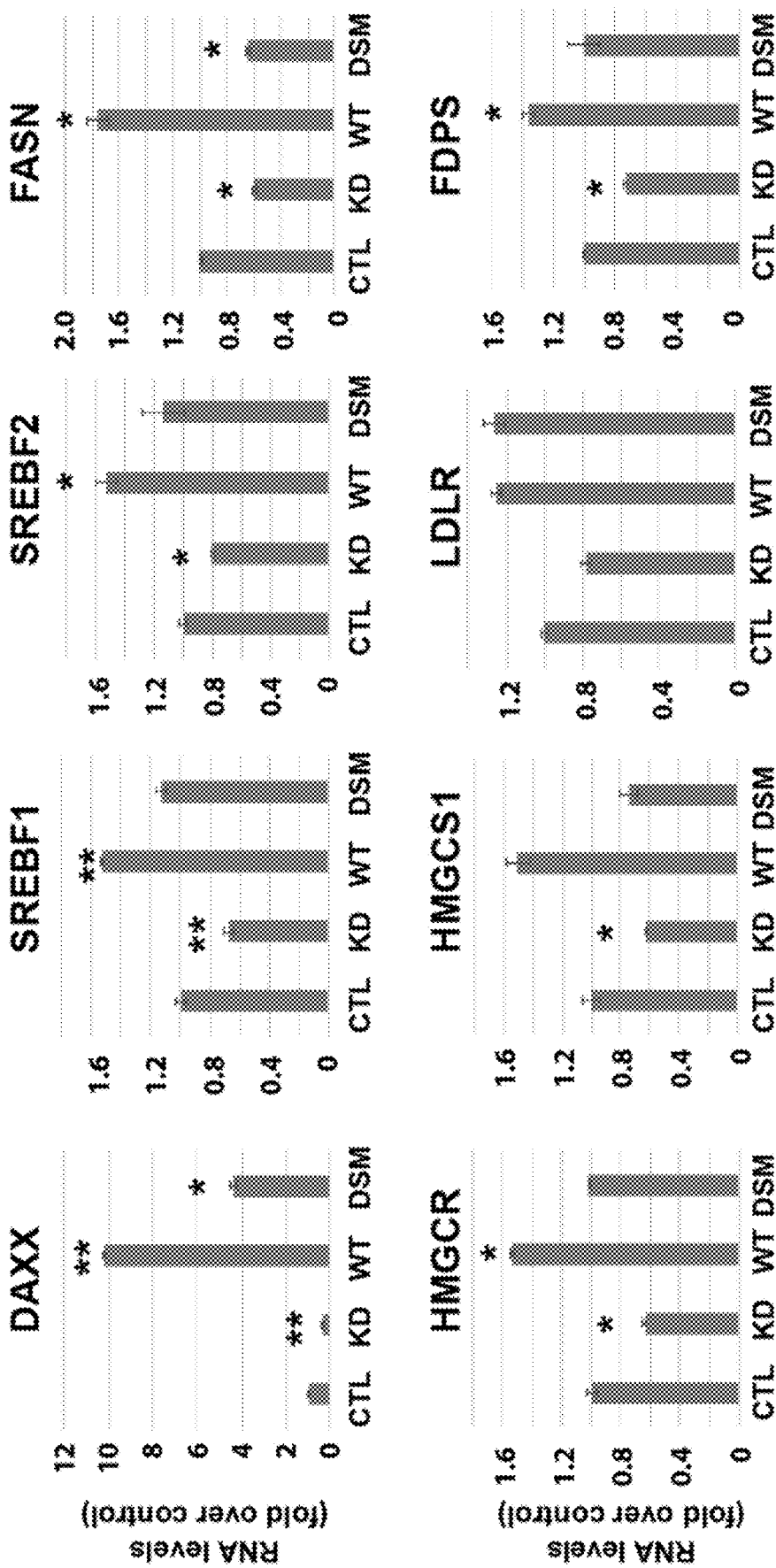

DAXX Expression Levels Dictate Lipogenic Gene Expression and De Novo Lipogenesis Bioinformatic analyses of clinical BC samples revealed that DAXX mRNA levels are elevated in all four major BC subtypes and correlate with poor prognosis (FIG. 8). Consistently, the levels of cholesterols and other lipids are higher in BC samples compared to normal controls (FIG. 8D). To understand potential oncogenic function of DAXX, DAXX was genetically depleted and overexpressed in the BC cell lines MDA-MB-231 and MDA-MB-468 (FIG. 1A). Microarray-based RNA profiling and Ingenuity Pathway Analysis (IPA) of differentially expressed genes between cells with DAXX depletion and control cells revealed a marked downregulation of the de novo lipogenesis pathway (FIG. 1B-1E). Lipogenesis regulators (SREBF1/2 and SOAP) were among the most highly inhibited "upstream regulators." Likewise, the cholesterol, mevalonate and other metabolic pathways related to lipogenesis were also markedly downregulated (FIGS. 1B and 1C). Effects of DAXX overexpression on lipogenesis and observed marked upregulation of lipogenic genes was then assessed (FIGS. 1B, 1D and 1E). Gene Set Enrichment Analysis (GSEA) of mRNA microarray data confirmed suppression and activation of the de novo lipogenesis pathway by genetic DAXX knockdown (KD) and wt cDNA overexpression (wt OE), respectively (FIG. 1D). The impact of DAXX knockdown or overexpression on lipogenic gene expression was further validated by immunofluorescence microscopy (FIG. 9A), immunoblotting (FIG. 9B), and qRT-PCR (FIG. 9D). Using a tetracycline-inducible gene expression system, it was found that DAXX induction increased lipogenic gene expression (FIG. 9C), suggesting that DAXX directly activates lipogenic gene expression.

Figure 1F:
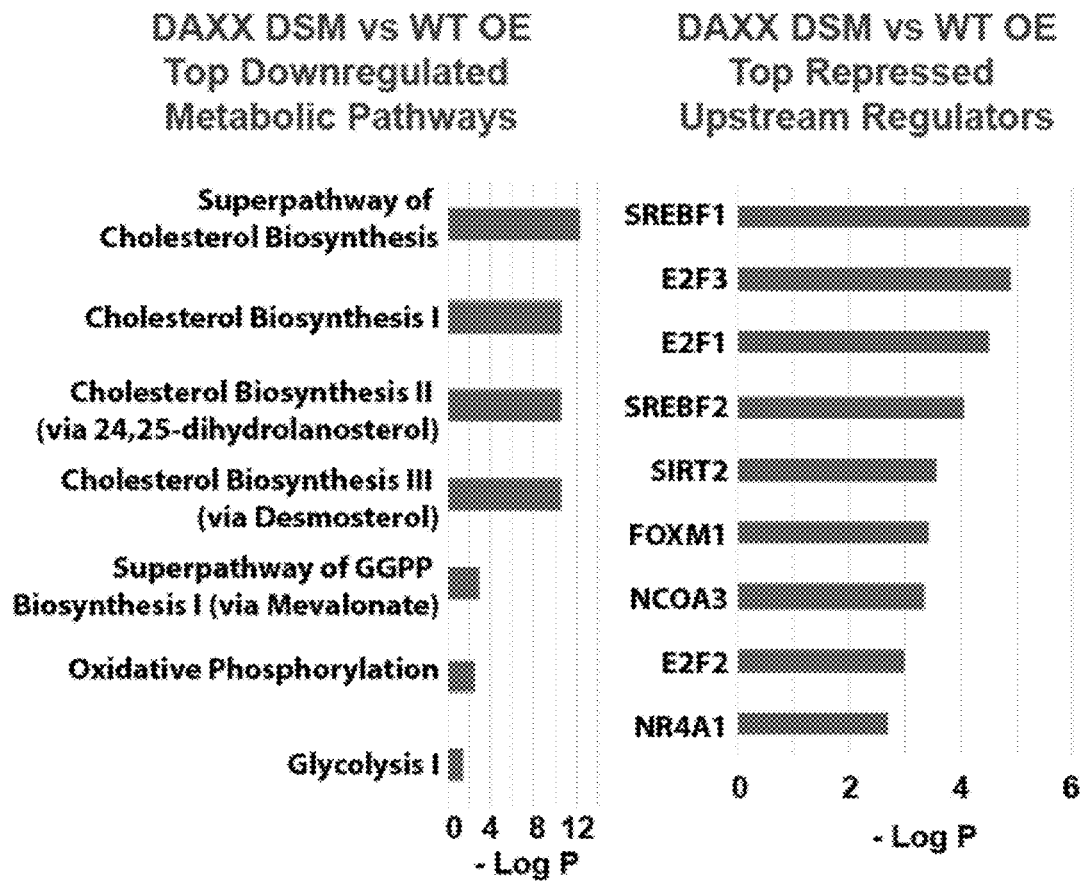
Figure 9E:
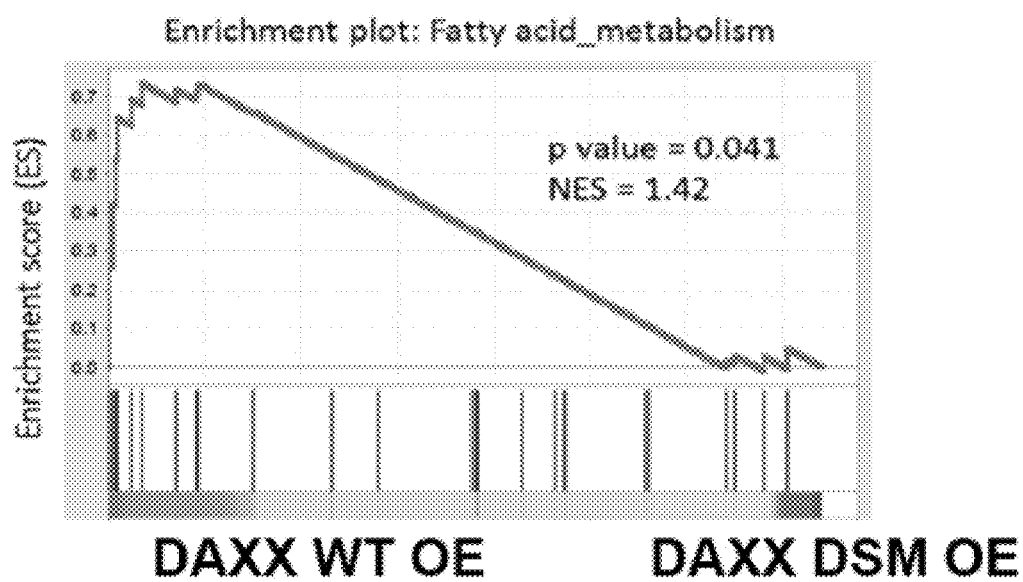
Figure 9E:
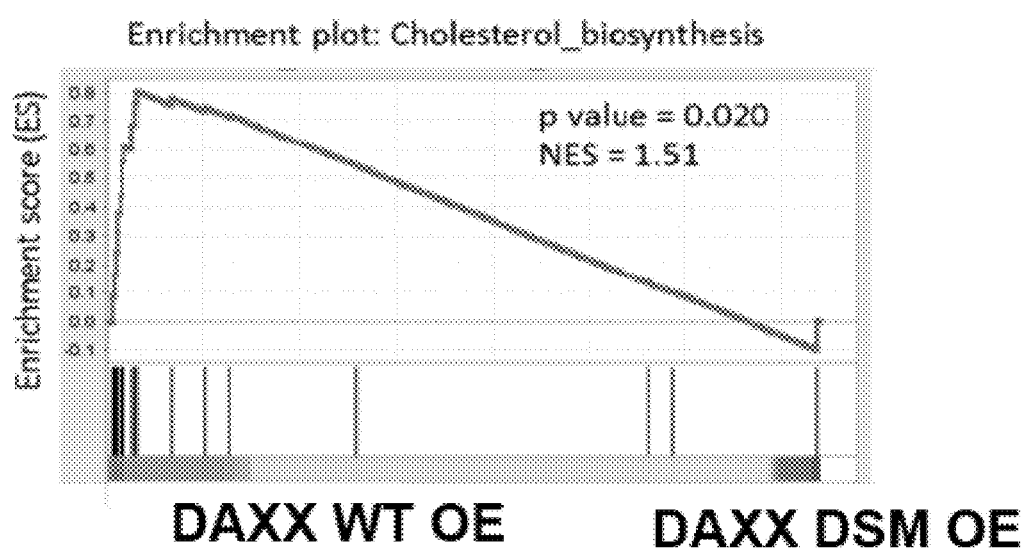

Two SIMs in DAXX have been identified and both SIMs are critical for DAXX to activate transcription (Santiago A, et al. Cell Cycle 2009 8(1):76-87; Chang C C, et al. Mol Cell 2011 42(1):62-74; Lin D Y, et al. Mol Cell 2006 24(3):341-54). Remarkably, the overexpression of the DAXX mutant with the 17K/1733K double mutation that prevents DAXX from binding to SUMO (DAXX double-SIM mutant or DSM) (Santiago A, et al. Cell Cycle 2009 8(1):76-87) was impaired to activate the lipogenic genes (FIG. 1E). An analysis of gene expression data of MDA-MB-231 wt DAXX and DSM OE cells using IPA revealed that the DSM mutant could not promote lipogenesis and activate SREBPs (FIG. 1F; FIG. 9E).

Figure 1G:
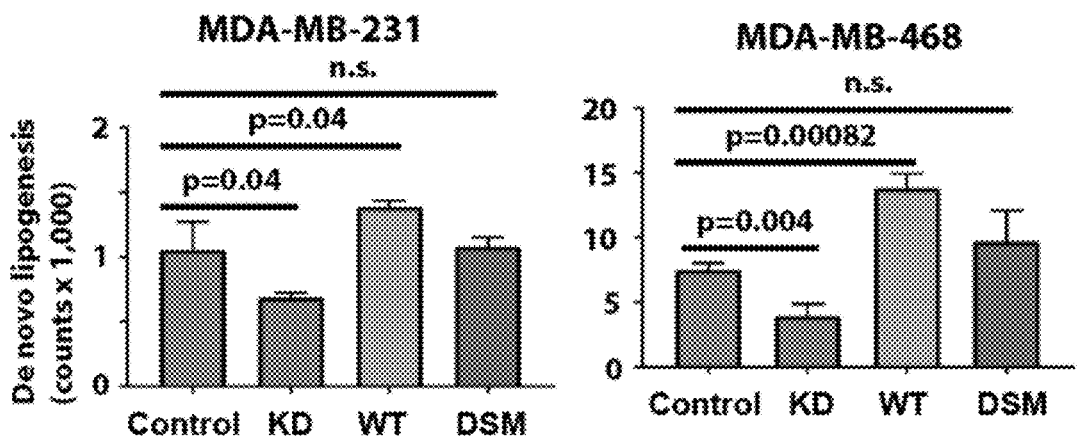
Figure 1H:
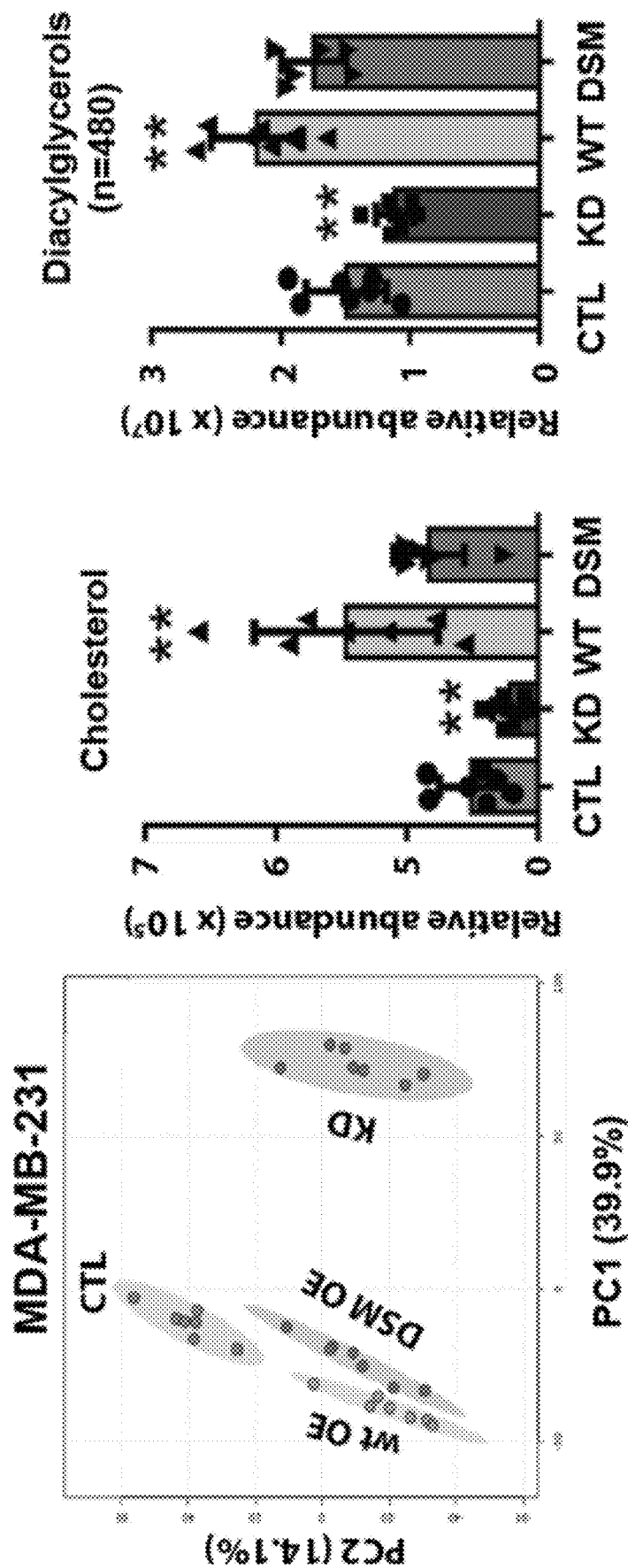
Figure 1I:
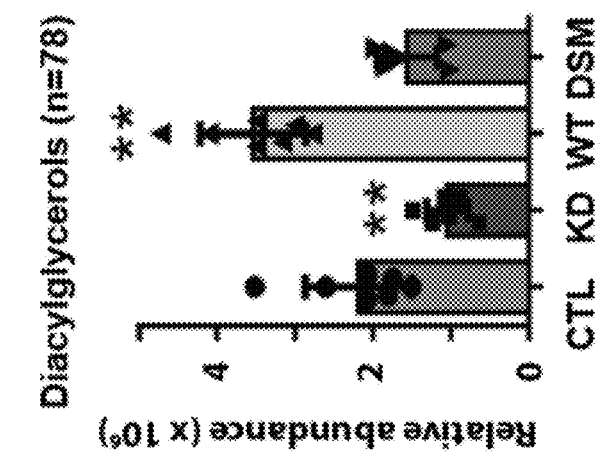
Figure 1I:
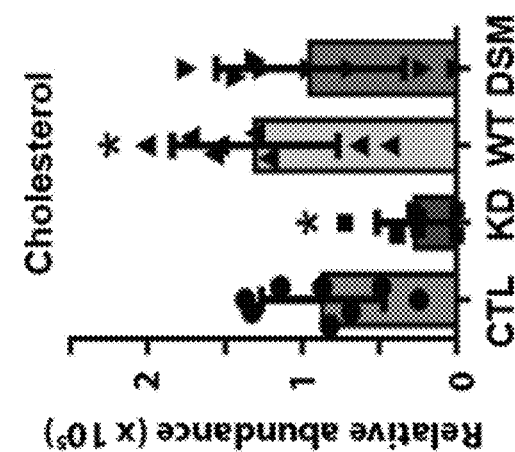
Figure 1I:
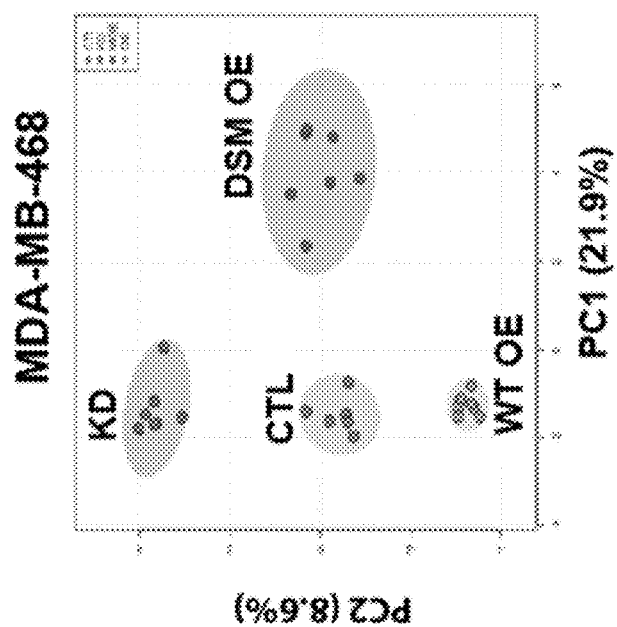
Figure 10A:
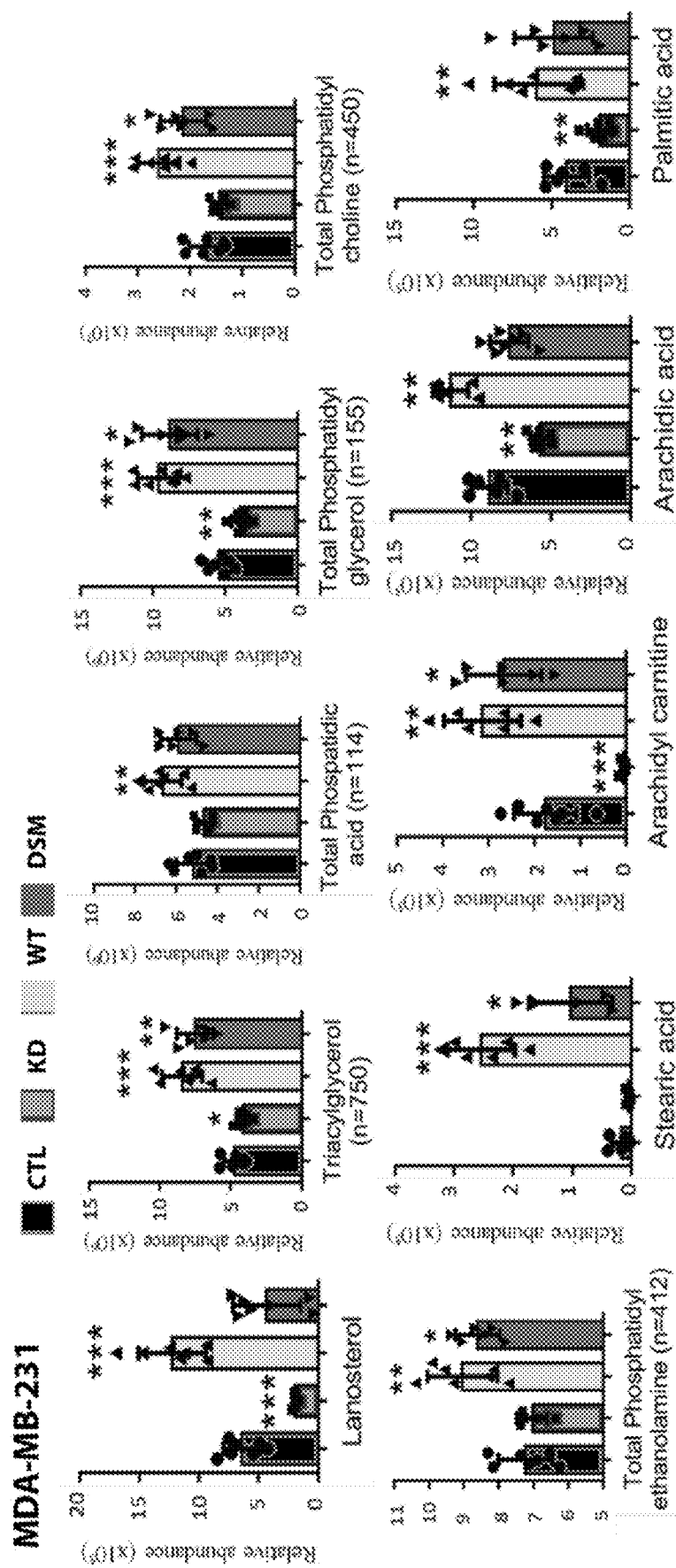
FIGS. 10A to 10D show de novo lipogenesis correlates with levels of DAXX expression.
Figure 10B:
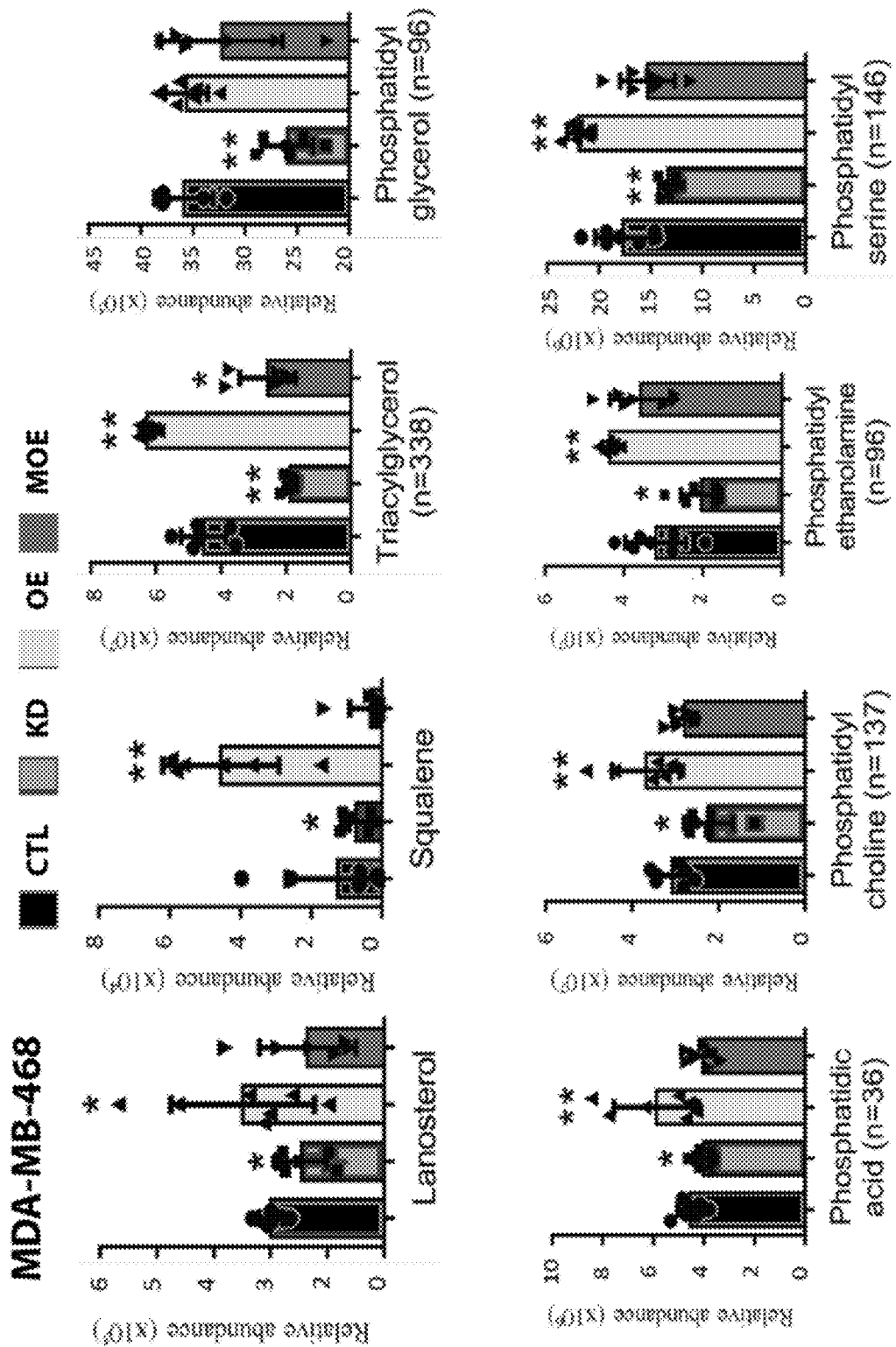
Figure 10C:
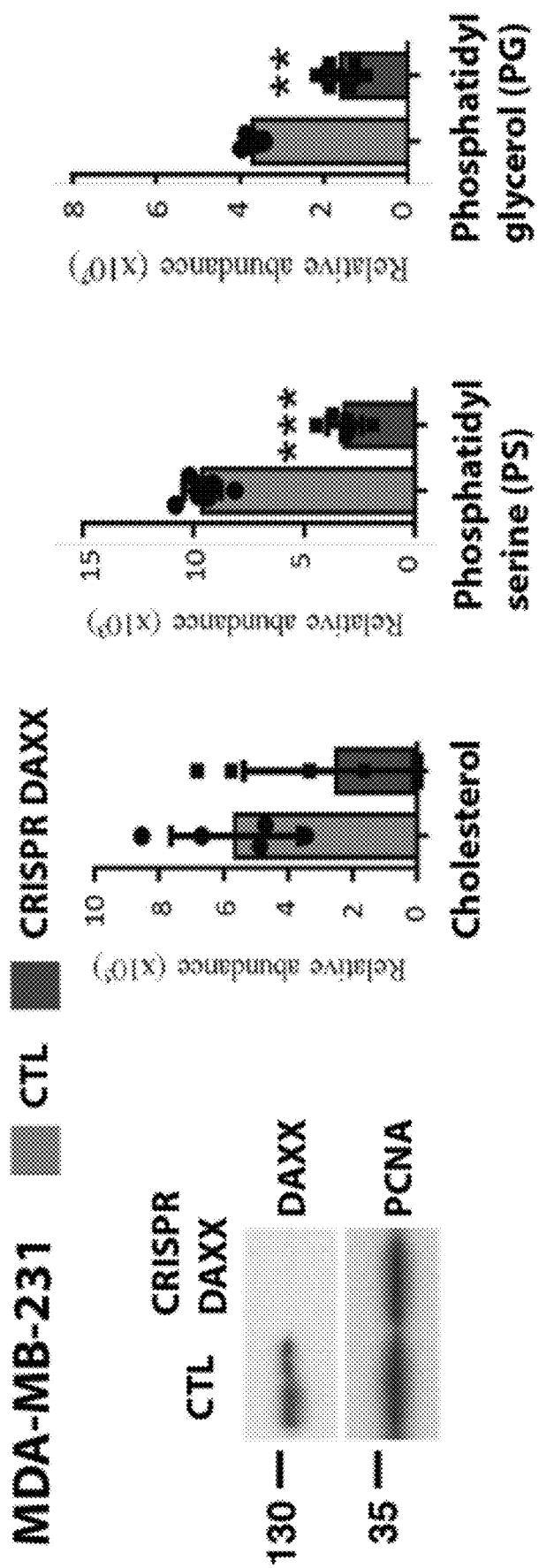
Figure 10D:
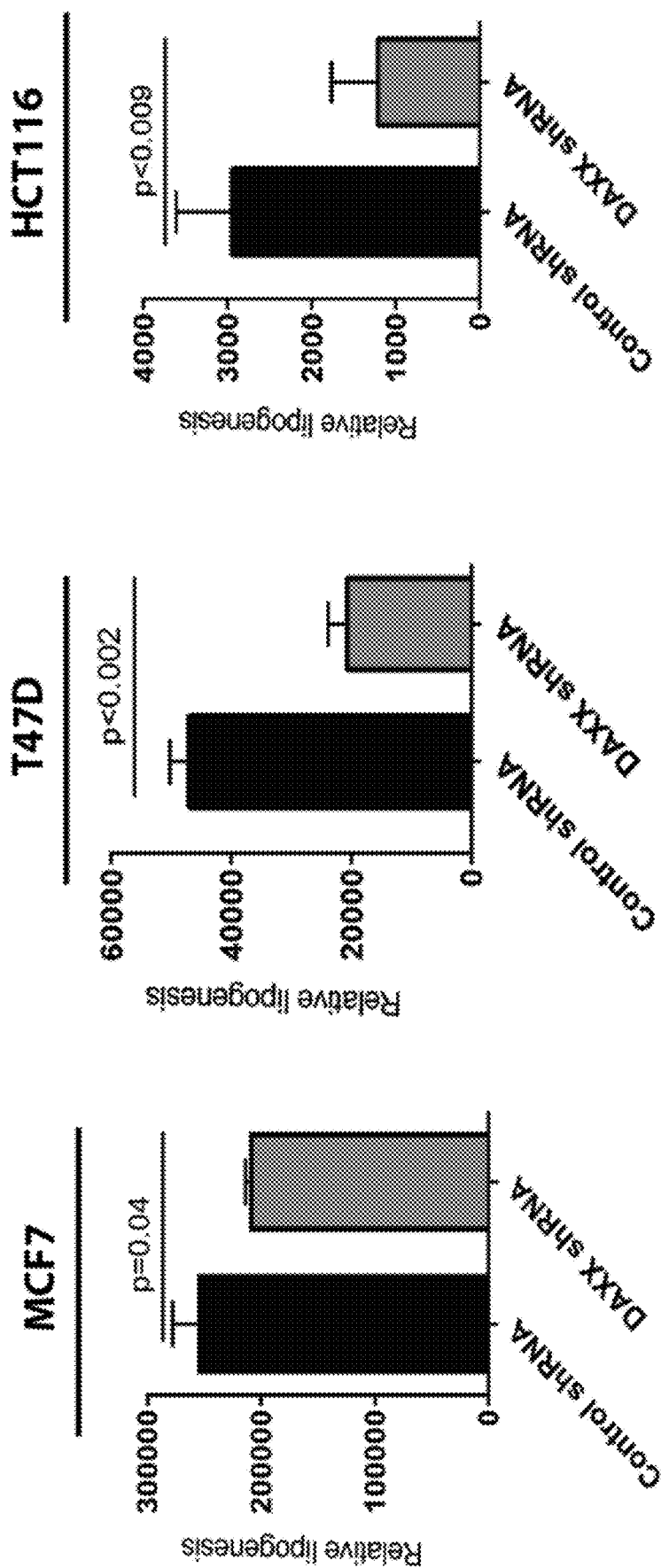
Figure 11A:
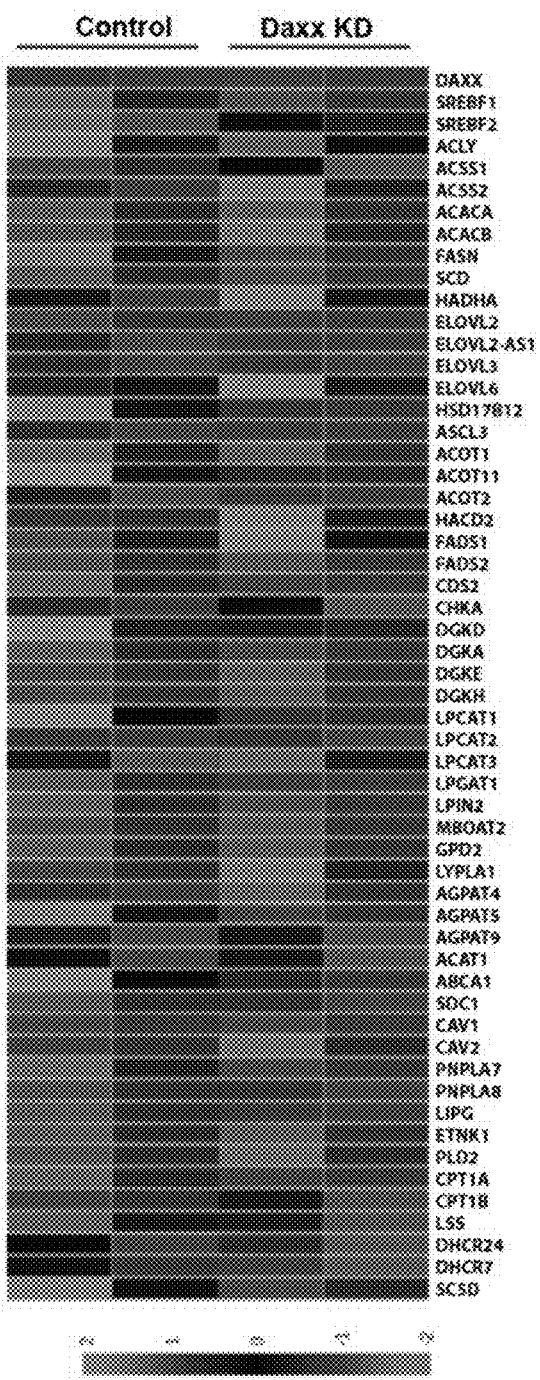
FIGS. 11A to 11D show DAXX, SREBP1 and SREBP2 are key regulators for lipogenic gene expression.
Figure 11B:
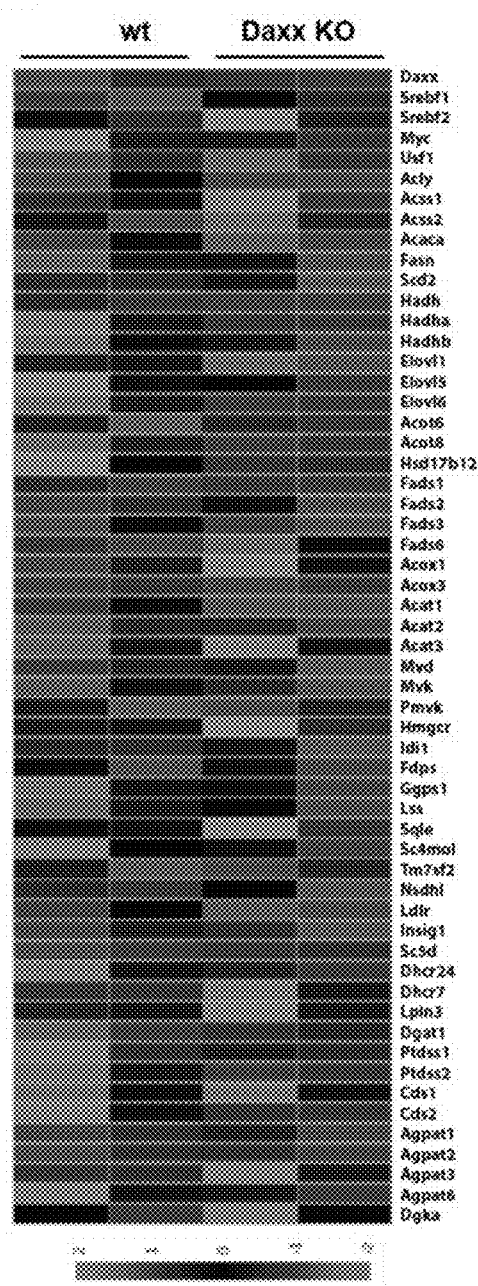
Figure 11C:
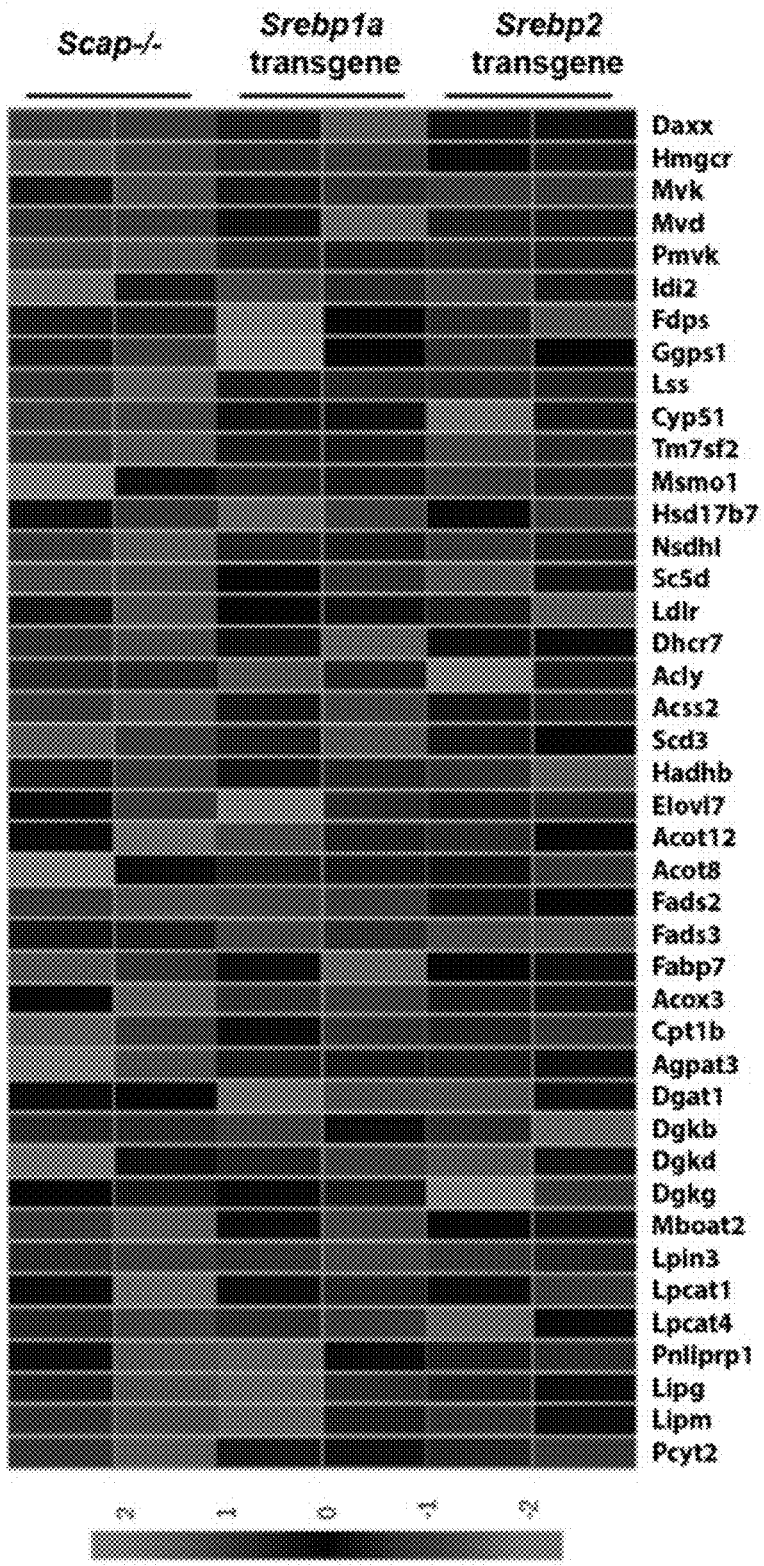
Figure 11D:
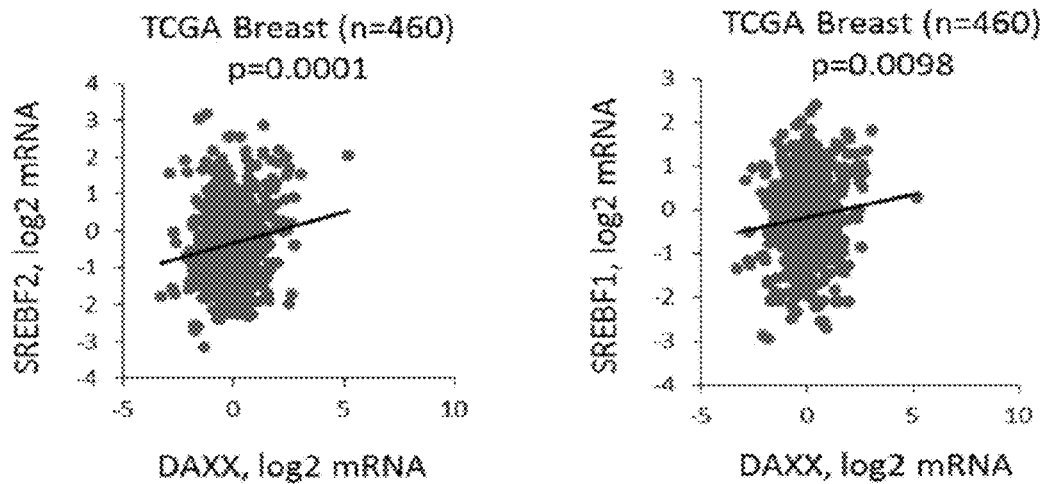

De novo lipogenesis assays using [$^{14}$C]-acetate metabolic labeling confirmed that DAXX expression levels correlated with levels of intracellular lipid synthesis, with reduced or increased de novo lipid synthesis in DAXX KD or wt OE cells, respectively (FIG. 1G). However, the DSM mutant (DSM OE) failed to enhance de novo lipogenesis (FIG. 1G). Consistently, mass spectrometry (MS)-based lipidomic profiling revealed that DAXX KD reduced but wt OE increased levels of specific lipid molecules, respectively, and again, the DSM mutant could not increase the levels of these lipid molecules (FIGS. 1H and 1I; FIGS. 10A and 10B). DAXX knockdown through CRISPR/Cas9 also impaired lipid production in MDA-MB-231 cells, providing an independent validation (FIG. 10C). Diminished de novo lipogenesis upon DAXX depletion was also observed in BC cell lines of luminal subtypes (MCF7 and T47D) and the colon cancer cell line HCT116 (FIG. 10D). Furthermore, reduced expression of lipogenic genes was also observed in the prostate cancer cell line PC3 with DAXX knockdown (Puto L A, et al. J Biol Chem 2015 290(25):15406-20), and mouse embryonic stem cells with Daxx knockout (Hoelper D, et al. Nat Commun 2017 8(1):1193) (FIG. 11A-1C). These data together indicate that DAXX is a general activator of lipogenesis.

DAXX Interacts with SREBP1 and SREBP2

Figure 2A:
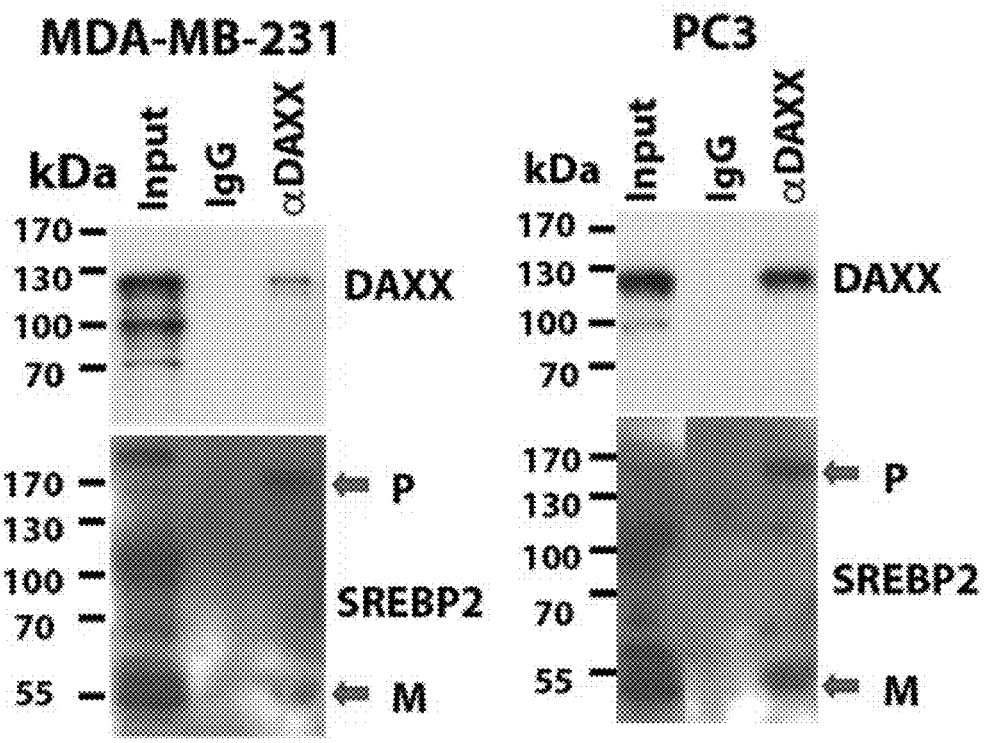
FIGS. 2A to 2E show DAXX binds to SREBP2.

SREBP1l2 promote lipid production when the intracellular levels of lipid/sterols are low (Griffiths B, et al. Cancer Metab 2013 1(1):3). Because DAXX depletion markedly downregulated the SREBP/lipid biosynthesis pathway (FIG. 1), it was reasoned that DAXX could regulate lipid biosynthesis through interacting with SREBPs. Immunoprecipitation (IP) of total cell extracts with anti-DAXX antibody evidenced co-precipitation of two SREBP2 proteins (FIG. 2A) that correspond to the precursor (P) and the mature (M) forms of SREBP2. Note that the apparent molecular weight of the co-precipitated putative precursor appears larger than the predicted full-length SREBP2 (~125 kDa) in multiple cell lines under various experimental conditions, likely due to differential posttranslational modifications (FIGS. 12 and 13).

In MDA-MB-231 cells, DAXX interacted with both precursor and mature forms of SREBP1 (FIG. 13A). Notably, whereas the mature SREBP1 was predominantly detected in the nucleus, the precursor was seen in both nuclear and cytoplasmic fractions (FIG. 13A; similar patterns were seen for SREBP2, FIG. 12B). However, the mature SREBP1 was clearly enriched in the DAXX immunoprecipitates of both fractions, indicating that DAXX has a high affinity to the mature SREBP1 (FIG. 13A). Consistently, the interactions between DAXX and the precursor (full-length or FL) as well as the mature form of SREBP1/2 (both endogenous and ectopically expressed) were observed in 293T cells (FIG. 13B). Notably, the endogenous SREBP1 (precursor and mature) were highly enriched in the DAXX immunoprecipitates, as they were undetectable in the total 293T cell lysates (Input, in which the transfected SREBP1 constructs were clearly visible), but readily detected in the IP samples (FIG. 13B). Collectively, these data establish that DAXX binds to both precursor and mature SREBP1/2.

Figure 2B:
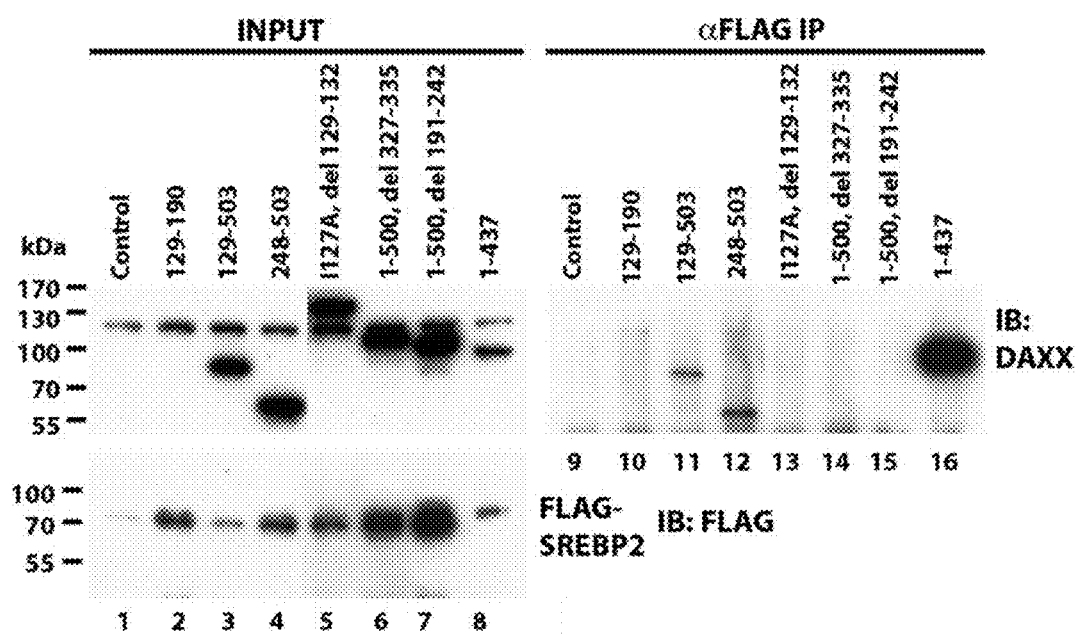
Figure 2C:
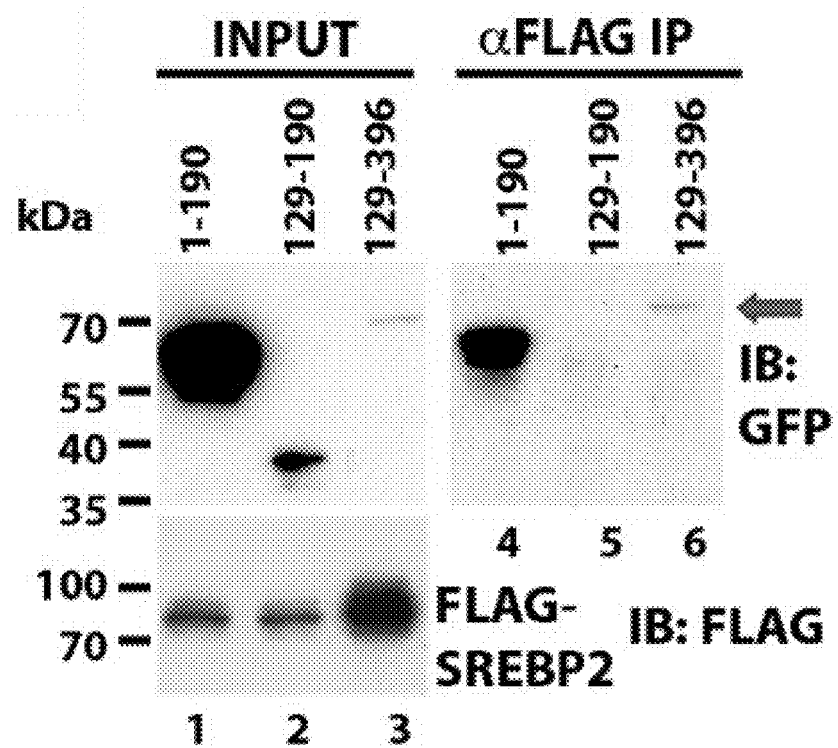
Figure 2D:
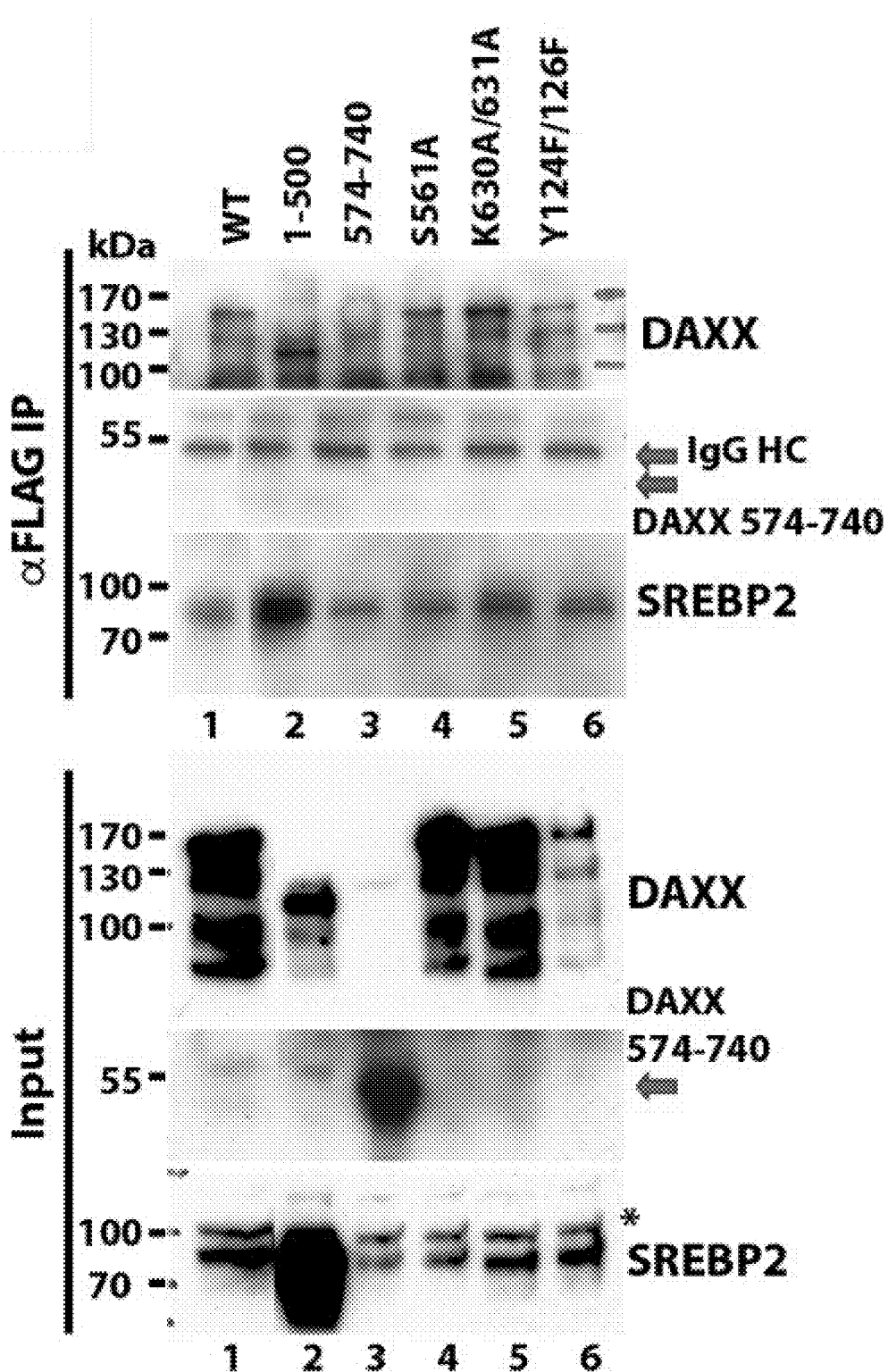
Figure 2E:
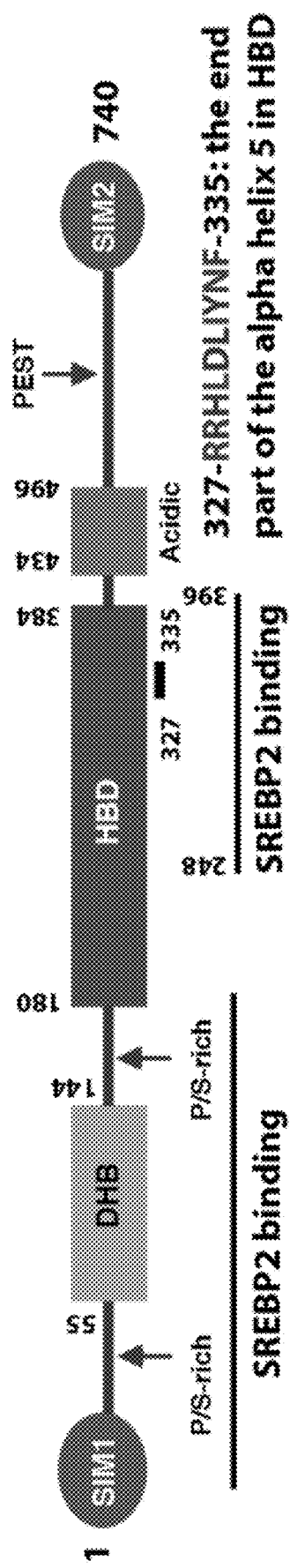

Using various DAXX deletion constructs in transfected 293T cells, it was found that the mature SREBP2 interacted with two separate regions of DAXX, the N-terminal part encompassing the well-folded helical bundle domain termed DHB (DAXX helical bundle) (Escobar-Cabrera E, et al. Structure 2010 18(12):1642-53) and a part of the central histone-binding domain (HBD) (Elsasser S J, et al. Nature 2012 491(7425):560-5) (FIG. 2). Interestingly, although DHB and HBD individually bound robustly to SREBP2 (FIG. 2B lanes 11 and 12; FIG. 2C lanes 1 and 3), the integrity of both binding sites appeared critical when both were present in a DAXX construct. Indeed, mutations within DHB or HBD (FIG. 2B lanes 13-15) attenuated the DAXX-SREBP2 interaction. Interestingly, the DAXX construct (aa 1-437) lacking the sequence from the acidic domain to the C-terminus seemed to show higher affinity to SERBP2 (FIG. 2B lane 16). The C-terminal region of DAXX spanning aa 574-740 did not bind to SREBP2 (FIG. 2D lane 3; note that the co-IP of endogenous DAXX with FLAG-SREBP2 was detectable). The deletion of the amino acid (aa) sequence between the DHB and HBD (aa 128-187), the N-terminal part of HBD (aa 191-241), the acidic domain (aa 434-496), and the Pro/Glu/Ser/Thr-rich (PEST) sequence immediately after the acidic domain (aa 503-572) did not affect the SREBP2-DAXX binding (FIG. 13C). Point mutations in the DHB (Y124F/Y126F) and C-terminal region (S561 and K630A/631A) also did not influence the DAXX-SREBP2 interaction (FIG. 2D). The mature SREBP1a bound to DAXX in a similar fashion (FIGS. 13D and 13E). Thus, SREBP1/2 interact with two independent sites in DAXX (FIG. 2E).

SREBP-Binding Sites are Enriched in DAXX-Associated Chromatins

Figure 3A:
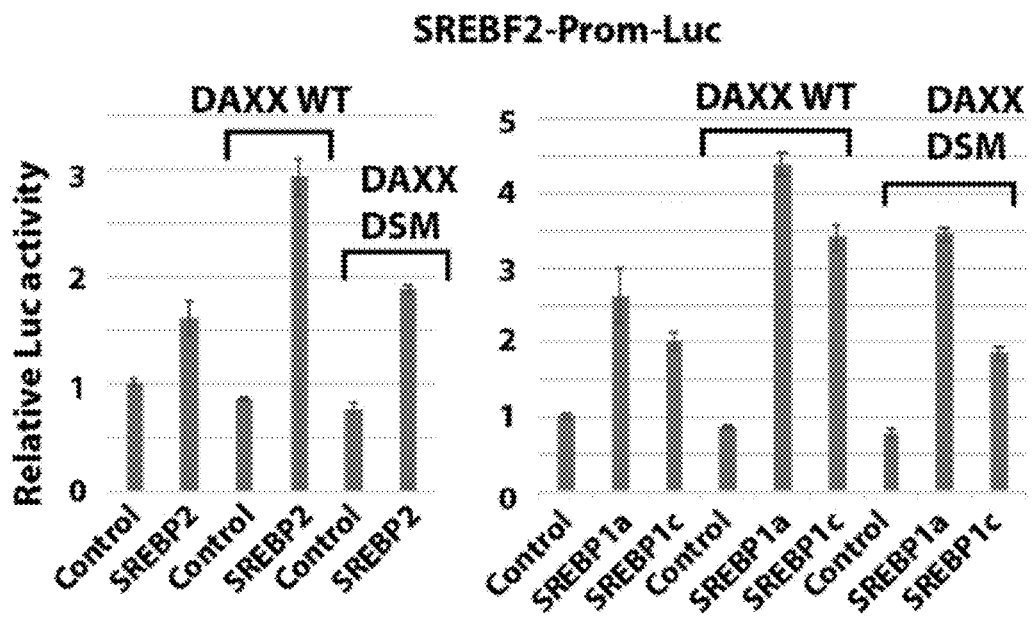

DAXX knockdown reduced the expression of lipogenic genes (FIG. 1) and DAXX physically interacted with SREBP112 (FIG. 2 and FIG. 13). It was reasoned that DAXX promotes SREBP-mediated transcription on chromatins. To test this, luciferase reporter assays were first conducted. As shown in FIG. 3A, enforced expression of SREBP2, SREBP1a and SREBP1c increased the activity of luciferase reporter that was under the control of the SREBF2 promoter containing sterol-responsive elements (SREs). Co-expression of DAXX further increased the luciferase activity, while DAXX alone had only minimal effects. In contrast, the DAXX DSM mutant was largely unable to coactivate SREBP1/2-mediated transcription (FIG. 3A).

Figure 3B:
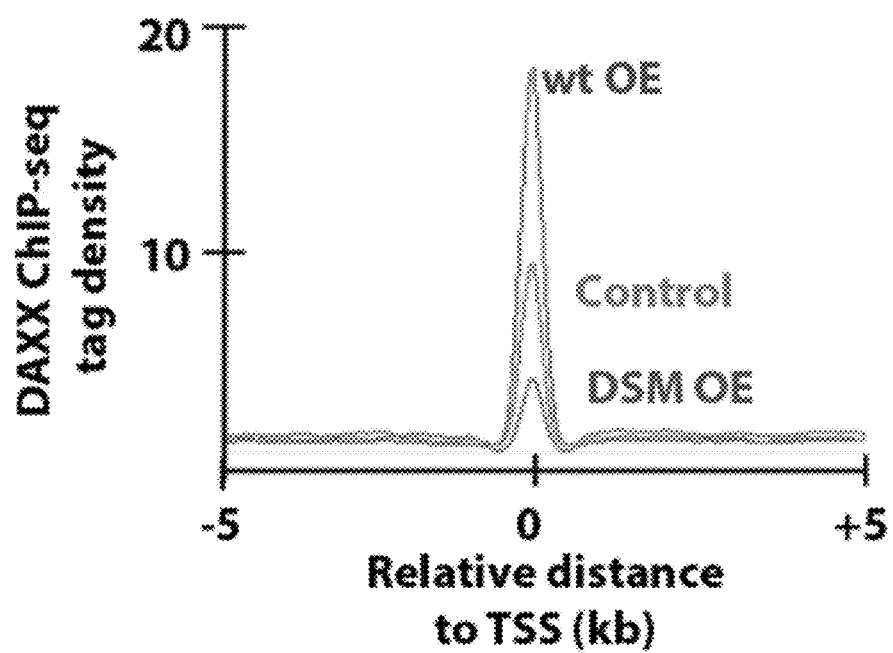
Figure 3E:
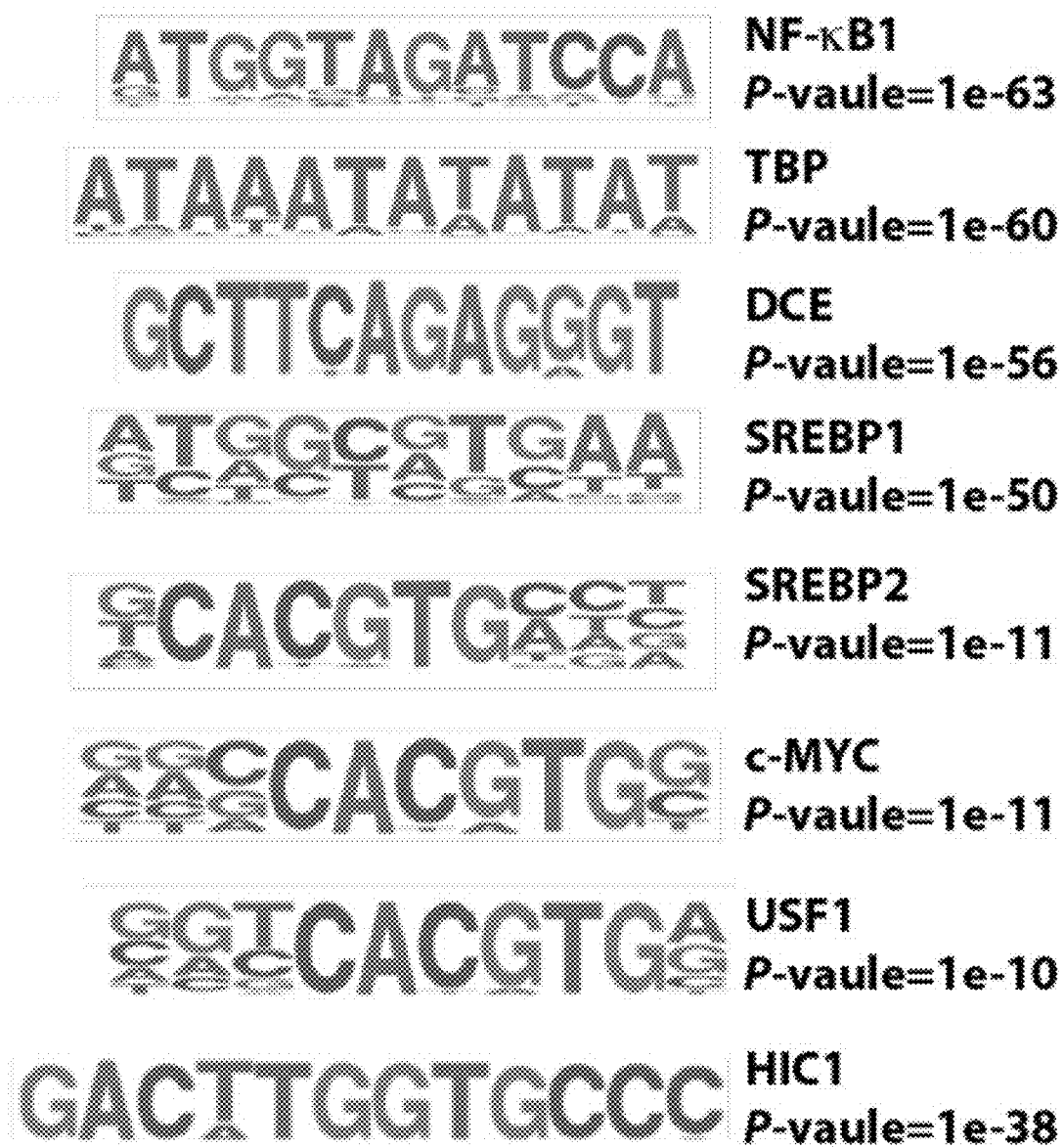

Genome-wide occupancy of DAXX was surveyed using the ChIP-seq technology. Overexpression of wt DAXX but not the DSM mutant increased DAXX's chromatin association (FIGS. 3B and 3C). Consistent with other studies (Puto L A, et al. Oncoscience 2015 2(4):362-72), DAXX primarily bound to sites in introns and intergenic regions with less frequent association with promoters (FIG. 3D). A de novo motif analysis revealed that SREBP-binding elements were significantly enriched in DAXX-associated sites (FIG. 3E).

Figure 3F:
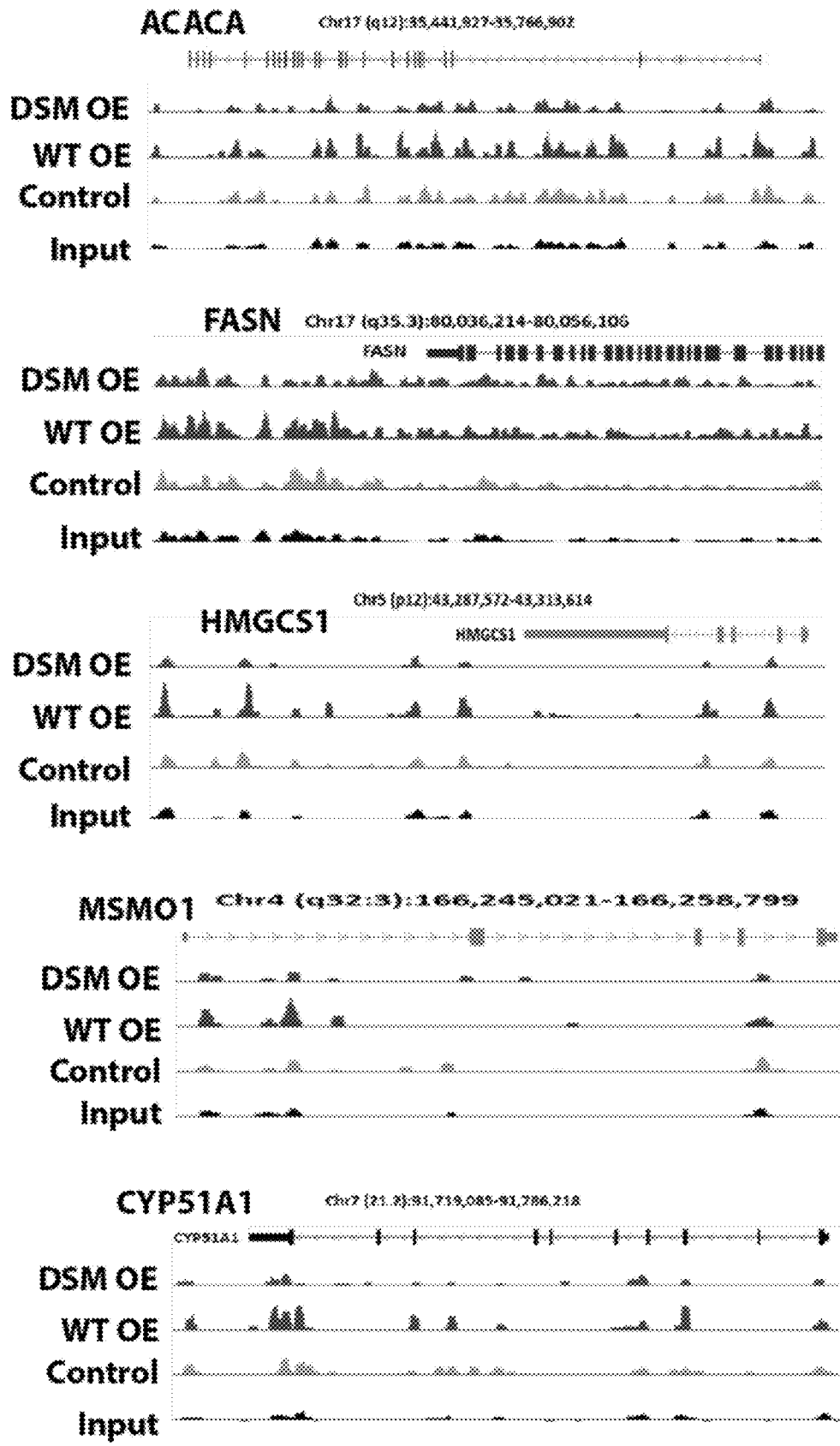

Notably, the DAXX DSM mutant exhibits reduced overall chromatin association (FIGS. 3B and C) as well as diminished occupancy at individual lipogenic genes compared to wt DAXX (FIG. 3F and FIG. 14). De novo motif analysis indicates that the SREBP1 motif was less significantly enriched, while the enrichment of the SREBP2 motif was insignificant (FIG. 14A) in DAXX-precipitated chromatins from MDA-MB-231 DSM OE cells. The reduced chromatin-recruitment of the DSM mutant was not due to its reduced affinity to the antibody used for ChIP, as this antibody was found to bind the DSM mutant as efficiently as the wt DAXX. These ChIP-seq data along with the luciferase reporter assays show that the SUMO-binding activity of DAXX may be critical for efficient recruitment of DAXX to chromatins, which provides a probable molecular explanation for the inability of the DSM mutant to activate lipogenic gene expression and de novo lipogenesis (FIG. 1 and FIG. 10).

Notably, the binding motifs of other known DAXX-binding transcription factors such as NF-κB (Puto L A, et al. Genes Dev 2008 22(8):998-1010) were highly enriched in DAXX ChIP-seq peaks (FIG. 3E). These data also implicate the chromatin recruitment of DAXX by other transcription factors such as RUNX1, RUNX2 and USF1 that were not previously shown to interact with DAXX (FIGS. 3E and 14). Furthermore, DAXX might interact with the core-transcriptional machinery, as the TATA-box and DCE (downstream core element) were enriched in DAXX-binding chromatins (FIG. 3E and FIG. 14).

DAXX is Critical for Tumor Growth In Vivo

To assess roles of DAXX in cell proliferation and tumor growth, the effects of DAXX expression levels on the proliferation of MDA-MB-231 cells was first tested. DAXX expression levels did not exert significant effects on cell proliferation under conventional two-dimensional cell culture condition, although DAXX knockdown moderately slowed the proliferation of MDA-MB-231 cells (FIG. 15A). The SREBP/lipogenesis pathway has been linked to the control of cell size/volume (Ricoult S J, et al. Oncogene 2016 35(10):1250-60; Porstmann T, et al. Cell Metab 2008 8(3):224-36). Indeed, the cell morphology and size were markedly different for cells with variable levels of DAXX expression (FIG. 15B). Cells with reduced DAXX levels appeared smaller with spindle-like morphology, while cells with wt DAXX OE were larger when compared to control cells (FIG. 15B and FIG. 9A). In contrast, the DAXX DSM mutant OE did not appear to affect cell size or morphology (FIG. 15B). The impact of DAXX expression levels on cell proliferation was then assessed in three-dimensional cell culture models. DAXX knockdown reduced the number and size of colonies when compared to control, while wt DAXX OE had the opposite effects. Again, the DSM mutant had no effect on either colony size or number (FIG. 15C). Similar phenotypes were observed for a panel of HCT116 cells with different levels of DAXX expression (FIG. 15D-H).

Figure 4A:
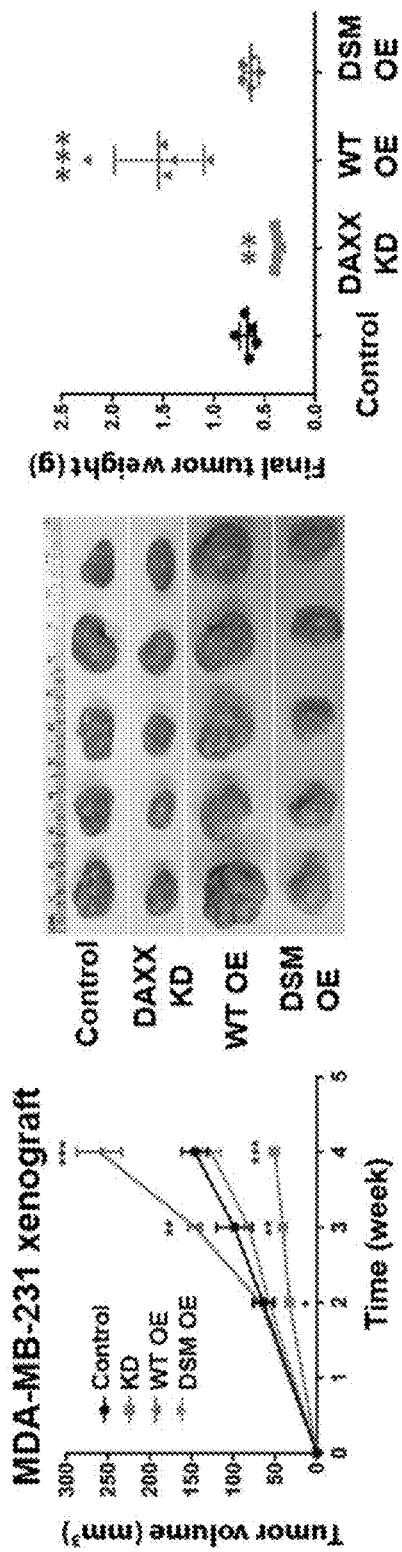
FIGS. 4A to 4D show WT DAXX but not the SUMO-binding defective mutant (DSM) promotes tumor growth in vivo.
Figure 4B:
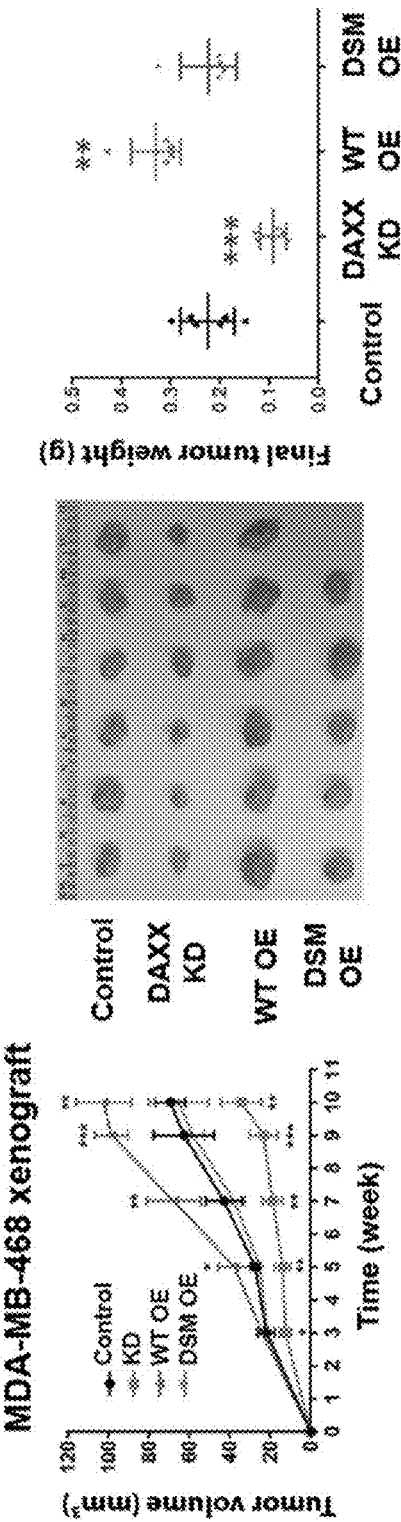
Figure 4C:
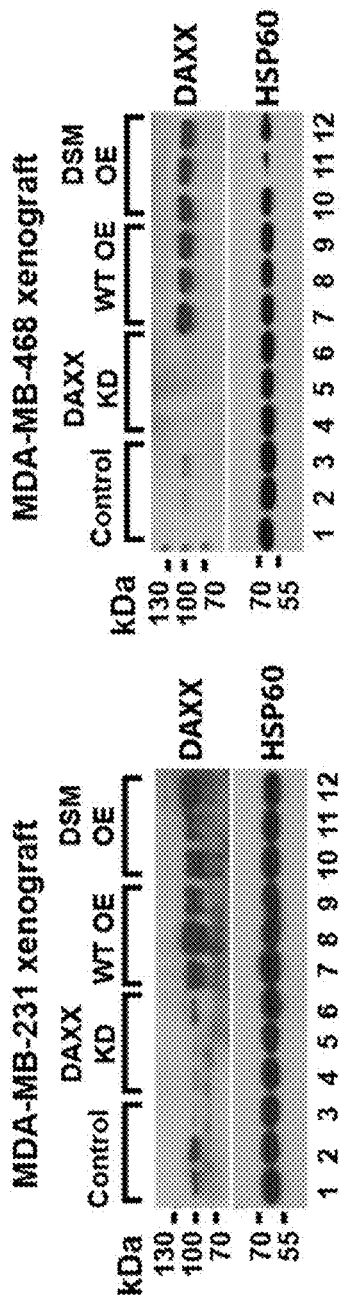
Figure 4D:
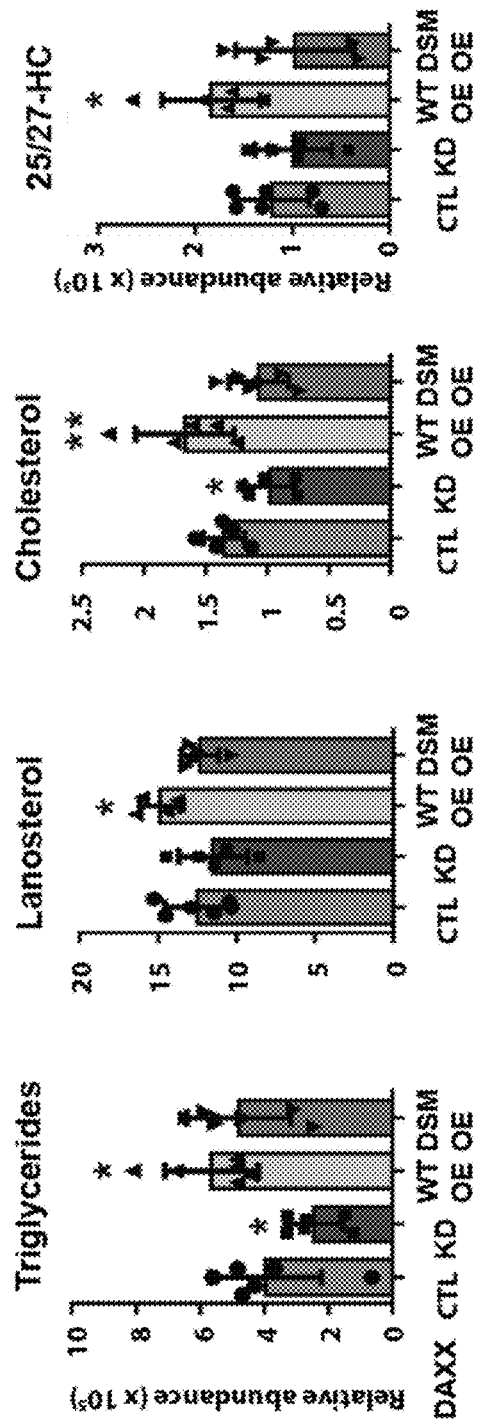

Effects of DAXX expression levels on tumor growth was examined in vivo. In orthotopic BC xenograft models using female mice, DAXX knockdown reduced while wt DAXX OE significantly increased xenograft tumor growth rate of both MDA-MB-231 and MDA-MB-468, two triple-negative BC (TNBC) cell lines (FIGS. 4A and 4B). Notably, the MDA-MB-231 xenograft tumors grew much more aggressively than MDA-MB-468 tumors (FIGS. 4A and 4B), but the effects of DAXX expression levels on tumor growth were observed regardless of tumor growth kinetics. The DSM mutant OE did not significant affect tumor growth in both MDA-MB-231 and MDA-MB-468 xenograft models. Immunoblotting analysis of tumor extracts shows that the levels for both the wt DAXX and DSM mutant were similar (FIG. 4C), indicating that the inability of the DSM mutant to promote tumor growth was not due to instability of the mutant protein. Lipidome in xenograft tumors derived from cells with different levels of DAXX expression was profiled, demonstrating that DAXX expression levels positively correlated with levels of lipids (FIG. 4D).

In a prostate cancer xenograft model (male mice) and a colon cancer xenograft model (both female and male mice), similar tumor growth phenotypes were observed: DAXX depletion slowed while wt DAXX OE accelerated the tumor growth. Consistently, DSM mutant OE was either completely unable to promote tumor growth, or moderately hindered tumor growth in all xenograft models (FIG. 4 and FIG. 16). In mouse allografts, Daxx depletion also markedly impaired tumor growth in immunocompetent (C57BLJ6) and immunodeficient (NSG) hosts (FIGS. 16C and 16D). These results demonstrate that DAXX exerts a strong oncogenic property and that the SUMO-binding activity is critical for DAXX's oncogenic function.

The DAXX-SREBP2 Axis Underpins Lipogenesis and Tumor Growth

Figure 5A:
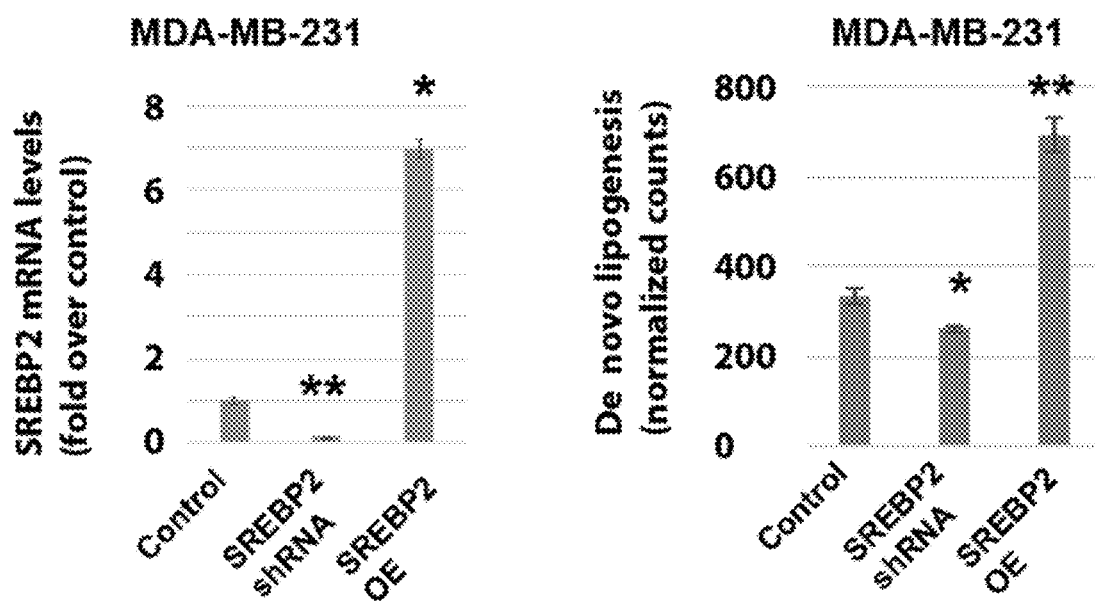
FIGS. 5A to 5C show DAXX enhances in vivo tumor growth via SREBP2.
Figure 5B:
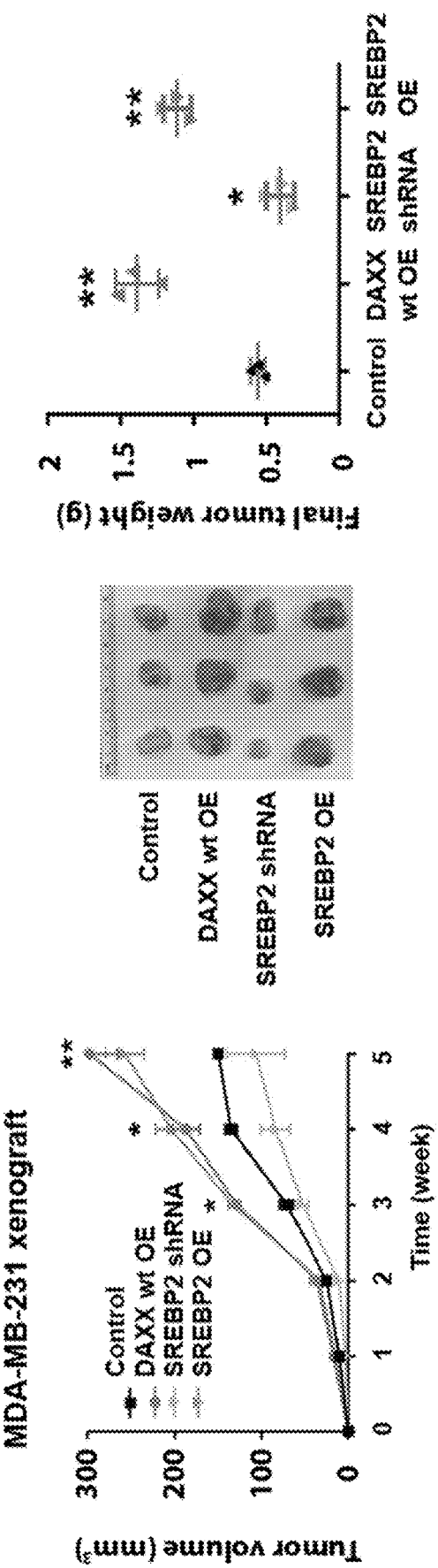
Figure 5C:
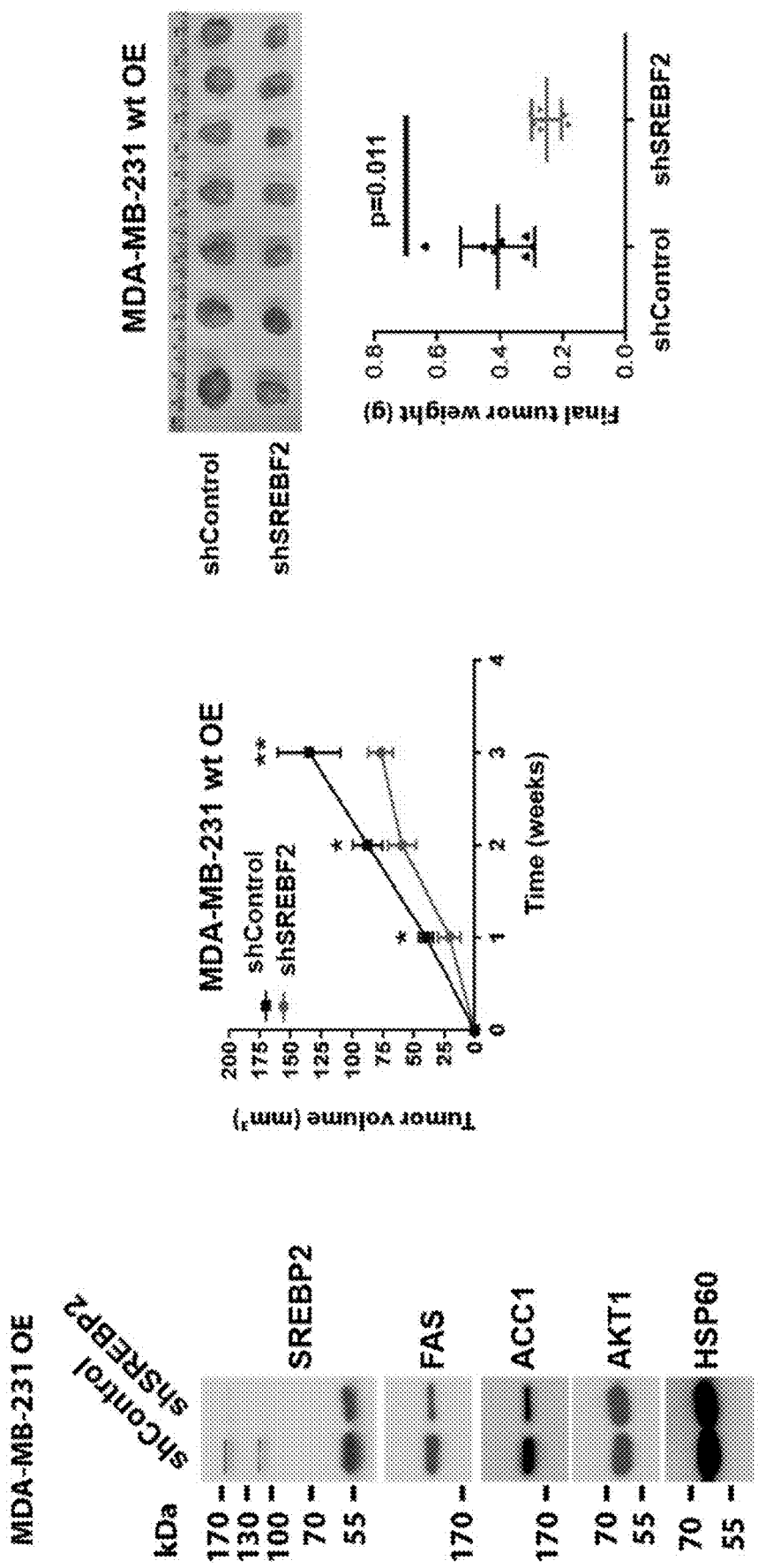

SREBP1/2 drive lipid biosynthesis to promote tumorigenesis (Griffiths B, et al. Cancer Metab 2013 1(1):3; Moon S-H, et al. Cell. 2019 176(3):564-580.e19). In MDA-MB-231 cells, SREBP2 knockdown reduced de novo lipogenesis from acetate and tumor growth in vivo. By contrast, SREBP2 overexpression increased lipogenesis and tumor growth (FIGS. 5A and 5B). Likewise, SREBP1 knockdown (or overexpression) impaired (or promoted) de novo lipogenesis and tumor growth respectively. To link SREBP2 to DAXX-mediated tumorigenesis, SREBP2 was depleted in MDA-MB-231 DAXX OE cells. SREBP2 knockdown in the DAXX OE cells significantly attenuated the levels of lipogenic enzymes and tumor growth (FIG. 5C), indicating that SREBP2 is a critical effector of DAXX's oncogenic function.

Figure 6A:
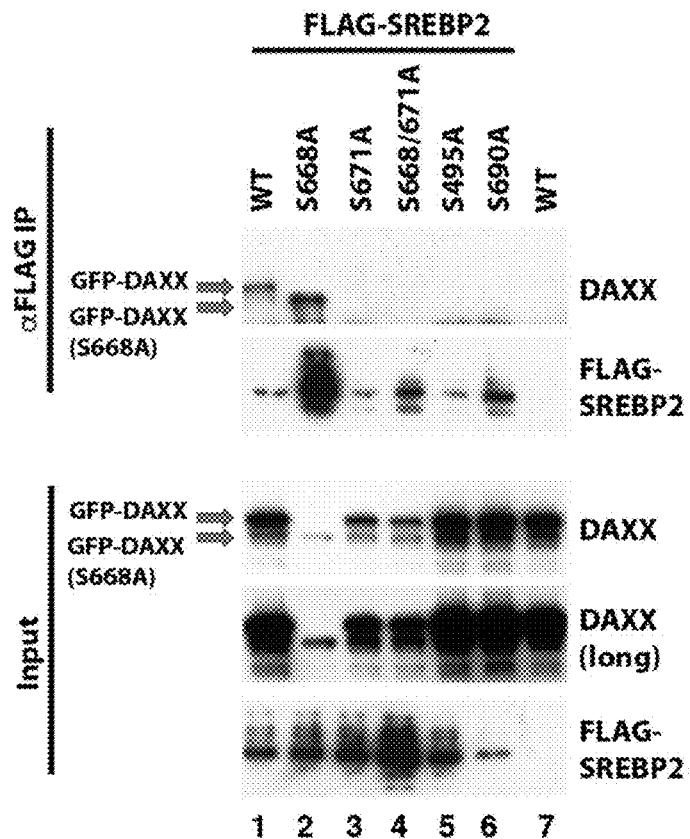
FIGS. 6A to 6H show mutation of DAXX phosphorylation sites disrupts DAXX-SREBP2 interaction, impairs lipogenesis and tumor growth.
Figure 6B:
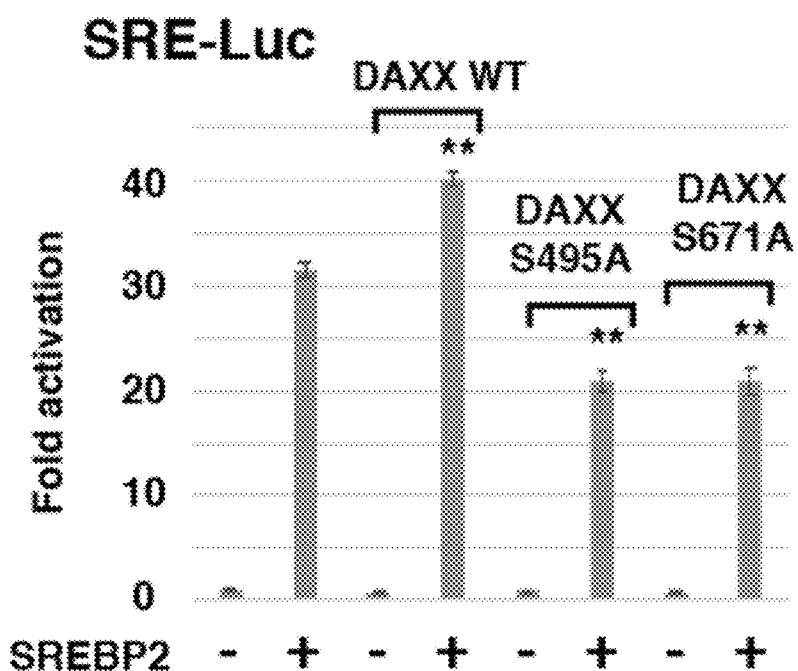
Figure 6C:
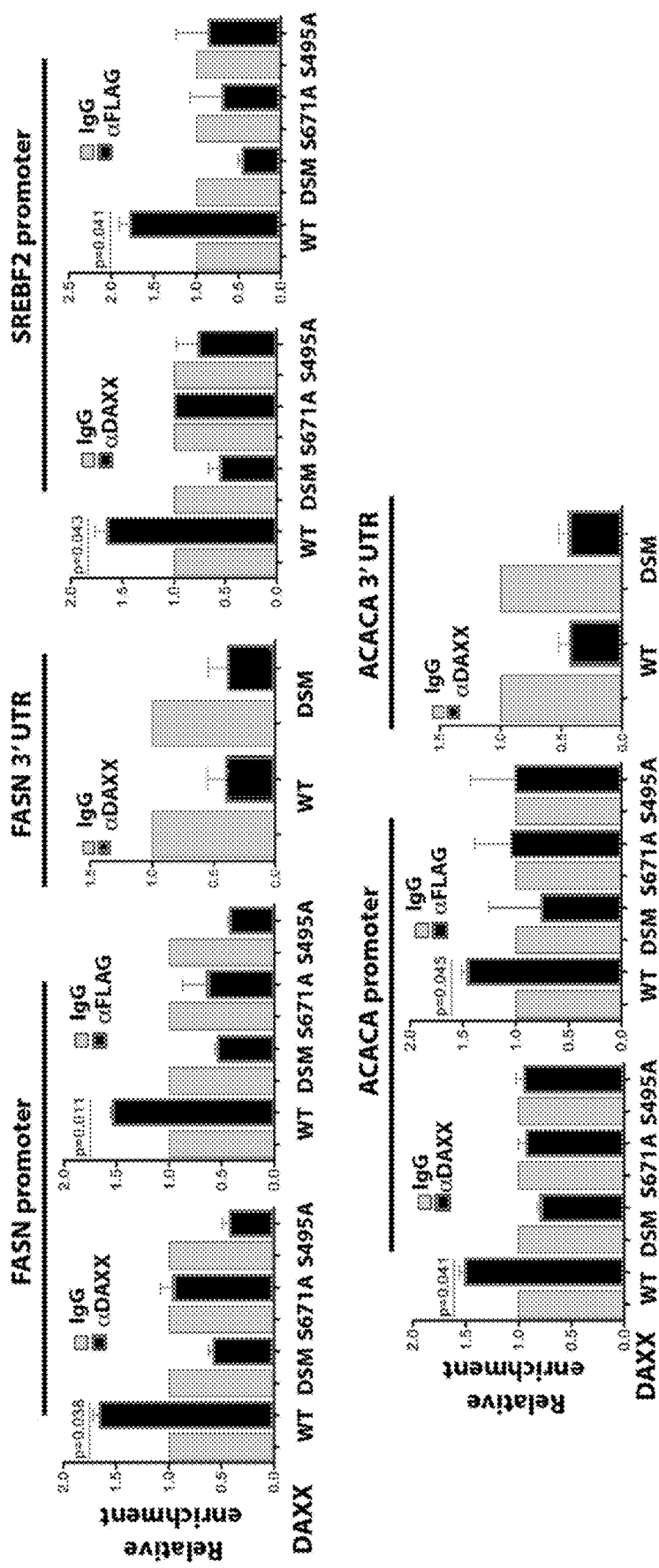
Figure 6D:
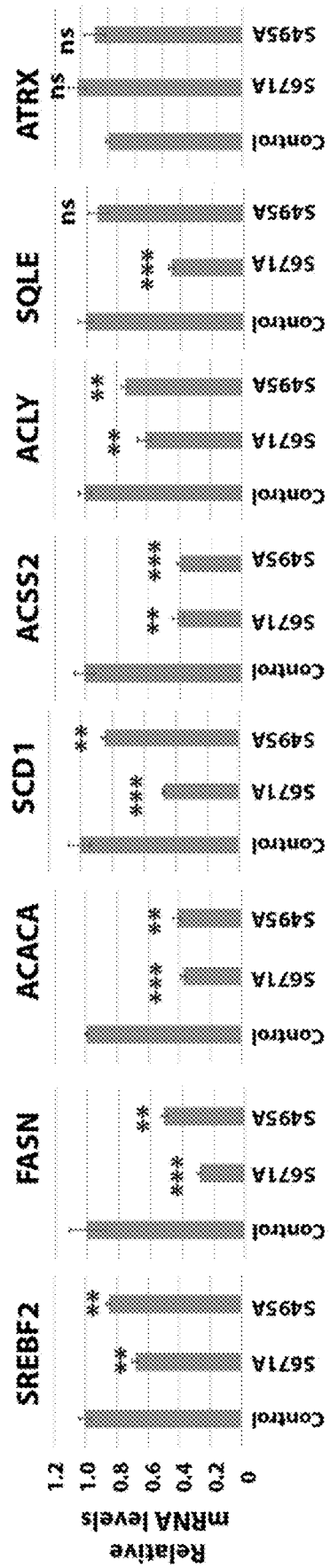
Figure 6E:
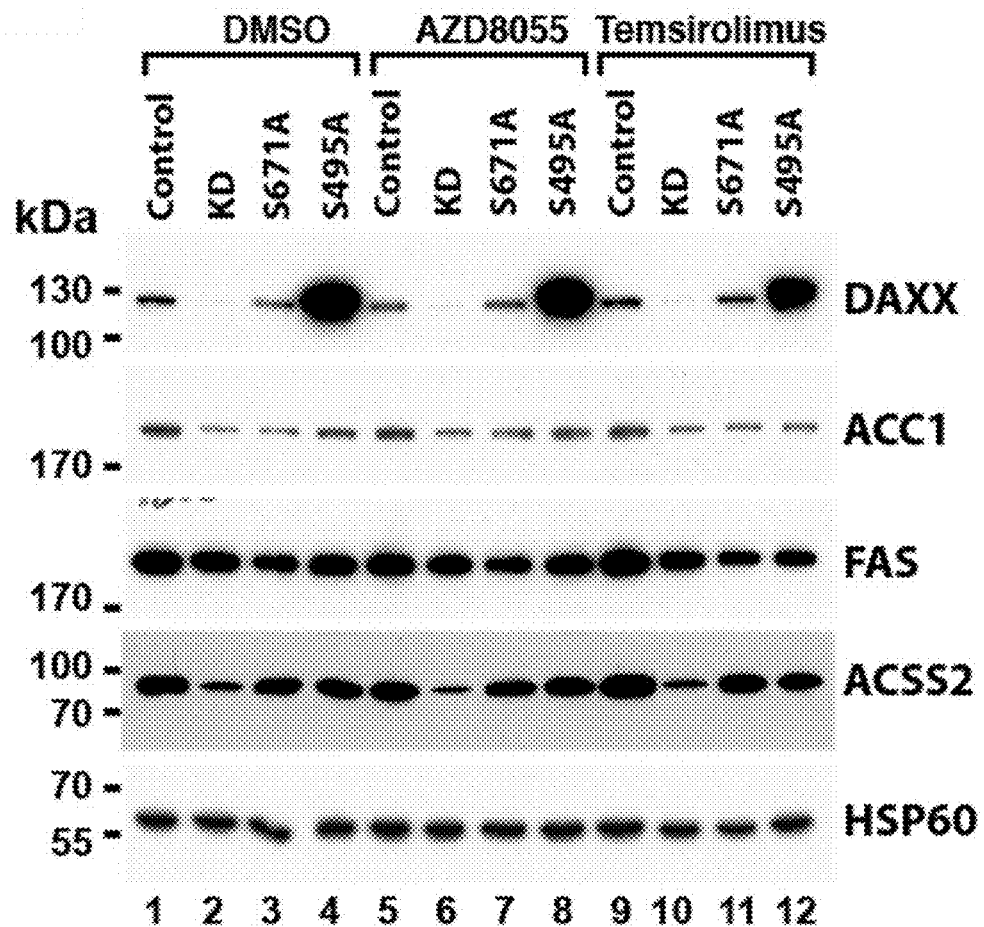

DAXX is a robustly phosphorylated protein on a number of frequently phosphorylated serine and threonine residues (Ecsedy J A, et al. Mol Cell Biol 2003 23(3):950-60) (FIG. 17). The interaction of DAXX isoforms containing mutations at frequently phosphorylated residues was tested with SREBP2. While wt DAXX and the S668A mutant coprecipitated with SREBP2, the S671A, S668A/S671A, S495A and S690A DAXX mutants failed to coprecipitate (FIG. 6A). Of note, the DAXX S668A mutant migrated faster than wt DAXX and other mutants in the SDS-PAGE gel in 293T and MDA-MB-231 cells (FIG. 6A and FIG. 17B). Both DAXX S671A and S495A mutants were capable of binding ATRX (FIG. 17C), which interacts directly with the DAXX DHB domain (Hoelper D, et al. Nat Commun 2017 8(1): 1193). In luciferase reporter assays, both DAXX S495A and S671A mutants failed to enhance SREBP2-mediated transcription (FIG. 6B). Experiments using ChIP followed by qPCR indicate that wt DAXX bound to the promoters of FASN, ACACA, and SREBF2, but the S495A, S671A and DSM mutants were not recruited to these promoters in MDA-MB-231 cells cultured in serum-free medium (FIG. 6C). Neither wt DAXX nor the DSM mutant were enriched in the 3' UTR region of FASN or ACACA gene (FIG. 6C), indicating that DAXX is recruited specifically to the promoter regions of lipogenic genes.

qRT-PCR assays show that lipogenic genes were downregulated in MDA-MB-231 cells expressing the DAXX S495A or S671A mutant (FIG. 6D). Immunoblotting analysis confirmed the reduced expression of ACC1 and FAS, and to a lesser extent ACSS2 (FIG. 6E). Because of the documented role for mTOR signaling in lipogenesis (Ricoult S J, et al. Oncogene 2016 35(10):1250-60), effects of the mTOR kinase inhibitors AZD8055 (inhibits both mTORC1 and mTORC2) and temsirolimus (inhibits mTORC1) were tested. Neither of these inhibitors had obvious effects on the protein levels of ACC1, FAS and ACSS2 in the control or S671A-expressing cells, although temsirolimus reduced levels of both ACC1 and FAS in cells expressing the S495A mutant (FIG. 6E lane 12). Together, these results suggest that DAXX is recruited to the promoters of lipogenic genes through interacting with SREBP2, thereby enhancing lipogenic gene expression.

Unexpectedly, the DAXX S671A mutant protein failed to accumulate in transduced MDA-MB-231 cells, although the S495A mutant protein expressed at a high level (FIG. 6E). Although why the S671A mutant is less stable remains to be determined, its inability to bind to H3.3 might provide an explanation (FIG. 17C), as the interaction of DAXX with the H3.3/H4 dimer appears to stabilize DAXX (Hoelper D, et al. Nat Commun 2017 8(1):1193). Regardless, these data indicate that the loss-of-function phenotypes of the DAXX S671A and S495A mutations were unrelated to the steady-state protein levels detected in immunoblotting.

Figure 6F:
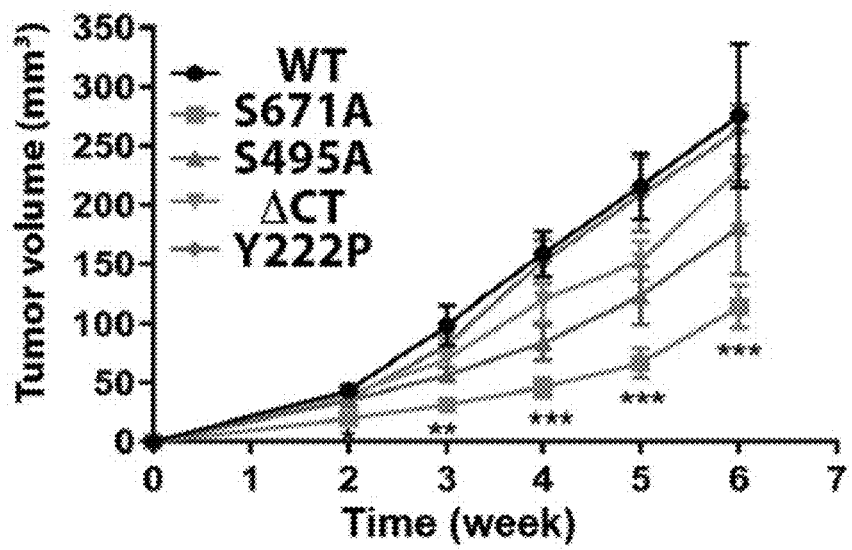
Figure 6F:
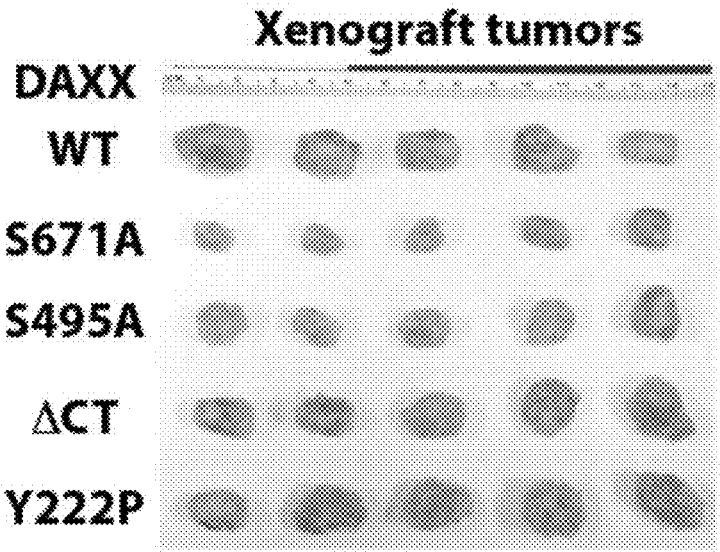
Figure 6F:
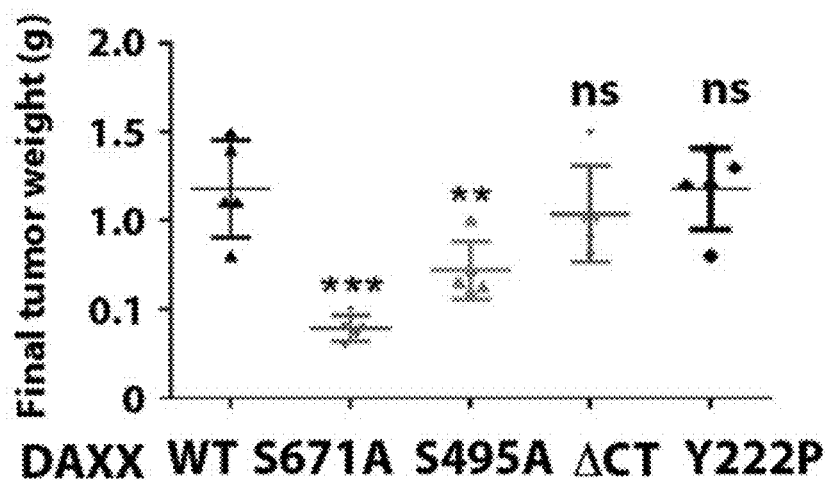
Figure 7A:
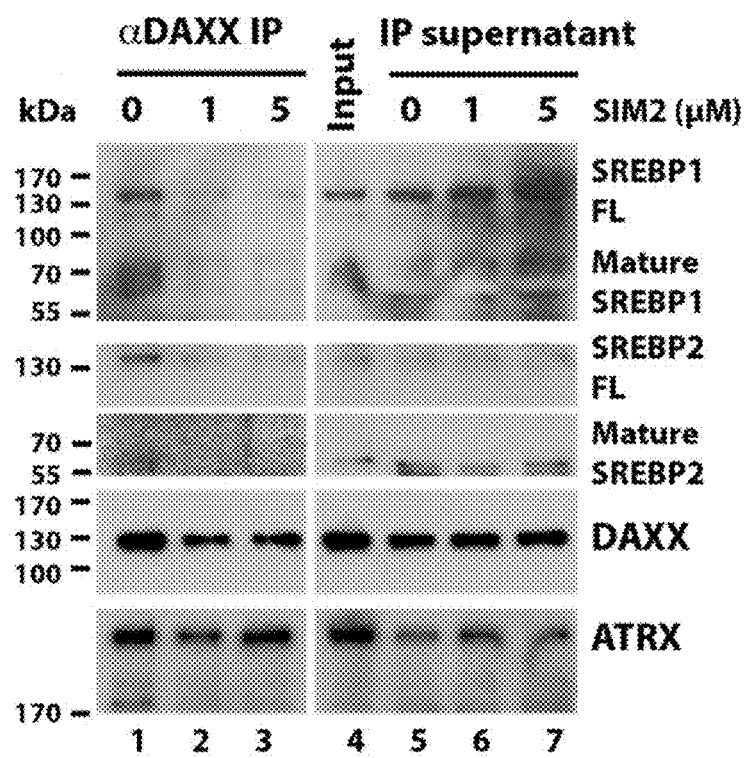
FIGS. 7A to 7E show the DAXX SIM2 peptide disrupts DAXX-SREBP interaction and suppresses tumor growth in vivo.
Figure 7B:
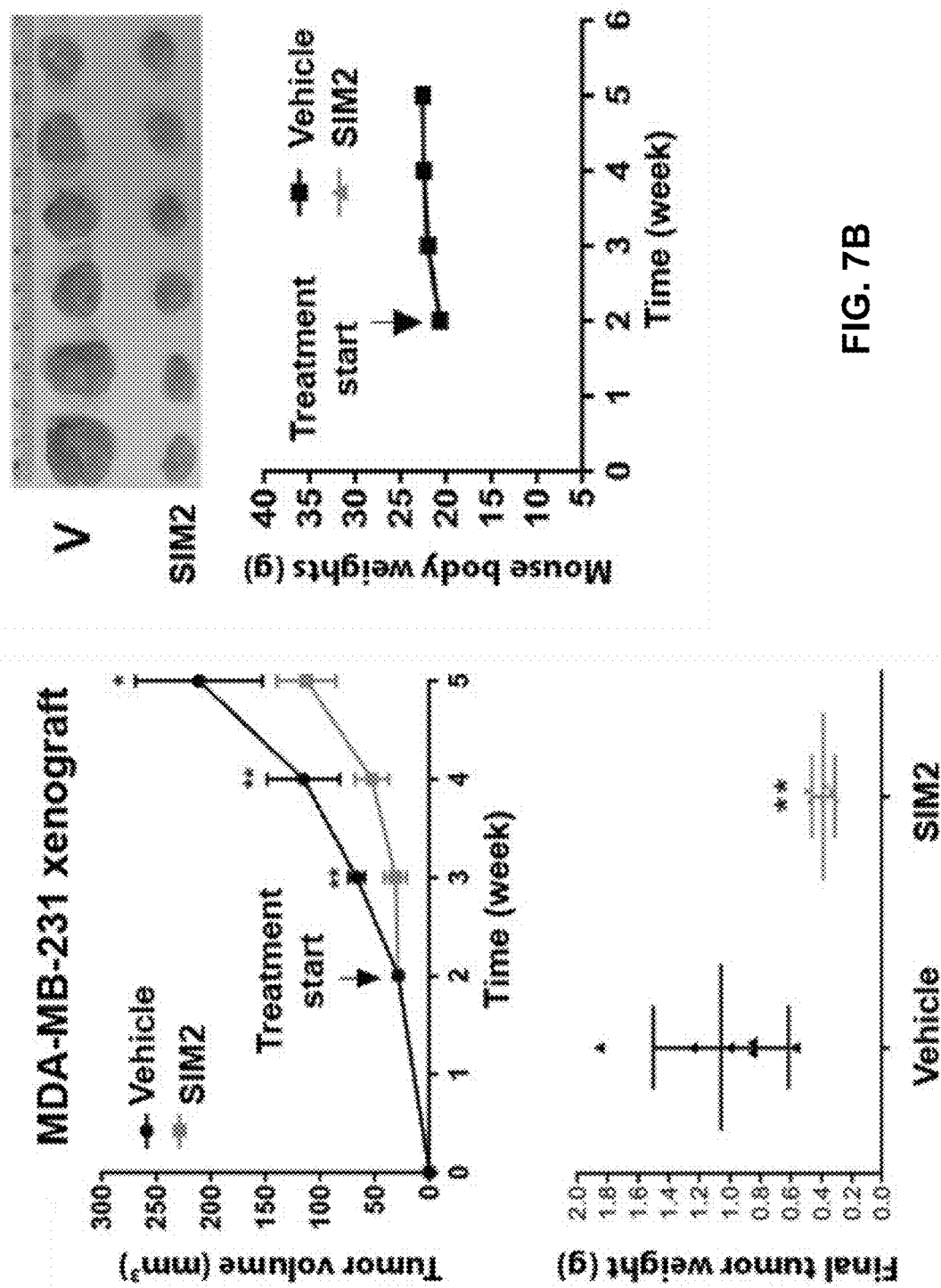
Figure 7C:
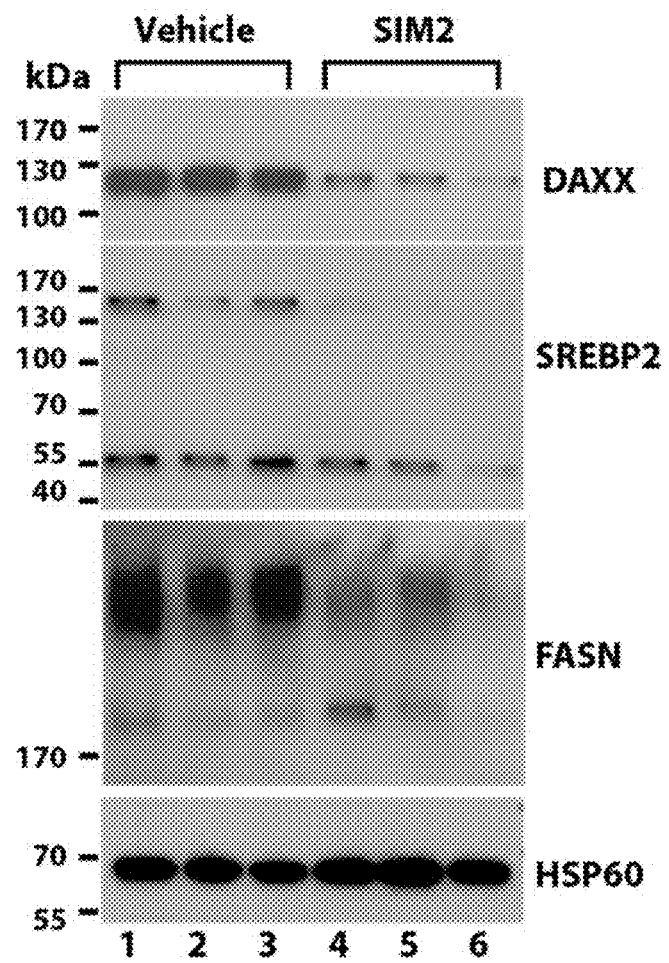

Remarkably, the S671A mutant was profoundly defective to stimulate tumor growth in vivo (FIG. 6F). The S495A mutant was also impaired to promote tumor growth compared to wt DAXX (FIG. 6F). Interestingly, the ΔCT mutant (lacking aa 737-740) and the Y222P mutant were as potent as the wt DAXX to enhance tumor growth (FIG. 6F). The Y222P mutant is expected to interrupt the interactions of DAXX with H3.3 (Elsasser S J, et al. Nature 2012 491 (7425):560-5) (FIG. 17D). Indeed, the Y222P mutant did not bind H3.3 (FIG. 7C). Together, these data suggest that DAXX's oncogenic property is distinct from its histone chaperone function and its interaction with ATRX.

Figure 6G:
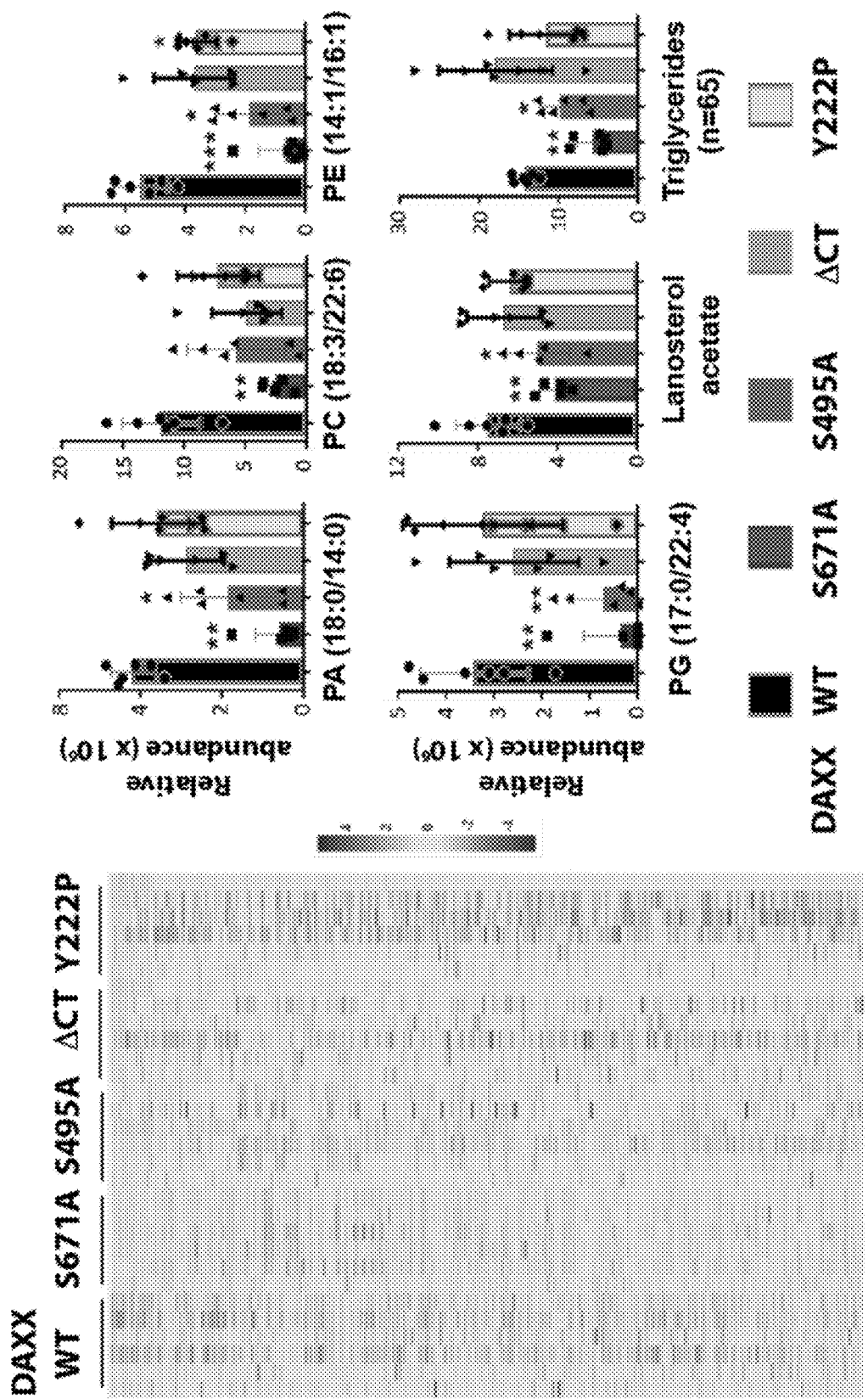
Figure 6H:
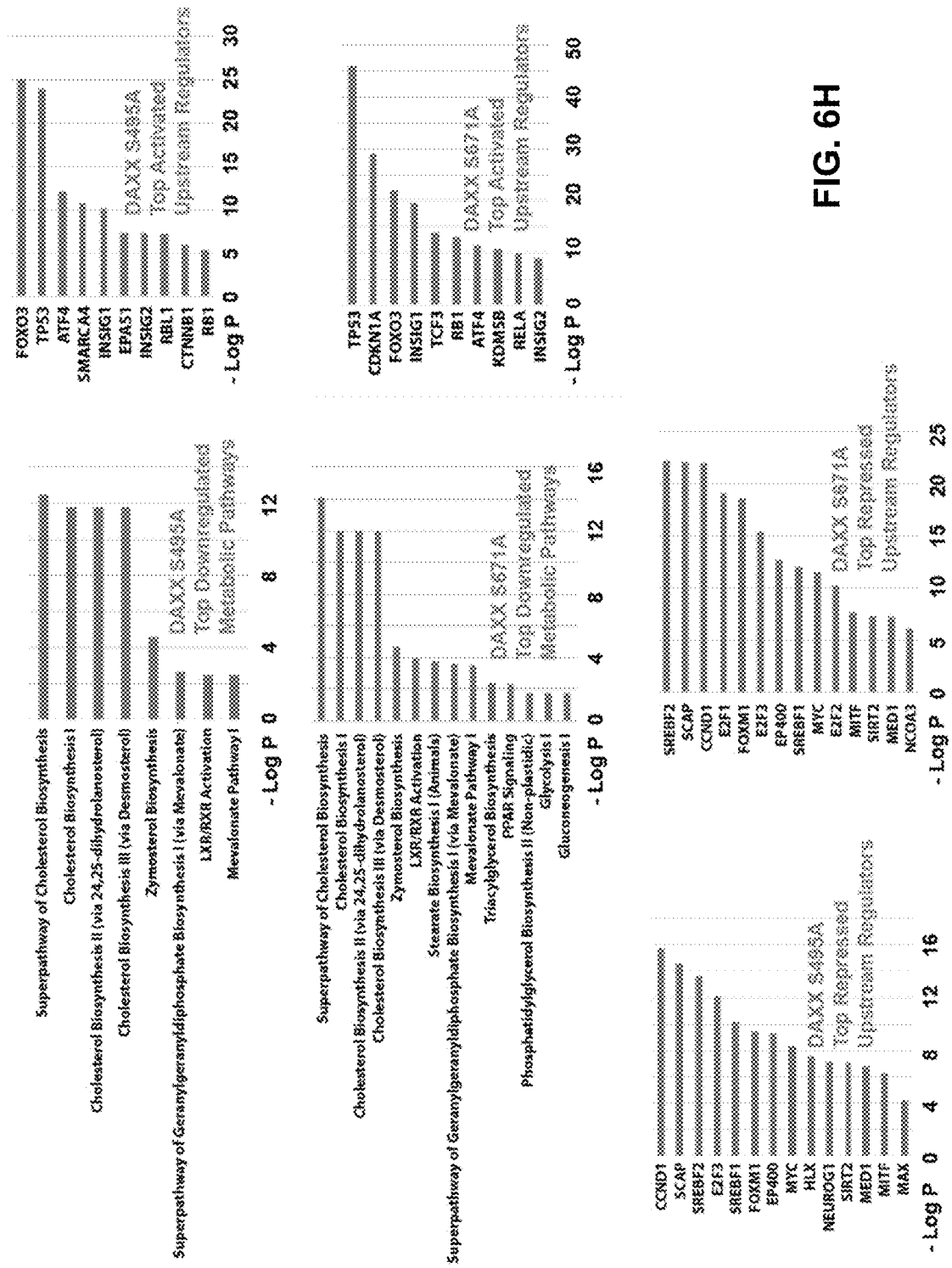

Lipidomic profiling of the xenograft tumors revealed that lipid production was impaired in tumors expressing the DAXX S671A or S495A mutant (FIG. 6G). Gene expression profiling of MDA-MB-231 cells expressing the DAXX S671A or the S495A mutant revealed that the lipogenesis pathways, especially the cholesterol biosynthesis pathway, were markedly suppressed. Significantly, repressed glycolysis was also observed in cells expressing the DAXX S671A mutant. Among the repressed transcriptional activators, SREBP1/2 and MYC ranked among the top inhibited upstream regulators (FIG. 6H). Interestingly, transcription factors that promote cell cycle progression such as E2Fs and FOXM1 also emerged as highly repressed upstream regulators. Conversely, upstream regulators that suppress lipogenesis (INSIG1 and INSIG2) and cell cycling (e.g., TP53, CDKN2A, and RB) were activated in the IPA analysis. Collectively, these results establish a critical role for the DAXX-SREBP interaction in driving lipogenesis and tumor growth.

The S1M2 Peptide Blocks De Novo Lipogenesis and Inhibits Tumor Growth

The data presented above indicate the DAXX's SUMO-binding property is critical to de novo lipogenesis and in vivo tumor growth. It was hypothesized that the interface between DAXX SIMs and SUMOs can be targeted for cancer therapy. To test this hypothesis, a peptide corresponding to the C-terminal 12 amino acids of DAXX (amino acids 729-740) was synthesized. This synthetic peptide encompasses the C-terminal SUMO-interacting motif of DAXX (termed SIM2). Remarkably, SIM2 was spontaneously and rapidly internalized into cells (FIG. 18A). Thus, SIM2 is a naturally cell membrane permeable peptide that does not require specific modification such as hydrocarbon staple or attaching to a cell-penetrating sequence (Fosgerau K, et al. Drug Discov Today 2015 20(1):122-8). SIM2 bound to SUMO1 in vitro (FIG. 18B) and blocked de novo lipogenesis in diverse types of cancer cells including breast (MDA-MB-231, MDA-MB-468 and Hs578T), prostate (R1-AD1 and R1-D567), colon (HCT116), and mouse tumor cells (4T1 and CT26.CL25) (FIG. 18C-18H). SIM2 also effectively inhibited de novo lipogenesis in MDA-MB-231 cells overexpressing DAXX (FIG. 18C). Further, SIM2 blocked the expression of lipogenic genes, and the inhibition appeared more potent when DAXX expression level was high (FIG. 18I).

Figure 7D:
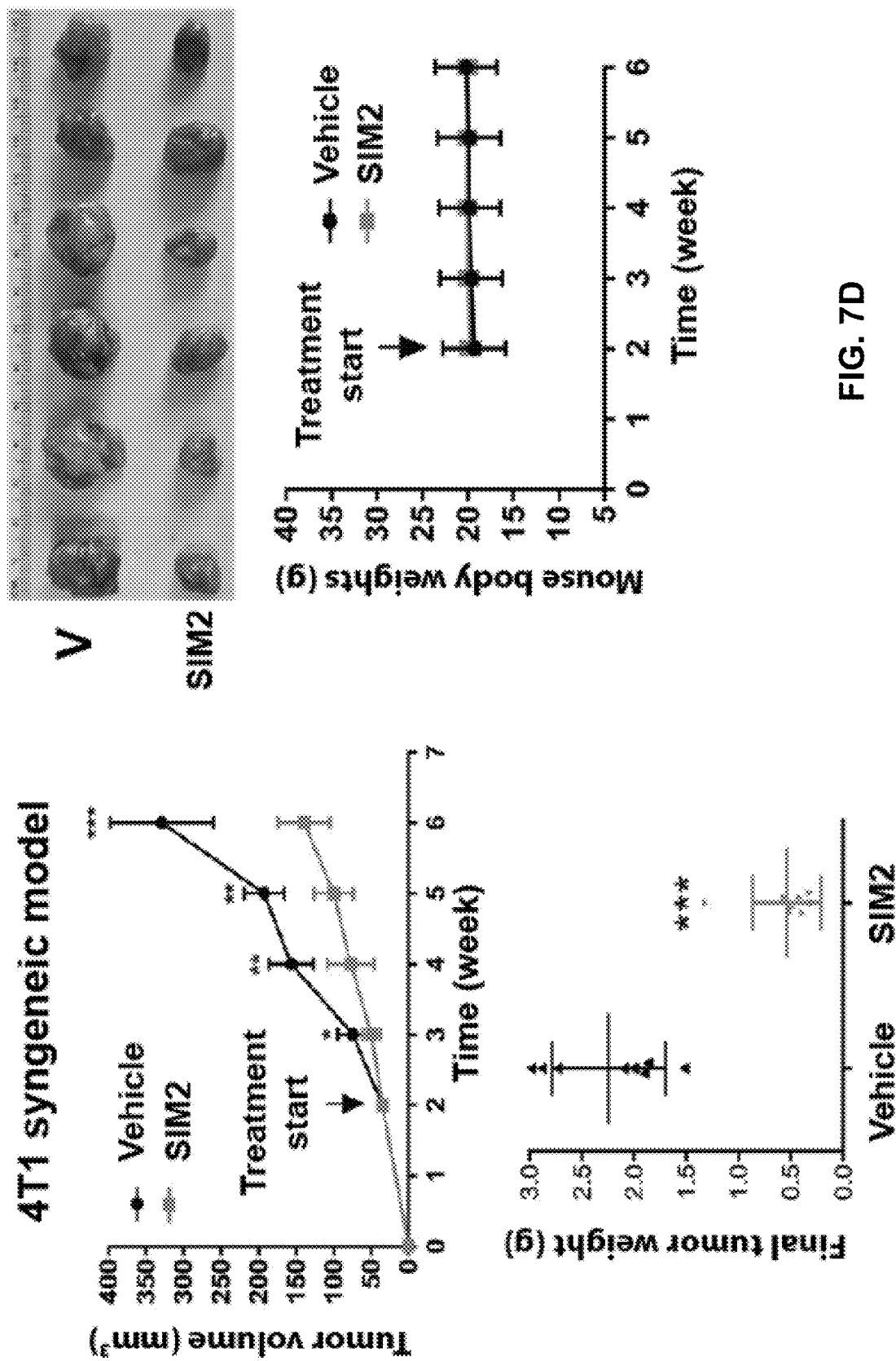
Figure 7E:
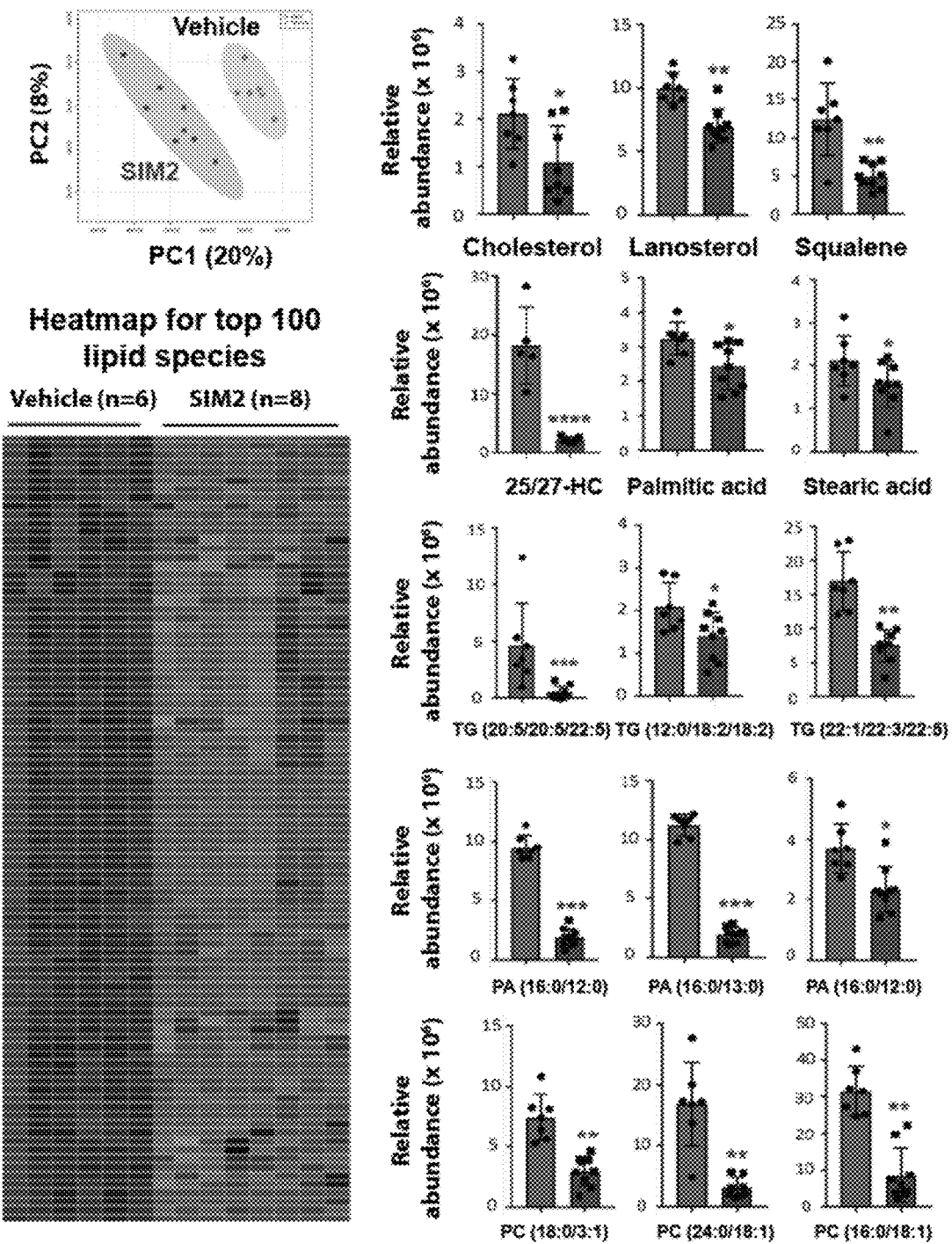
Figure 8A:
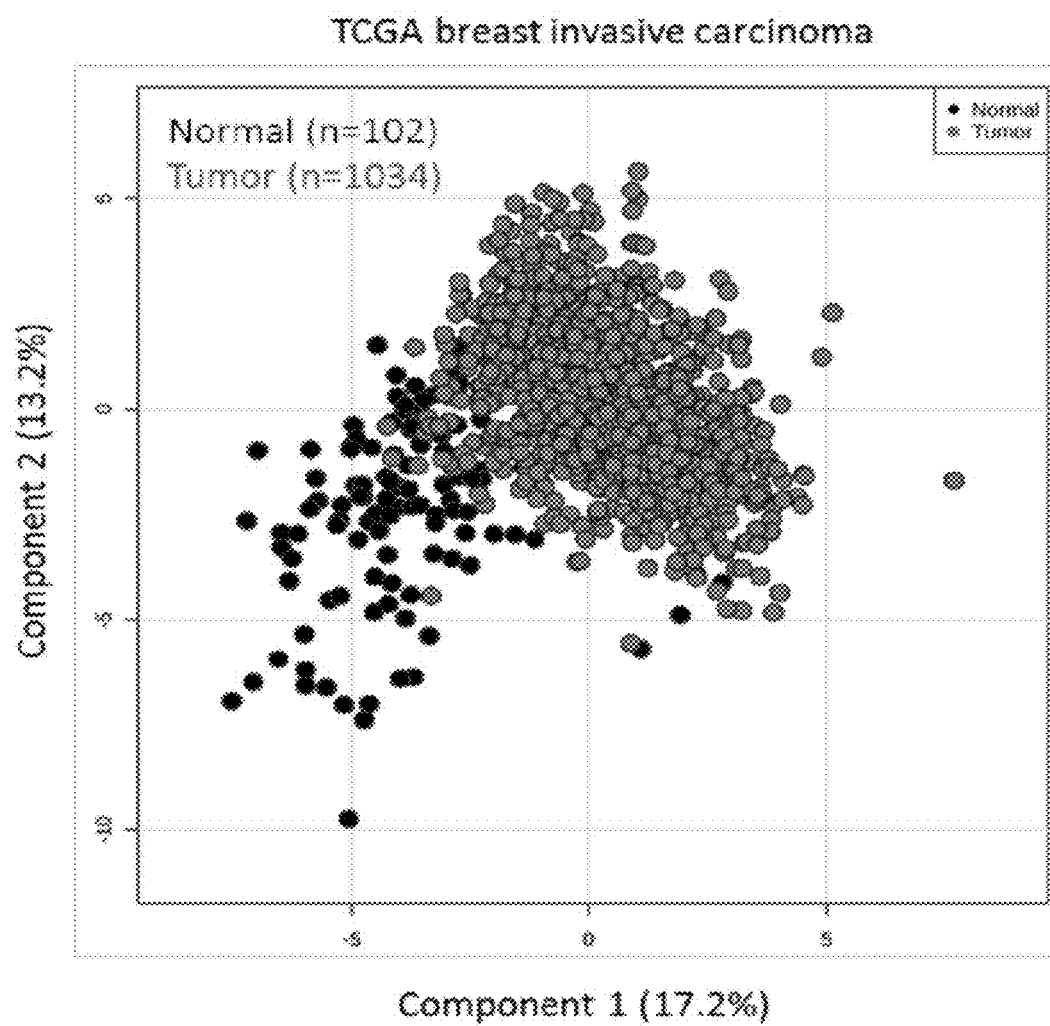
FIGS. 8A to 8G show DAXX and lipogenic genes are highly expressed in breast cancer.
Figure 8B:
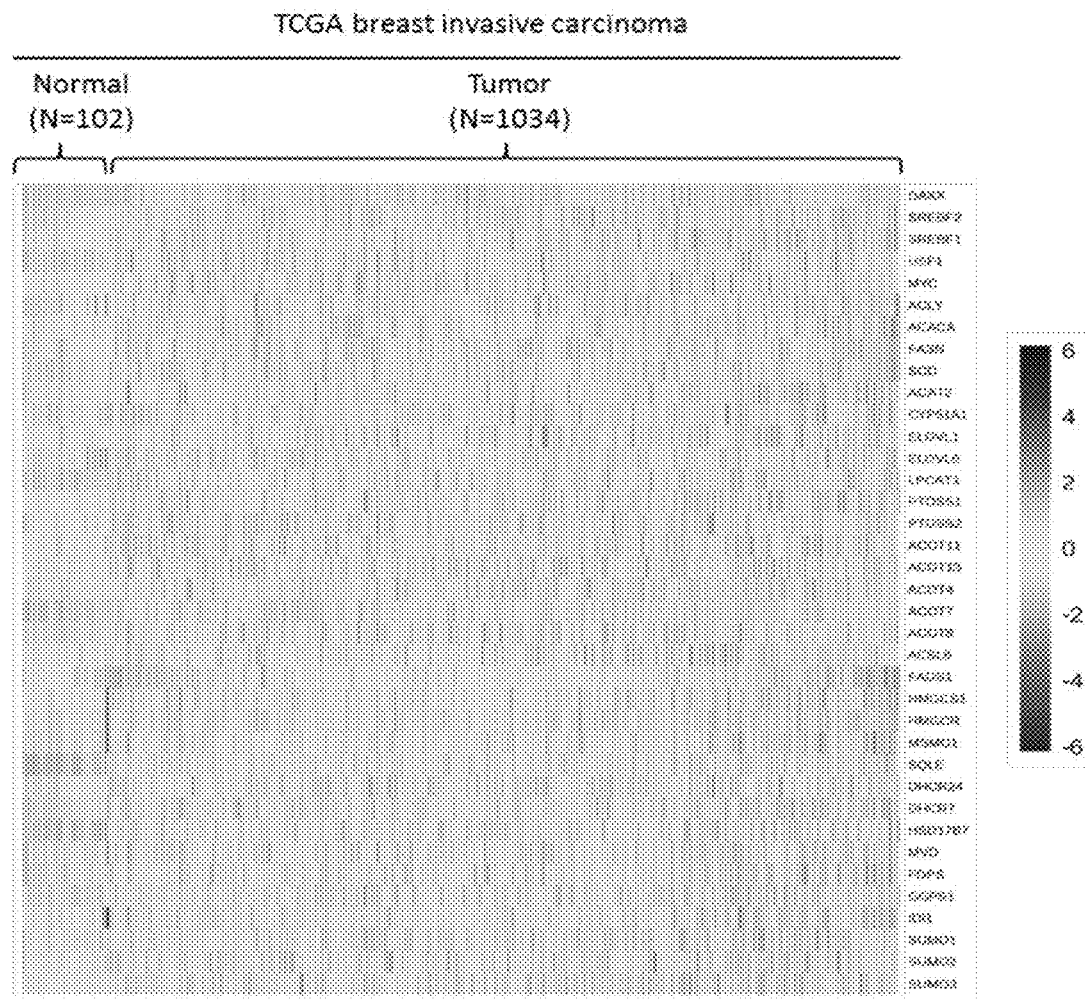
Figure 8C:
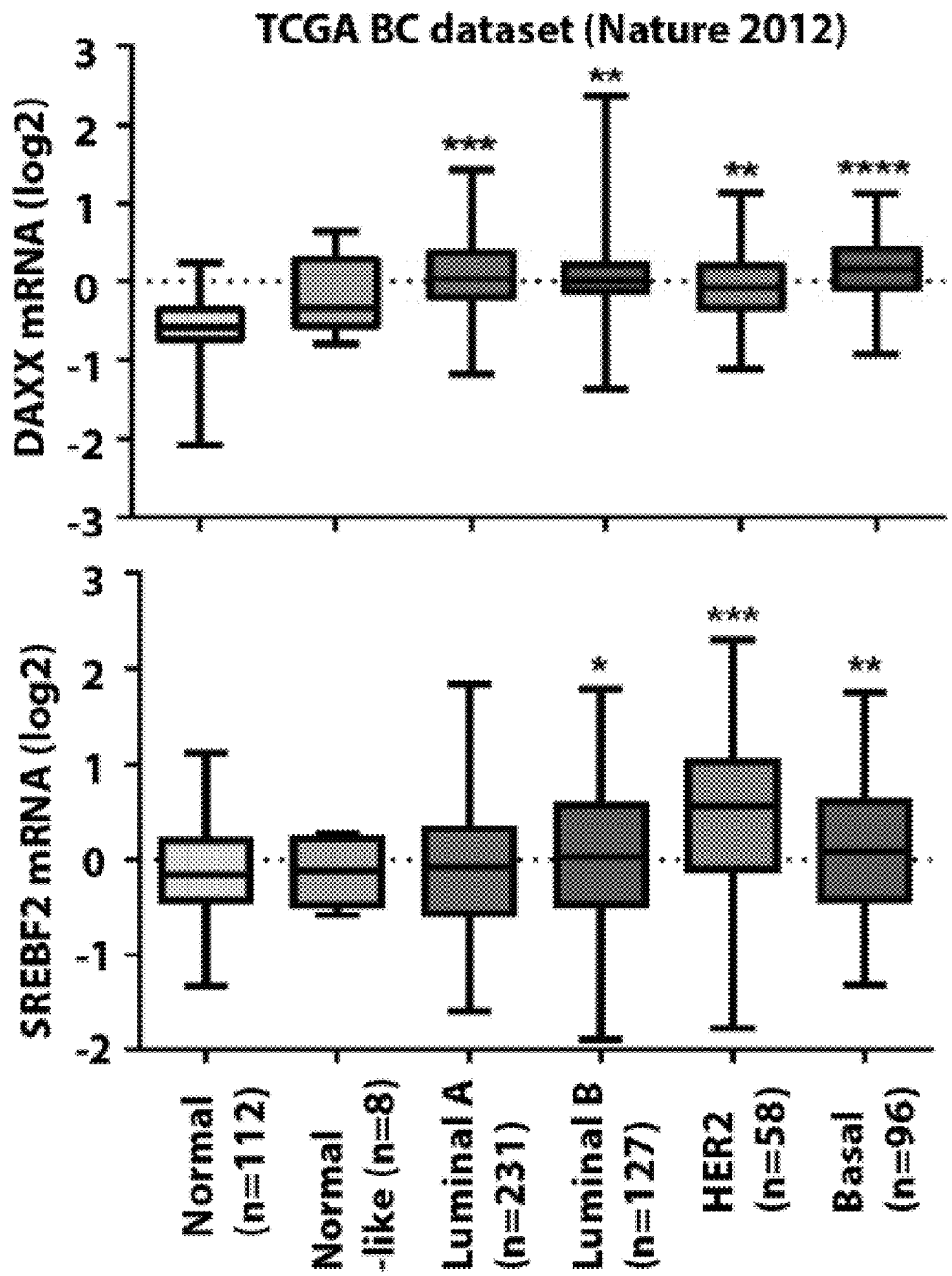
Figure 8D:
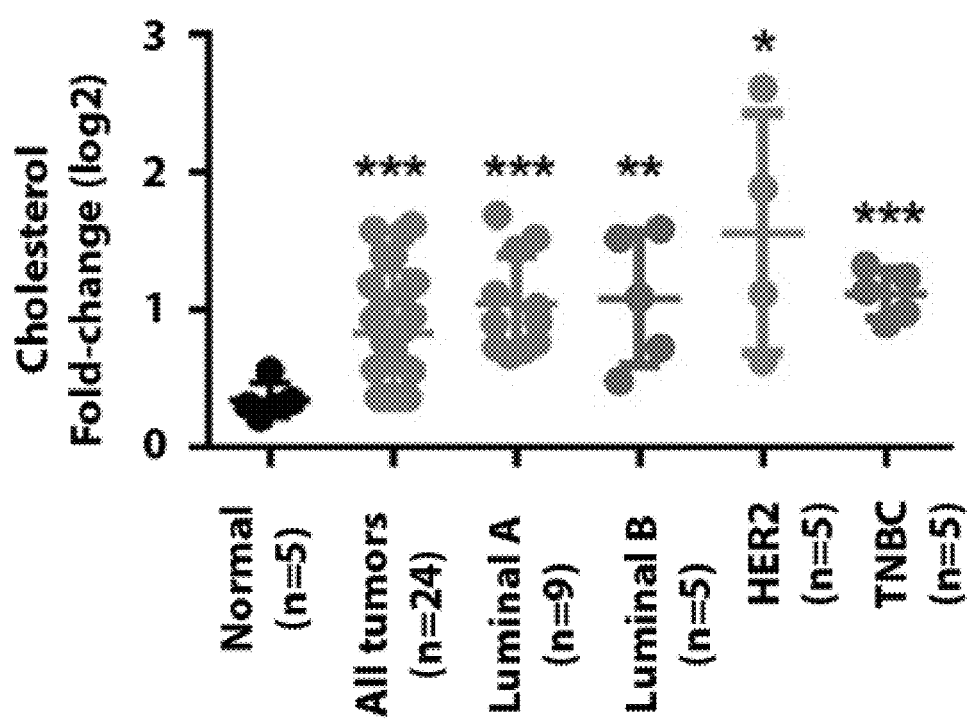
Figure 8E:
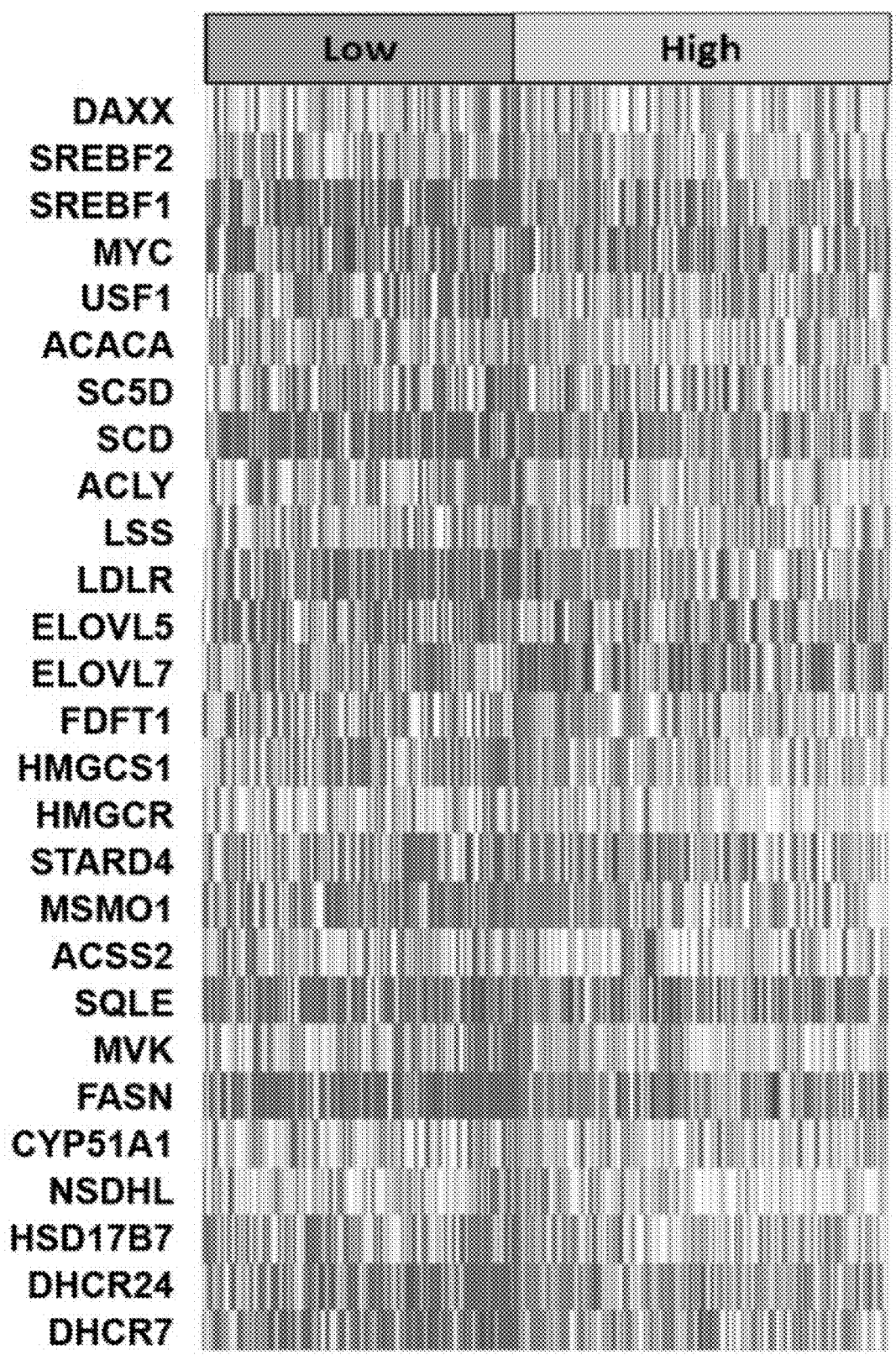
Figure 8F:
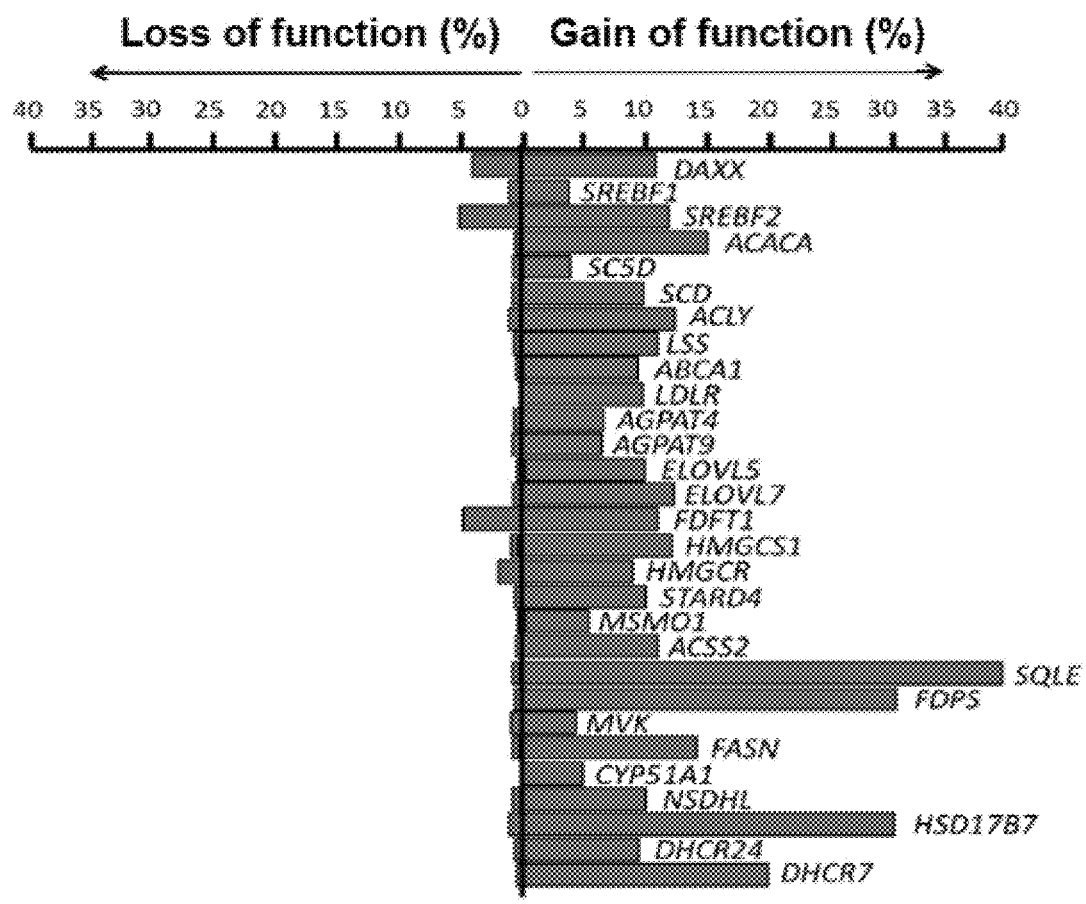
Figure 8G:
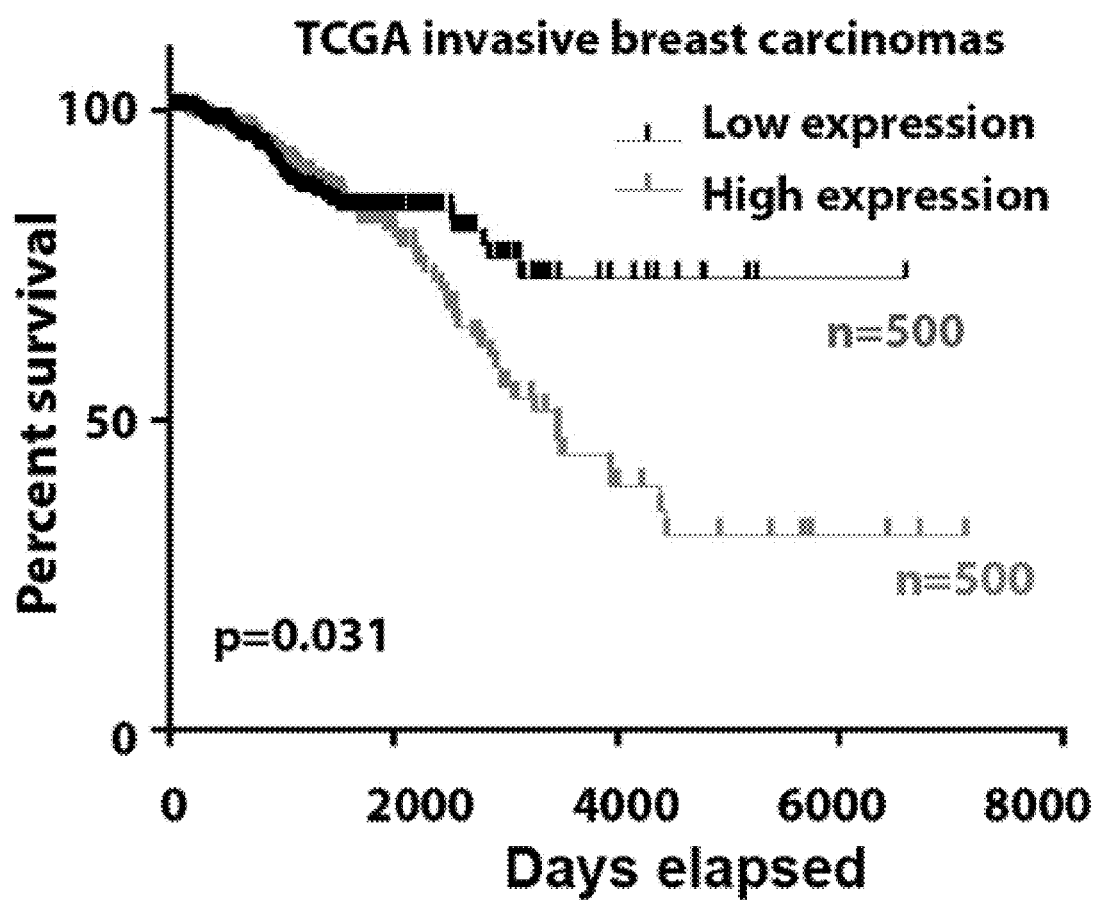

Mechanistically, SIM2 markedly inhibited the interaction of DAXX with full-length and mature SREBP1/2, while DAXX self-association and interaction with ATRX were only slightly affected (FIG. 7A), suggesting that SIM2 preferentially blocks the DAXX-SREBP interaction. To test in vivo efficacy of SIM2 for inhibiting tumor growth, orthotopic human MDA-MB-231 xenograft tumors were generated in the mammary fat pads of female NSG mice. As shown in FIG. 7B, SIM2 significantly impeded tumor growth, and at the experimental endpoint, the tumor masses were much smaller in the SIM2 treatment group compared to the vehicle group. In a syngeneic mouse mammary tumor model, the mouse 4T1 cell line (derived from a spontaneous mouse mammary tumor with human basal/TNBC characteristics (Kaur P, et al. BMC Cancer 2012 12:120)) was transplanted into mammary fat pads of immunocompetent BALB/c mice. 4T1 tumor-bearing mice were dosed with vehicle or SIM2. Consistent with the MDA-MB-231 xenograft results (FIG. 7B), SIM2 was highly potent to inhibit the 4T1 tumor growth (FIG. 7D). To understand potential mechanism of action for SIM2, MDA-MB-231 tumor extracts were subjected to immunoblotting. Interestingly, the protein levels of DAXX, SREBP2, and FASN were lower in the SIM2 treatment group compared to the control group (FIG. 7C), suggesting that SIM2 acts to downregulate the DAXX-driven lipogenesis pathway. Lipidomic profiling of MDA-MB-231 xenograft tumor samples from each treatment group revealed a marked suppression of lipid production by SIM2 (FIG. 7E). Overall, these data indicate that the SIM/SUMO interface represents a tractable therapeutic target to inhibit de novo lipogenesis for cancer therapy. These data also highlight the therapeutic potential of SIM2 as a class of cancer therapeutics.

Discussion

Lipid availability for proliferating cells determines the activity of intracellular lipid biosynthesis pathway. In a nutrient-poor tumor microenvironment, limited supplies of lipids necessitate the activation of intracellular lipid production in tumor cells for sustained tumor growth. An elaborate sterol sensing mechanism controls the nuclear translocation of SREBP1/2, which promote the expression of enzymes required for de novo lipogenesis (Rohrig F, et al. Nat Rev Cancer 2016 16(11):732-49; Bengoechea-Alonso M T, et al. Curr Opin Cell Biol 2007 19(2):215-22). SREBP1/2 in conjunction with several transcription factors, such as the E-box-binding basic helix-loop-helix (bHLH) transcription factor USF1, activate the expression of lipogenic enzymes and regulators (Wang Y, et al. Nat Rev Mol Cell Biol 2015 16(11):678-89). Other coregulators of gene expression such as acetyltransferases (e.g., p300 and PCAF) as well as oncogenic signaling pathways (e.g., KRAS and mTOR) also play important roles in stimulating de novo lipogenesis (Ricoult S J, et al. Oncogene 2016 35(10):1250-60). DAXX is shown here to be critical for de novo lipogenesis. Mechanistically, DAXX interacts with SREBP1/2 and is enriched in chromatins containing SRE motifs. Importantly, DAXX mutants that cannot bind SREBP2 are unable to promote lipogenesis and tumor growth. Thus, DAXX enhances lipogenesis through interacting with SREBP1/2 to promote lipogenic gene expression. Most significantly, the SUMO-binding property of DAXX is critical for de novo lipogenesis and tumor growth, and the DAXX/SUMO interface could be targeted to inhibit lipogenesis and tumor growth.

Consistent with a critical role for the DAXX SUMO-binding activity in DAXX's chromatin recruitment, lipogenic gene expression and hence tumor growth, the SIM2 peptide corresponding to the C-terminal SIM of DAXX blocks de novo lipogenesis and potently inhibits in vivo tumor growth (FIG. 7 and FIG. 18). Mechanistically, SIM2 blocks DAXX-SREBP1/2 interaction, and SIM2 treatment results in reduced lipid levels and the downregulation of DAXX, SREBP2, and FAS in vivo (FIG. 7). Thus, the inhibition of the DAXX/SREBP pathway by SIM2 blocks de novo lipogenesis and potentially other critical mechanisms underpinning aggressive tumor growth, which may underlie SIM2-mediated antitumor effects. The SIM2 peptide has a unique sequence and displays a high affinity to SUMO1 (Santiago A, et al. Cell Cycle 2009 8(1):76-87; Chang C C et al. Mol Cell 2011 42(1):62-74) (FIG. 18B). In general, peptides are not permeable through cell membranes. However, SIM2 is spontaneously and rapidly internalized into cells (FIG. 18A). Importantly, the SIM2 peptide was highly tolerated in vivo (FIG. 7). The discovery of SIM2 as a class of therapeutics has immediate implications for developing peptide drugs. Overall, these findings indicate that SIM2, through a new anticancer mechanism of action, has an exciting potential for translation into the clinic for treating cancer.

These results imply that the interaction between DAXX and SREBP2 is regulated through site-specific phosphorylation. Specially, converting S495 and S671, the two most frequently phosphorylated sites (FIG. 17A), to un-phosphorylatable alanine, abolished the DAXX-SREBP2 interaction (FIG. 6A). Remarkably, both DAXX S495A and S671A mutants are defective in promoting lipogenic gene expression, lipid production and tumor growth (FIG. 6). These results suggest that the DAXX-SREBP2 axis is subject to regulation by protein phosphorylation. Although how DAXX phosphorylation regulates the DAXX-SREBP interaction remains to be determined, it has been well documented that phosphorylation alters protein structure and protein-protein interaction (Dick F A, et al. Nat Rev Mol Cell Biol 2013 14(5):297-306). Notably, a previous study indicates that phosphorylation at the serine in mouse Daxx equivalent to S495 of the human DAXX is regulated (Ecsedy J A, et al. Mol Cell Biol 2003 23(3):950-60). Currently, the kinases that phosphorylate S495 and S471 remain unknown. The identification of such kinases may define signaling mechanisms that govern the DAXX-SREBP axis, and more importantly, may have translational potential, as kinase inhibitors that block DAXX phosphorylation may effectively inhibit oncogenic lipogenesis and tumor growth.

Biochemically, DAXX's oncogenic function through promoting lipogenesis could be separated from its well-defined histone H3.3 chaperone function (Lewis P W, et al. Proc Natl Acad Sci USA 2010 107(32):14075-80; Goldberg A D, et al. Cell 2010 140(5):678-91; Drane P, et al. Genes Dev 2010 24(12):1253-65). Indeed, S495A mutant, despite being capable of H3.3 binding (FIG. 17C), fails to promote lipogenic gene expression and tumor growth (FIG. 6). In contrast, the H3.3-binding defective DAXX Y222P mutant retains the ability to promote tumor growth (FIG. 6). Notably, DAXX's histone binding activity stabilizes DAXX protein (Hoelper D, et al. Nat Commun 2017 8(1):1193). In keeping with this observation, the DAXX Y222P mutant was expressed at a low level (FIG. 17C). Furthermore, DAXX S671A mutant did not bind H3.3 and this mutant accumulated to a much lower level than wt DAXX and the S495A mutant (FIG. 17C). Interestingly, cells expressing DAXX S671A mutant are more profoundly impaired in lipogenic and cell cycle gene expression, lipogenesis, and tumor growth (FIG. 6). Indeed, these data indicate that the DAXX S671A mutant appears to exhibit a dominant negative effect on tumor growth compared to the S495A mutant. Thus, although the histone chaperone function of DAXX per se is not required for DAXX's oncogenic activity, stabilization of DAXX through histone binding may contribute indirectly to oncogenesis.

These data also suggest that the DAXX-ATRX interaction is not involved in DAXX's oncogenic function. Indeed, DAXX mutants S495A and S671A that could not enhance lipogenesis or tumorigenesis retain the ability to bind ATRX (FIG. 17C), but these mutants are defective in promoting lipid production and tumor growth. The DAXX-ATRX interaction plays an important role in depositing the histone variant H3.3 to telomeric heterochromatin regions and gene repression (Lewis P W, et al. Proc Natl Acad Sci USA 2010 107(32):14075-80; Goldberg A D, et al. Cell 2010 140(5): 678-91; Drane P, et al. Genes Dev 2010 24(12):1253-65; Hoelper D, et al. Nat Commun 2017 8(1):1193). In mouse embryonic stem cells, Daxx and Atrx co-occupy and transcriptionally silence tandem repetitive elements including telomeres through promoting histone H3K9 trimethylation (He Q, et al. Cell Stem Cell 2015 17(3):273-86). More recent studies have shown that the DAXX-ATRX complex represses endogenous retroviruses in an H3.3-dependent fashion and through engaging the SETDB1, KAP1 and HDAC co-repressors (Hoelper D, et al. Nat Commun 2017 8(1):1193; Elsasser S J, et al. Nature 2015 522(7555):240-4). Notably, pancreatic neuroendocrine tumors and other tumor types exhibit frequent loss-of-function mutations of both DAXX and ATRX (Jiao Y, et al. Science 2011 331 (6021):1199-203). Interestingly, tumor-derived missense mutations in DAXX occur most frequently in the two structurally defined and evolutionarily conserved DHB and HBD domains in DAXX, which bind ATRX and H3.3/H4 dimer, respectively (Hoelper D, et al. Nat Commun 2017 8(1):1193). It was shown that Men1/Daxx/Atrx complex-mediated gene repression underlies tumor suppression in murine neuroendocrine tumor models (Feng Z, et al. Cancer Res 2017 77(2):401-11). Thus, the putative tumor suppressor activity of DAXX may be linked to ATRX binding, H3.3 deposition, and gene silencing. However, DAXX is rarely mutated in breast cancer and other epidemiologically prevalent cancer types. Of note, ATRX-independent oncogenic function of DAXX was also implicated in glioblastoma (Benitez J A, et al. Nat Commun 2017 8:15223). Taken together, DAXX's oncogenic function may derive from its activity to promote gene expression required for increased lipogenesis and perhaps also for cell cycle progression, which is independent of its association with ATRX.

In summary, this study establishes DAXX as a key regulator of oncogenic lipogenesis. Molecularly, DAXX interacts with SREBPs to stimulate lipogenic gene expression, thereby promoting tumor growth. The DAXX-SREBP2 interaction may be regulated through phosphorylation. Importantly, DAXX's SUMO-binding property is critical for lipogenesis and the SIM2 peptide targeting the SUMO-SIM interface has potent anti-tumor efficacy.

Methods

Cell culture.

Cells were cultured in Dulbecco's Modified Eagle's Medium (DMEM with 4.5 g/L glucose, L-glutamine and sodium pyruvate; Corning) with 10% bovine calf serum (HyClone, GE Healthcare Bio-Sciences, Pittsburgh, PA), penicillin (10 units/ml), and streptomycin (10 µg/ml) (the complete DMEM medium). The T47D cell line was cultured in DMEM plus 10% fetal bovine serum (Atlanta Biologics, Atlanta, GA), penicillin (10 units/ml), and streptomycin (10 µg/ml). To culture cells in serum starvation condition, serum-containing medium was removed from cell cultures after overnight culture and the culture was washed once with phosphate-buffered saline (PBS, without calcium and magnesium, Corning). Cells were then cultured in serum-free DMEM. For culturing cells in suspension (3D culture), plates were coated with a 1:1 mixture of Matrigel (Corning, Tewksbury, MA) and complete DMEM medium. A desirable number of cells were suspended in the Matrigel and medium mixture and layered on the top of the solidified Matrigel. Complete DMEM medium was added after the Matrigel was solidified. Medium was replaced with fresh complete medium every three days. Colonies were imaged under a microscope; colony numbers and sizes were quantified. Human cell lines were obtained from ATCC (Manassas, VA) and authenticated by Genetica DNA Laboratories (Burlington, NC). The mouse cancer cell lines 4T1, CT26.CL25, and TRAMP-C2 were from ATCC. The mouse breast cancer cell line E0771 was from CH3 BioSystems (Amherst, NY).

Microarray, RNA-seq and qRT-PCR.

For microarray experiments, cells were cultured in the complete DMEM or serum-free DMEM, and total RNAs were isolated using the RNeasy kit (Qiagen). The RNAs were then processed for microarray hybridization to the Affymetrix GeneChip Human Transcriptome Array 2.0 as described previously (Wang Y, et al. Chem Biol 2015 22(2):273-84). RNA-seq was done with 20M raw reads/sample using Illumina Platform PE150 at Novogene Corporation Inc. (Sacramento, CA).

Following the RNAseq data analysis pipeline reported previously (Pertea M, et al. Nat Protoc 2016 11(9):1650-67), fastq files were aligned to Genome Reference Consortium Human Build 38 (GRCh38) using HISAT2 (Kim D, et al. Nat Methods 2015 12(4):357-60); the transcripts assembling was performed using StringTie (Pertea M, et al. Nat Biotechnol 2015 33(3):290-5) with RefSeq as transcripts ID; and the normalized counts (by FPKM) was called using Ballgown (Frazee A C, et al. Nat Biotechnol 2015 33(3): 243-6). The differential expression analysis was performed using R package limma (Smyth G K. Stat Appl Genet Mol Biol 2004 3:Article3); and the pathway enrichment analysis was performed using ingenuity pathway analysis.

For quantitative real-time PCR (qRT-PCR), the isolated RNAs were reverse transcribed with random hexamers using 2 µg of total RNA, an RNase inhibitor, and reagents in the Multiscribe reverse transcriptase kit (Life Technologies). The resulting cDNAs were diluted and used as input for qPCR using the SYBR green detection method. The relative levels of gene expression were determined using the ΔΔCt method with the Ct values of ACTB expression as the common normalizer. The primers for qPCR and other applications are provided below.

In microarray experiments, probe set files (.cel file) were normalized by RMA algorithm and analyzed using both R statistical package as well as Affymetrix expression and transcriptome console software from ThermoFisher Scientific.

TABLE 1

| PCR primers used for this study | |
| --- | --- |
| qPCR primers (5' to 3') | |
| ActinB-F-Real | GCTCCTCCTGAGCGCAAGTACTC (SEQ ID NO: 12) |
| ActinB-R-Real | GTGGACAGCGAGGCCAGGAT (SEQ ID NO: 13) |
| Daxx-RT-F3 | GAGGCGTCTCTCCTCACAAC (SEQ ID NO: 14) |

TABLE 1-continued

PCR primers used for this study

| | | |
|---|---|---|
| Daxx-RT-R3 | TCTCATGCACTGACCTTTGC | (SEQ ID NO: 15) |
| SREBP1-F1 | CTGCTGTCCACAAAAGCAAA | (SEQ ID NO: 16) |
| SREBP1-R1 | GGTCAGTGTGTCCTCCACCT | (SEQ ID NO: 17) |
| SREBP2-F1 | ATCGCTCCTCCATCAATGAC | (SEQ ID NO: 18) |
| SREBP2-R1 | TTCCTCAGAACGCCAGACTT | (SEQ ID NO: 19) |
| FASN-F1 | CACAGGGACAACCTGGAGTT | (SEQ ID NO: 20) |
| FASN-R1 | ACTCCACAGGTGGGAACAAG | (SEQ ID NO: 21) |
| ACACA-F1 | ACCACCAATGCCAAAGTAGC | (SEQ ID NO: 22) |
| ACACA-R1 | CTGCAGGTTCTCAATGCAAA | (SEQ ID NO: 23) |
| SCD-F1 | TGTTCGTTGCCACTTTCTTG | (SEQ ID NO: 24) |
| SCD-R1 | GGGGGCTAATGTTCTTGTCA | (SEQ ID NO: 25) |
| LDLR-F1 | GCGAAAGAAACGAGTTCCAG | (SEQ ID NO: 26) |
| LDLR-R1 | TGACAGACAAGCACGTCTCC | (SEQ ID NO: 27) |
| MSMO1-F1 | TGCTTTGGTTGTGCAGTCAT | (SEQ ID NO: 28) |
| MSMO1-R1 | TTCCAAATGGAGCCTGAAAC | (SEQ ID NO: 29) |
| INSIG1-F1 | TACGCTGATCACGCAGTTTC | (SEQ ID NO: 30) |
| INSIG1-R1 | TGACGCCTCCTGAGAAAAAT | (SEQ ID NO: 31) |
| INSIG2-RT-F1 | CATGCCAGTGCTAAAGTGGA | (SEQ ID NO: 32) |
| INSIG2-RT-R1 | TACTCCAAGGCCAAAACCAC | (SEQ ID NO: 33) |
| HMGCS1-F1 | GGGACACATATGCAACATGC | (SEQ ID NO: 34) |
| HMGCS1-R1 | CACTGGGCATGGATCTTTTT | (SEQ ID NO: 35) |
| HMGCR-F1 | GTCATTCCAGCCAAGGTTGT | (SEQ ID NO: 36) |
| HMGCR-R1 | CATGGCAGAGCCCACTAAAT | (SEQ ID NO: 37) |
| STARD4-F1 | GGCGAGTTGCTAAGAAAACG | (SEQ ID NO: 38) |
| STARD4-R1 | CCCTGGGCGTATATGGTCTA | (SEQ ID NO: 39) |
| SQLE-RT-F1 | GTCTCCGGAAAGCAGCTATG | (SEQ ID NO: 40) |
| SQLE-RT-R1 | CAGTGGAGCATGGAGTTCCT | (SEQ ID NO: 41) |
| ACSS2-F1 | ATTGACTTGTGGTGGCATGA | (SEQ ID NO: 42) |
| ACSS2-R1 | CTGTGTGAACCACACCCTTG | (SEQ ID NO: 43) |
| ACLY-F1 | TGCCGACTACATCTGCAAAG | (SEQ ID NO: 44) |
| ACLY-R1 | GGTTCAGCAAGGTCAGCTTC | (SEQ ID NO: 45) |
| H3F3A-RT-F1 | TGATTCGCAAACTTCCCTTC | (SEQ ID NO: 46) |
| H3F3A-RT-R1 | GTCTTCAAAAAGGCCAACCA | (SEQ ID NO: 47) |
| BIRC5-F1 | GCCCAGTGTTTCTTCTGCTT | (SEQ ID NO: 48) |
| BIRC5-R1 | TCTCCGCAGTTTCCTCAAAT | (SEQ ID NO: 49) |
| ATRX-RT-F1 | AGTAGACAAGCCAGCCAGGA | (SEQ ID NO: 50) |
| ATRX-RT-R1 | GTACTGCTGCTGGAGCCTTC | (SEQ ID NO: 51) |

TABLE 1-continued

PCR primers used for this study

ChIP primers

| | |
|---|---|
| FASN-prom-F1 | TAGAGGGAGCCAGAGAGACG (SEQ ID NO: 52) |
| FASN-prom-R1 | GCTGCTCGTACCTGGTGAG (SEQ ID NO: 53) |
| ACACA-prom-F1 | CAAGGGAAATTGAGGCTGAG (SEQ ID NO: 54) |
| ACACA-prom-R1 | CGTTCCAGGAGCATCTGATT (SEQ ID NO: 55) |
| DAXX-ChIP-F1 | ACTGTTGGGAGGGAACCTCT (SEQ ID NO: 56) |
| DAXX-ChIP-R1 | CCCCTCTGCTCTCAAACAAG (SEQ ID NO: 57) |
| FASN-ChIP-3p-F1 | GTGAACCATGACTGCACCAC (SEQ ID NO: 58) |
| FASN-ChIP-3p-R1 | GAGCCCTCGGTGACATACAT (SEQ ID NO: 59) |
| ACACA-ChIP-3p-F1 | TCATGGCCAAACTGTTGAAA (SEQ ID NO: 60) |
| ACACA-ChIP-3p-R1 | TGGGGTCCATTGTTTCTGAT (SEQ ID NO: 61) |

Primers for amplifying a fragment in the SREBF2 promoter

| | |
|---|---|
| SREBF2-prom-F1 | CAGCTGAAGCTTGCATGCCTGCAGGTAGGCAGCTGGGA AGATGA (SEQ ID NO: 62) |
| SREBF2-prom-R1 | GAGTATATATAGGACTGGGGATCCGTGAGGGTCTCCATG GTCTC (SEQ ID NO: 63) |

Note:
The sequences in red are specific to the SREBF2 promoter region; and the sequences in black correspond to the cloning vector DNA Constructs.

cDNAs for wild-type (wt) DAXX and mutants (17K/1733K, DSM), Y124F/Y126F, Y222P, S495A, S561A, K630A/K631A, S668A, S671A, S668A/S671A, S690A, and deICT) with a 5' coding sequence for the FLAG epitope tag and a 3' coding sequences for the MYC and 6× His tags were cloned into a lentiviral vector under the control of the cytomegalovirus immediate early (CMV IE) promoter. GFP-DAXX constructs were cloned in the pEGFP-C2 vector. A short hairpin RNA (shRNA) target the DAXX coding sequence (nucleotide 624-642, 5'-GGAGTTG-GATCTCTCAGAA-3', SEQ ID NO:64) was cloned into a lentiviral vector under the control of the human U6 promoter. An shRNA construct with a scrambled sequence (Plasmid #36311) was from Addgene. Expression vectors for mature SREBP1a (Plasmid #26801), mature SREBP1c (Plasmid #26802), mature SREBP2 (Plasmid #26807), full-length SREBP1 (Plasmid #32017) and SREBP2 (Plasmid #32018) were purchased from Addgene. The shRNA clones for SREBF1 (TRCN0000020607 and TRCN0000020605), and SREBF2 (TRCN0000020667 and TRCN0000020668) were from the human pLKO.1 TRC Library collection at the University of Florida. The SREBF2 shRNA vector TRCN0000020667 was used to knockdown SREBF2 expression in MDA-MB-231 cells with DAXX OE. A SREBP2 promoter fragment was PCR amplified from the genomic DNA isolated from MDA-MB-231 cell line, and cloned at sites upstream of the firefly luciferase reporter by the Gibson assembly method. The DNA sequence was confirmed by Sanger sequencing. The PCR primers are shown in Table 1.

Stable expression of cDNA and shRNA was established through lentiviral transduction of cell lines and puromycin (2 µg/ml) selection. The derived cell lines were cultured with DMEM without puromycin.

Immunoprecipitation (IP) and Immunoblotting.

Cell pellets were resuspended in the IP lysis buffer (50 mM Tris-HCl, pH 7.5, 0.5% Igepal-CA630, 5% glycerol, 150 mM NaCl, 1.5 mM MgCl2, and 25 mM NaF) containing 100-fold diluted protease inhibitor cocktail (Millipore-Sigma P8340). The cell suspension was subjected to two freezing/thawing cycle. The cell lysates were then centrifuged at 15,000 rpm at 4° C. for 20 min. The supernatant was used for IP with a control or an antibody to a specific protein at 2 µg per IP in the presence of protein A-agarose beads. For IPs in the presence of the SIM2 peptide, SIM2 in PBS was added to a desirable concentration. IP mixtures were rotated at 4° C. overnight. The beads were washed four times with the IP lysis buffer and once with the RIPA buffer (50 mM Tris-HCl, pH 7.4, 150 mM NaCl, 1% NP-40, 0.5% sodium deoxycholate). The beads were resuspended in the IP lysis buffer along with one fifth of the volume of the 6× SDS sample buffer (0.375 M Tris-HCl, pH 6.8, 12% SDS, 60% glycerol, 0.6 M DTT, and 0.06% bromophenol blue). Samples were heated at 95° C. for 5 min and chilled on ice for 2 min. After brief centrifugation, the samples were loaded on a 4-20% gradient gel (Novex Tris-Glycine Mini Gels, ThermoFisher). Proteins were then electrotransferred to an Immobilon®-P polyvinylidene fluoride (PVDF) membrane (Millipore). Membrane was blocked with 5% non-fat milk, incubated with a primary antibody and a proper secondary antibody. The proteins were detected using a chemiluminescent detection kit (Millipore) and the Fuji Super RX-N X-ray films.

For immunoblotting analyses of cell lysates of monolayer cultures, medium was removed from culture plates and 1× Passive Lysis buffer (Promega) was added. The plates were frozen at −80° C. overnight and then thawed at room temperature. The lysates were transferred to a centrifuge tube. To prepare tumor lysates, xenograft tumor tissues were fragmented in the presence of liquid nitrogen, approximately 50 mg of tumor fragment was homogenized in 1 mL of 1× RIPA lysis buffer on ice using a micro-homogenizer. After brief sonication at a low power output for 5 sec on ice, the lysates were cleared by centrifugation at 13,000 rpm for 15 min at 4° C. Protein contents were quantified using a Qubit protein assay kit. Protein extracts from cell culture or tumor lysates were subjected to SDS-PAGE and electro-blotting as above. The antibodies used for this study are listed in Table 2.

17:0), phosphatidylserines (PS, 14:0/14:0 and 17:0/17:0), and phosphatidylglycerols (PG, 14:0/14:0 and 17:0/17:0) (Avanti Polar Lipids, Alabaster, AI). The lipid standards were dissolved in 2:1 (v/v) chloroform:methanol to make a 1000 ppm stock solution and a working 100 ppm standard mix was then prepared by diluting the stock solution with the same solvent mixture. For sample normalization, total protein concentration in each sample was determined using a Qubit 3.0 Fluorometer.

TABLE 2

Antibodies used in this study

| Antibody target | Vendor | Vendor catalog # | Dilution |
|---|---|---|---|
| DAXX | Bethyl laboratories | A301-352A | 1:20,000 (WB) |
| DAXX | Bethyl laboratories | A301-353A | 1:20,000 (WB) |
| DAXX (for IP, WB and ChIP) | The Developmental Studies Hybridoma Bank | PCRP-DAXX-5G11 | 1:100 (hybridoma supernatant) |
| FASN (for WB and IF) | ProteinTech | 10624-2-AP | 1:20,000 (WB) 1:700 (IF) |
| FASN | Santa Cruz | SC-55580 | 1:20,000 (WB) |
| ACC1 | Cell Signaling Technology | 3676 | 1:20,000 (WB) |
| INSIG1 | Santa Cruz | SC-390504 | 1:20,000 (WB) |
| ACLY | Cell Signaling Technology | 13390 | 1:10,000 (WB) |
| ACSS2 | Cell Signaling Technology | 3658 | 1:20,000 (WB) |
| SREBP2 | Cayman Chemical | 10007663 | 1:10,000 (WB) |
| SREBP2 | Bethyl laboratories | A303-125A | 1:10,000 (WB) |
| SREBP1 | Santa Cruz | SC-13551 | 1:5,000 (WB) |
| SREBP1 | ProteinTech | 4088-1-AP | 1:10,000 (WB) |
| FLAG | Cell Signaling Technology | 14793 | 1:10,000 (WB) |
| FLAG (WB, IP and ChIP) | Millipore-Sigma | F1804 | 1:1,000 (WB) |
| GFP | Cell Signaling Technology | 2956 | 1:10,000 (WB) |
| PCNA | Epitomics | 2714-1 | 1:50,000 (WB) |
| alpha-Tubulin | Millipore-Sigma | T5168 | 1:50,000 (WB) |
| HSP60 | BD Transduction Laboratories | H99020 | 1:50,000 (WB) |
| Rabbit IgG HRP-linked antibody | Cell Signaling Technology | 7074 | 1:10,000 (WB) |
| Mouse IgG HRP-linked antibody | Cell Signaling Technology | 7076 | 1:10,000 (WB) |
| Normal mouse IgG (for IP control) | Santa Cruz | SC-2025 | |

De Novo Lipogenesis Assays

Cells (0.5 million per well) were plated in a 6-well plate in complete DMEM medium in triplicate. At 24 h after seeding, cells were washed once with PBS and cultured in serum-free DMEM for 16 to 18 h; 5 µCi of [1-$^{14}$C] acetate (NEC084H001MC, Perkin Elmer, Waltham, MA, USA) per ml was added and the cells were cultured for four more hours. Cells were then washed twice with PBS and trypsinized. Cells were pelleted and resuspended in 0.5 ml of 0.5% Triton X-100. The protein concentration of the lysates was determined for normalization. The lysates were extracted with ice cold chloroform/methanol (2:1 v/v). After centrifugation at 1,000 rpm for 20 min, the organic phase was collected and air dried. The radioactivity was determined with a liquid scintillation counter (Beckman L S 5000TD). The radioactivity was normalized against protein concentration.

Liquid Chromatography (LC)-Mass Spectrometry (MS) Experiments.

For lipid analysis, these internal lipid standards were used: triglyceride (TG 15:0/15:0/15:0 and TG 17:0/17:0/17:0, Sigma-Aldrich), lysophosphatidylcholines (LPC, 17:0 and 19:0), phosphatidylcholines (PC, 17:0/17:0 and 19:0/19:0), phosphatidylethanolamines (PE, 15:0/15:0 and 17:0/

Cell lines with shControl, shDAXX, wt DAXX overexpression (wt OE), and the DSM mutant overexpression (DSM OE) were cultured with the complete DMEM. When cells grew to approximately 80% confluency, they were washed twice with PBS and cells were detached using a cell lifter.

Cell pellets were washed twice with 40 mM ammonium formate (AF). The cell pellets were resuspended in 50 µL of AF with vortex in a glass vial and subjected to high efficient bead beater cell disruption to release intracellular lipids. A small amount of the homogenized cell pellet was taken for Qubit protein concentration determination. Lipids were extracted by adding ice-cold chloroform (2 mL) and methanol (1 mL) along with 20 µL of internal standard mixtures. The extraction mixture was incubated on ice for 1 h with occasional vortex mixing. Finally, 1 mL $H_2O$ was added to the mixture, which was incubated for 10 min with occasional vortex mixing. Samples were then centrifuged at 2,000 rpm for 5 minutes. The lower phase (organic layer) was collected in a separate glass vial and subjected to dry under nitrogen gas at 30° C. using a dryer (MultiVap, Organomation Associates). Dried samples were reconstituted by adding 50 µL isopropyl alcohol and transferred to a glass LC vial with insert. Samples were loaded to an auto-sampler at 5° C.

For analyzing lipids, samples were run for quality control (QC) in each instrument run. A pooled QC sample (a 25 μL aliquot) for each extraction was injected after analyzing every five samples. The pooled QC sample was run to assess system reproducibility, and a blank (solvent mixture only) was used to flush the column. No changes were observed regarding the number of background ions, which always corresponded to the specific solvent used for lipid extraction. Also, no effects on reproducibility of ion source was observed regardless of solvents used for extraction. The stability and repeatability of the instruments were evaluated using identical neat QC samples (a mixture of all internal standards in deuterated form) throughout the process of sample injection. Principal component analysis (PCA) was performed to evaluate the variation of QC samples. All neat QC samples clustered together, confirming the stability and reproducibility of our experimental lipid analysis system.

For data collection, processing, and analysis, a Dionex Ultimate 3000 UHPLC system coupled to a Q Exactive™ hybrid quadrupole-orbitrap mass spectrometer operated in HESI-positive and negative ion mode was used. A Supelco Analytical Titan reverse-phase column (RPC) C18 (2.1×75 mm with 1.9 μm monodisperse silica) equilibrated at 30° C. with solvents A (acetonitrile and water 60:40, v/v) and B (isopropyl alcohol, acetonitrile, and water 90:8:2, v/v/v) as mobile phases was used for data collection. The flow rate was 0.5 ml/min, and the injection volume was 5 μL. The total run time was 22 min, including a 2-min equilibration. The MS conditions for positive and negative ion modes were spray voltage at 3.5 kV, sheath gas at 30 arbitrary units, sweep gas at 1 arbitrary units, auxiliary nitrogen pressure at 5 arbitrary units, capillary temperature at 300° C., HESI auxiliary gas heater temperature at 350° C., and S-lens RF at 35 arbitrary units. The instrument was set to acquire in the mass range of most expected cellular lipids and therefore m/z 100-1500 was chosen with a mass resolution of 70,000 (defined at m/z 200). Global lipid profiling was performed using full scan and ddMS2 (data dependent MS-MS).

Data were recorded from 0.0 to 17 min as total ion chromatography (TIC) and then corresponding MS data were extracted using Thermo Xcalibur (version 2.2.44). After data collection, raw data files were converted to mzXML format using the Proteowizard MSConvert software. MZmine 2.15 (freeware) was used for mass detection with mass detector centroid noise set at 1.0E5 using only MS level 1 data; chromatogram building and deconvolution were then applied (m/z tolerance, 0.005 or 10 ppm; retention time tolerance, 0.2 min; minimum time span, 0.1 min; and minimum height, 5.0E5) followed by isotope grouping, alignment (m/z tolerance, 0.005 or 10 ppm; retention time tolerance, 0.2 min), and gap filling (m/z tolerance, 0.005 or 10 ppm; retention time tolerance, 0.2 min, and intensity tolerance 25%). MZmine-based online metabolite search engine KEGG, MMCD database, XCMS online database, Metaboanalyst 3.0, R program, and internal retention time library were used for the identification and analysis of metabolites.

Peptides

The SIM2 (DPEEIIVLSDSD, SEQ ID NO:1) and the TAM RA (5-carboxytetramethylrhodamine)-SIM2 peptides were synthesized at >95% purity by GenScript (Piscataway, NJ).

In Vivo Tumor Growth and Treatment Experiments

All mice were maintained under pathogen-free conditions. Female NSG (NOD.Cg-Prkdc$^{scid}$Il2rg$^{tm1Wjl}$/SzJ) mice, between the ages of 4-6 weeks, were injected subcutaneously in a mammary fat-pad area with one million cells in 100 μl of complete DMEM (MDA-MB-231-derived cell lines) or in a suspension of 50 μl of Matrigel and 50 μl of cell suspension (MDA-MB-468-derived cell lines). The prostate cancer R1-AD1-derived cells (Matrigel suspension) and the colon cancer HCT116-derived cells (medium suspension) were injected subcutaneously in a flank of male NSG mice (the R1-AD1 model) or that of both female and male NSG mice (the HCT116 model). Tumor growth was monitored by measuring tumor dimensions using a digital caliper once a week until endpoint. Tumor volume was calculated with the formula ½×length×width². At the endpoint, mice were euthanized, tumors were excised, weighted, and photographed.

For the in vivo SIM2 treatment study, MDA-MB-231 xenograft tumors were established as above and the mouse mammary tumor cell line 4T1 syngeneic tumors were established by transplanting one million cells in 100 μl of DMEM into mammary fat pads of female BALB/c mice. When tumors grew to a palpable size, tumor-bearing mice were randomized into vehicle and SIM2 treatment arms, so that each group has similar distributions of tumor volumes. The vehicle consisted of 33% (2-Hydroxypropyl)-ẞ-cyclodextrin (HPBCD, RND Center Inc., La Jolla) in PBS and 45% polyethylene glycol 400 (Alfa Aesar, Tewksbury, MA), which was filtered through a 0.22 μm filter. The SIM2 peptide was formulated at 5 mg/ml in the vehicle. Tumor-bearing mice were injected intraperitoneally with 100 μl of vehicle or the formulated SIM2 peptide once daily every weekday until a predefined endpoint. During the treatment, tumor dimensions and mouse body weights were recorded once weekly. At the endpoint, tumors were excised, weights and photographed. Tumors were flash frozen in liquid nitrogen, and then stored at −80° C. Tumor lysates were prepared for immunoblotting analysis. Animal use has been approved for this project by the University of Florida IACUC.

Ingenuity Pathway Analysis (IPA)

Genes that were differentially expressed (fold-change over ±1.3 and p-value<0.05) were used for the Ingenuity Pathway Analysis (Ingenuity Systems, Qiagen Bioinformatics).

Gene Set Enrichment Analysis (GSEA)

GSEA was performed using the Java desktop software, as described previously (Subramanian A, et al. Proc Natl Acad Sci USA 2005 102(43):15545-50). The GSEA tool was used in pre-ranked mode with all default parameters.

ChIP-seq Analysis.

The panel of MDA-MB-231-derived cell lines (control, shDAXX, wt DAXX and DSM mutant OE) were cultured in complete DMEM. At about 90% confluency, the cells were crosslinked by adding 37% formaldehyde to the final concentration of 1% for 10 min at room temperature. Crosslinking was stopped by adding glycine to the final concentration of 125 mM. Cells were lifted, washed with cold PBS, and pelleted by centrifugation. The cells were resuspended in a swelling buffer in the presence of the protease inhibitor cocktail (Sigma) and then pelleted and resuspended in the SDS lysis buffer. The lysates were transferred to a Covaris microTUBE and sonicated with an E220 Covaris Ultrasonicator. Chromatin fragmentation (~500 bps) was verified through agarose gel electrophoresis. The fragmented chromatins were diluted and incubated with a control IgG and the DAXX mAb (5G11) along with protein A/G magnetic beads. The beads were washed sequentially with a low salt buffer, high salt buffer, LiCl buffer, and TE buffer (twice). The immunoprecipitated chromatins were eluted at 65° C. for 15 min, and the eluted chromatins were subjected to proteinase K digestion at 65° C. for 3 h. The DNAs were recovered through a Qiagen mini-prep column.

The immunoprecipitated DNAs were used for qPCR and library construction and high throughput sequencing using an Illumina Hi-Seq 2500 sequencer. ChIP-seq sequencing reads (Fastq files) were mapped to the human genome (GRCh37/hg19) using Bowtie2 (Langmead B, et al. Nat Methods 2012 9(4):357-9), where option—local was specified to trim or clip unaligned reads from one or both ends of the alignment. Genome browser BedGraph tracks and read density histograms were generated using SeqMINER. Peak finding and annotation to the nearest Refseq gene promoter was performed and de novo motif discovery was carried out using HOMER (Heinz S, et al. Mol Cell 2010 38(4):576-89).

Bioinformatics Analysis

The copy number and gene expression were analyzed based on publicly available datasets. Gene expression data for normal, benign, primary, and metastatic tumor samples were included for our analysis. Normalized expression levels for specific genes were compared between different sample types. Computations were conducted in R statistical package and in GraphPad Prism 7.0.

Statistical Analysis

Gene expression assays were conducted in two to three biological replicates. Metabolic profiling assays were performed in >six replicates. Data are presented as the mean along with standard error of the mean (SEM). Student's t-test was used to compare two groups of independent samples. For all data analysis, $p<0.05$ was considered statistically significant.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating cancer in a subject, comprising administering to the subject a therapeutically effective amount of a composition comprising a polypeptide, wherein the polypeptide comprises an amino acid sequence corresponding to at least the C-terminal SUMO-interacting motif (SIM2) of a DAXX protein, and wherein the polypeptide lacks amino acids 1 to 728 of the DAXX protein, wherein the polypeptide is represented by amino acid sequence $X_1PX_2X_3X_4X_5X_6X_7X_8X_9X_{10}X_{11}$ (SEQ ID NO:9), wherein $X_1$ is D or E, $X_2$ is E or D, $X_3$ is E or D, $X_4$ is I, V or L, $X_5$ is I, V, or L, $X_6$ is V, I, or L, $X_7$ is L, I, or V, $X_8$ is S, T, E or D, $X_9$ is D or E, $X_{10}$ is S, T, E or D, and $X_{11}$ is D or E, wherein the cancer is breast cancer, prostate cancer, or colon cancer.

2. The method of claim 1, wherein the polypeptide comprises the amino acid sequence DPEEIIVLSDSD (SEQ ID NO:1, SIM2), having one or two conservative amino acid substitutions that binds SUMO-1.

3. The method of claim 1, wherein the polypeptide consists of the amino acid sequence DPEEIIVLSDSD (SEQ ID NO: 1, SIM2), having one or two conservative amino acid substitutions that binds SUMO-1.

4. The method of claim 1, wherein the polypeptide is represented by an amino acid sequence selected from the group consisting of DPDDIIVLSDSD (SEQ ID NO:2, SIM008), DPEEIIVLSESE (SEQ ID NO:3, SIM009), DPEEIIVLDDDD (SEQ ID NO:4, SIM010), DPEEKIVLSDSD (SEQ ID NO:5, SIM011), DPEEIIDLSDSD (SEQ ID NO:6, SIM012), and EPEEIIVLSDSD (SEQ ID NO:7, SIM013).

5. The method of claim 1, further comprising administering to the subject a checkpoint inhibitor.

6. The method of claim 1, wherein the polypeptide is formulated in a vehicle consisting of 2-Hydroxypropyl)-β-cyclodextrin (HPBCD) solution in a mixture with polyethylene glycols (PEG).

* * * * *